(12) United States Patent
Huang et al.

(10) Patent No.: US 12,239,645 B2
(45) Date of Patent: Mar. 4, 2025

(54) TARGETED DOSING FOR THE TREATMENT OF COMPLEMENT MEDIATED DISORDERS

(71) Applicant: Achillion Pharmaceuticals, Inc., Boston, MA (US)

(72) Inventors: Mingjun Huang, Vancouver, WA (US); Steven D. Podos, New Haven, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 793 days.

(21) Appl. No.: 17/414,057

(22) PCT Filed: Dec. 17, 2019

(86) PCT No.: PCT/US2019/066999
§ 371 (c)(1),
(2) Date: Jun. 15, 2021

(87) PCT Pub. No.: WO2020/131974
PCT Pub. Date: Jun. 25, 2020

(65) Prior Publication Data
US 2022/0079943 A1 Mar. 17, 2022

Related U.S. Application Data

(60) Provisional application No. 62/780,573, filed on Dec. 17, 2018, provisional application No. 62/877,193, filed on Jul. 22, 2019.

(51) Int. Cl.
*A61K 31/506* (2006.01)
*A61K 9/00* (2006.01)
*A61P 7/06* (2006.01)

(52) U.S. Cl.
CPC .......... *A61K 31/506* (2013.01); *A61K 9/0053* (2013.01); *A61P 7/06* (2018.01)

(58) Field of Classification Search
CPC .................................................. A61K 31/506
See application file for complete search history.

(56) References Cited

U.S. PATENT DOCUMENTS

| | | |
|---|---|---|
| 5,628,984 A | 5/1997 | Boucher, Jr. |
| 6,319,897 B1 | 11/2001 | Lambris et al. |
| 6,489,476 B1 | 12/2002 | Dang et al. |
| 6,492,402 B1 | 12/2002 | Lee et al. |
| 6,653,340 B1 | 11/2003 | Babu et al. |
| 7,482,376 B2 | 1/2009 | Subasinghe et al. |
| 7,629,340 B2 | 12/2009 | Schmitz et al. |
| 7,888,323 B2 | 2/2011 | Lambris et al. |
| 7,989,589 B2 | 8/2011 | Lambris |
| 7,999,081 B2 | 8/2011 | Tedesco et al. |
| 8,168,584 B2 | 5/2012 | Deschatelets et al. |
| 8,241,628 B2 | 8/2012 | Diefenbach-Streiber et al. |
| 8,524,716 B2 | 9/2013 | Raboisson et al. |
| 8,580,735 B2 | 11/2013 | Francois et al. |
| 8,883,158 B2 | 11/2014 | Diefenbach-Streiber et al. |
| 8,946,145 B2 | 2/2015 | Lambris et al. |
| 9,056,076 B2 | 6/2015 | Deschatelets et al. |
| 9,085,555 B2 | 7/2015 | Altmann et al. |
| 9,169,307 B2 | 10/2015 | Lambris et al. |
| 9,291,622 B2 | 3/2016 | Zhang et al. |
| 9,371,365 B2 | 6/2016 | Lambris et al. |
| 9,421,240 B2 | 8/2016 | Francois et al. |
| 9,468,661 B2 | 10/2016 | Altmann et al. |
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 9,732,103 B2 | 8/2017 | Wiles et al. |
| 9,732,104 B2 | 8/2017 | Gadhachanda et al. |
| 9,758,537 B2 | 9/2017 | Wiles et al. |
| 9,796,741 B2 | 10/2017 | Gadhachanda et al. |

(Continued)

FOREIGN PATENT DOCUMENTS

| | | |
|---|---|---|
| CN | 101506223 A | 8/2009 |
| CN | 103402996 A | 11/2013 |

(Continued)

OTHER PUBLICATIONS

Andrighetto et al., "Complement and Complement Targeting Therapies in Glomerular Diseases," Int J Mol Sci. 20(24):6336 (Dec. 2019), available <https://www.ncbi.nlm.nih.gov/pmc/articles/PMC6940904/>, retrieved on May 26, 2022 (21 pages).
Extended European Search Report for European Application No. 19857780.1, dated May 13, 2022 (9 pages).
Extended European Search Report for European Application No. 19897806.6, dated Jul. 18, 2022 (12 pages).
Gilkeson, "Complement-Targeted Therapies in Lupus," Curr Treat Options in Rheum. 1:10-18 (2015).
Harris et al., "Developments in anti-complement therapy; from disease to clinical trial," Mol Immunol. 102:89-119 (Oct. 2018).
Hom et al., "Complement Inhibitors for Treatment of Geographic Atrophy and Advanced Nonexudative AMD," Retinal Physician. 16:28-31 (Mar. 1, 2019).
Mantegazza et al., "Complement Inhibition for the Treatment of Myasthenia Gravis," Immunotargets Ther. 9:317-31 (2020), available <https://www.ncbi.nlm.nih.gov/pmc/articles/PMC7751298/>, retrieved on May 26, 2022 (24 pages).

(Continued)

*Primary Examiner* — Rei Tsang Shiao
(74) *Attorney, Agent, or Firm* — Clark & Elbing LLP

(57) ABSTRACT

The dosages and methods described herein provide desirable pharmacokinetic (PK) and pharmacodynamics (PD) characteristics which inhibit alternative pathway complement activity, for example at least 85% or more inhibition of AP activity in vivo at dosages from about 120 mg to 200 mg BID that provides a plasma level $C_{trough}$ at least about 65 ng/ml, which provides sufficient AP inhibition to reduce the risk of complement breakthrough. In addition, the dosage form described herein provides a significantly low $C_{max}$, providing additional safety margin and better dosing flexibility.

13 Claims, 17 Drawing Sheets

(56) References Cited

U.S. PATENT DOCUMENTS

| | | | |
|---|---|---|---|
| 9,828,396 B2 | 11/2017 | Wiles et al. | |
| 9,851,351 B2 | 12/2017 | Reich et al. | |
| 10,000,516 B2 | 6/2018 | Wiles et al. | |
| 10,005,802 B2 | 6/2018 | Wiles et al. | |
| 10,011,612 B2* | 7/2018 | Wiles | C07D 401/14 |
| 10,081,645 B2 | 9/2018 | Wiles et al. | |
| 10,087,203 B2 | 10/2018 | Wiles et al. | |
| 10,092,547 B2 | 10/2018 | Wiles et al. | |
| 10,092,584 B2 | 10/2018 | Wiles et al. | |
| 10,100,072 B2 | 10/2018 | Wiles et al. | |
| 10,106,563 B2 | 10/2018 | Wiles et al. | |
| 10,138,225 B2 | 11/2018 | Wiles et al. | |
| 10,189,869 B2 | 1/2019 | Gadhachanda et al. | |
| 10,253,053 B2 | 4/2019 | Wiles et al. | |
| 10,287,301 B2* | 5/2019 | Wiles | A61P 29/00 |
| 10,301,336 B2 | 5/2019 | Wiles et al. | |
| 10,370,394 B2 | 8/2019 | Wiles et al. | |
| 10,385,097 B2 | 8/2019 | Wiles et al. | |
| 10,428,094 B2 | 10/2019 | Wiles et al. | |
| 10,428,095 B2 | 10/2019 | Wiles et al. | |
| 10,464,956 B2 | 11/2019 | Wiles et al. | |
| 10,550,140 B2 | 2/2020 | Wiles et al. | |
| 10,660,876 B2 | 5/2020 | Wiles et al. | |
| 10,662,175 B2 | 5/2020 | Wiles et al. | |
| 10,689,409 B2 | 6/2020 | Gadhachanda et al. | |
| 10,807,952 B2 | 10/2020 | Wiles et al. | |
| 10,822,352 B2* | 11/2020 | Wiles | A61P 43/00 |
| 10,906,887 B2 | 2/2021 | Wiles et al. | |
| 10,919,884 B2 | 2/2021 | Wiles et al. | |
| 11,001,600 B2 | 5/2021 | Wiles et al. | |
| 11,053,253 B2 | 7/2021 | Wiles et al. | |
| 11,084,800 B2 | 8/2021 | Wiles et al. | |
| 11,407,738 B2 | 8/2022 | Wiles et al. | |
| 11,447,465 B2 | 9/2022 | Wiles et al. | |
| 11,649,223 B2 | 5/2023 | Wiles et al. | |
| 11,649,229 B2 | 5/2023 | Wiles et al. | |
| 11,708,351 B2 | 7/2023 | Wiles et al. | |
| 11,718,626 B2 | 8/2023 | Wiles et al. | |
| 11,807,627 B2* | 11/2023 | Phadke | A61K 31/506 |
| 11,814,363 B2 | 11/2023 | Phadke et al. | |
| 11,814,391 B2 | 11/2023 | Wiles et al. | |
| 12,006,307 B2 | 6/2024 | Wiles et al. | |
| 12,065,459 B2 | 8/2024 | Wiles et al. | |
| 2002/0133004 A1 | 9/2002 | Sekiyama et al. | |
| 2005/0228000 A1 | 10/2005 | Smallheer et al. | |
| 2005/0245497 A1 | 11/2005 | Penfold et al. | |
| 2005/0267108 A1 | 12/2005 | Hsieh et al. | |
| 2006/0004000 A1 | 1/2006 | D'Orchymont et al. | |
| 2007/0155712 A1 | 7/2007 | Zahn et al. | |
| 2008/0075720 A1 | 3/2008 | Holers et al. | |
| 2008/0075728 A1 | 3/2008 | Newman | |
| 2008/0108691 A1 | 5/2008 | Hamann et al. | |
| 2009/0074786 A1 | 3/2009 | Dor et al. | |
| 2009/0162358 A1 | 6/2009 | Alard et al. | |
| 2010/0041628 A1 | 2/2010 | Enomoto et al. | |
| 2011/0082113 A1 | 4/2011 | Hynes et al. | |
| 2011/0280808 A1 | 11/2011 | Kroth et al. | |
| 2012/0231471 A1 | 9/2012 | Sato et al. | |
| 2012/0237515 A1 | 9/2012 | Bell et al. | |
| 2012/0295884 A1 | 11/2012 | Altmann et al. | |
| 2013/0029912 A1 | 1/2013 | Holers et al. | |
| 2013/0035392 A1 | 2/2013 | McGeer et al. | |
| 2013/0296377 A1 | 11/2013 | Adams et al. | |
| 2013/0324482 A1 | 12/2013 | Francois et al. | |
| 2013/0344073 A1 | 12/2013 | Schwaeble et al. | |
| 2014/0050739 A1 | 2/2014 | Francois et al. | |
| 2014/0323407 A1 | 10/2014 | Francois et al. | |
| 2014/0371133 A1 | 12/2014 | Francois et al. | |
| 2015/0079613 A1 | 3/2015 | McKnight et al. | |
| 2015/0141455 A1 | 5/2015 | Altmann et al. | |
| 2015/0148374 A1 | 5/2015 | Hommel et al. | |
| 2015/0158915 A1 | 6/2015 | Lambris et al. | |
| 2015/0191462 A1 | 7/2015 | Hommel et al. | |
| 2015/0239837 A1 | 8/2015 | Wiles et al. | |
| 2015/0239838 A1 | 8/2015 | Phadke et al. | |
| 2015/0239868 A1 | 8/2015 | Pais et al. | |
| 2015/0239893 A1 | 8/2015 | Wang et al. | |
| 2015/0239894 A1 | 8/2015 | Gadhachanda et al. | |
| 2015/0239895 A1 | 8/2015 | Gadhachanda et al. | |
| 2015/0239919 A1 | 8/2015 | Gadhachanda et al. | |
| 2015/0239920 A1 | 8/2015 | Gadhachanda et al. | |
| 2015/0239921 A1 | 8/2015 | Wiles et al. | |
| 2015/0269868 A1 | 9/2015 | Carney et al. | |
| 2015/0322060 A1 | 11/2015 | Flohr et al. | |
| 2015/0368271 A1 | 12/2015 | Su et al. | |
| 2016/0015810 A1 | 1/2016 | Deschatelets et al. | |
| 2016/0024079 A1 | 1/2016 | Adams et al. | |
| 2016/0060297 A1 | 3/2016 | Deschatelets et al. | |
| 2016/0194359 A1 | 7/2016 | Francois et al. | |
| 2016/0215020 A1 | 7/2016 | Francois et al. | |
| 2016/0215022 A1 | 7/2016 | Francois et al. | |
| 2016/0361329 A1 | 12/2016 | Wiles et al. | |
| 2016/0362398 A1 | 12/2016 | Wiles et al. | |
| 2016/0362399 A1 | 12/2016 | Wiles et al. | |
| 2016/0362432 A1 | 12/2016 | Wiles et al. | |
| 2016/0362433 A1 | 12/2016 | Wiles et al. | |
| 2017/0056428 A1 | 3/2017 | Wiles et al. | |
| 2017/0057950 A1 | 3/2017 | Wiles et al. | |
| 2017/0057983 A1 | 3/2017 | Wiles et al. | |
| 2017/0057993 A1 | 3/2017 | Wiles et al. | |
| 2017/0066783 A1 | 3/2017 | Wiles et al. | |
| 2017/0189410 A1 | 7/2017 | Gadhachanda et al. | |
| 2017/0202821 A1 | 7/2017 | Bekker | |
| 2017/0202935 A1 | 7/2017 | Lambris et al. | |
| 2017/0226142 A1 | 8/2017 | Wiles et al. | |
| 2017/0260219 A1 | 9/2017 | Wiles et al. | |
| 2017/0298084 A1 | 10/2017 | Wiles et al. | |
| 2017/0298085 A1 | 10/2017 | Wiles et al. | |
| 2018/0022766 A1 | 1/2018 | Wiles et al. | |
| 2018/0022767 A1 | 1/2018 | Wiles et al. | |
| 2018/0030075 A1 | 2/2018 | Wiles et al. | |
| 2018/0072762 A1 | 3/2018 | Wiles et al. | |
| 2018/0177761 A1 | 6/2018 | Wiles et al. | |
| 2018/0179185 A1 | 6/2018 | Wiles et al. | |
| 2018/0179186 A1 | 6/2018 | Wiles et al. | |
| 2018/0179236 A1 | 6/2018 | Wiles et al. | |
| 2018/0186782 A1 | 7/2018 | Wiles et al. | |
| 2018/0201580 A1 | 7/2018 | Wiles et al. | |
| 2018/0291046 A1 | 10/2018 | Wiles et al. | |
| 2018/0291047 A1 | 10/2018 | Wiles et al. | |
| 2018/0305375 A1 | 10/2018 | Wiles et al. | |
| 2019/0023729 A1 | 1/2019 | Wiles et al. | |
| 2019/0031692 A1 | 1/2019 | Wiles et al. | |
| 2019/0038623 A1 | 2/2019 | Huang et al. | |
| 2019/0048033 A1 | 2/2019 | Wiles et al. | |
| 2019/0085005 A1 | 3/2019 | Wiles et al. | |
| 2019/0144473 A1 | 5/2019 | Gadhachanda et al. | |
| 2019/0151334 A1 | 5/2019 | Bosworth et al. | |
| 2019/0211033 A1 | 7/2019 | Wiles et al. | |
| 2019/0359645 A1 | 11/2019 | Birkus et al. | |
| 2019/0382376 A1 | 12/2019 | Wiles et al. | |
| 2020/0002347 A1 | 1/2020 | Wiles et al. | |
| 2020/0062790 A1 | 2/2020 | Wiles et al. | |
| 2020/0071301 A1 | 3/2020 | Wiles et al. | |
| 2020/0101071 A1 | 4/2020 | Huang et al. | |
| 2020/0262818 A1 | 8/2020 | Wiles et al. | |
| 2021/0332026 A1 | 10/2021 | Phadke et al. | |
| 2023/0071620 A1 | 3/2023 | Wiles et al. | |

FOREIGN PATENT DOCUMENTS

| | | |
|---|---|---|
| CN | 103561739 A | 2/2014 |
| CN | 108024992 A | 5/2018 |
| CN | 110603252 A | 12/2019 |
| EA | 201590118 A1 | 4/2015 |
| EA | 23259 B1 | 5/2016 |
| EA | 201890594 A1 | 8/2018 |
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |

(56) References Cited

FOREIGN PATENT DOCUMENTS

| | | |
|---|---|---|
| JP | 2018-526367 A | 9/2018 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| JP | 7210637 B2 | 1/2023 |
| KR | 2014-0027090 A | 3/2014 |
| KR | 10-2016-0116014 A | 10/2016 |
| MX | /A/2021/003425 | 7/2021 |
| RU | 2202344 C2 | 4/2003 |
| RU | 2470918 C2 | 12/2012 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/002067 A2 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO-2017/127761 A1 | 7/2017 |
| WO | WO-2017/136395 A1 | 8/2017 |
| WO | WO-2018/005552 A1 | 1/2018 |
| WO | WO-2018/026722 A1 | 2/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/041301 A1 | 2/2020 |
| WO | WO-2020/051538 A1 | 3/2020 |
| WO | WO-2020/069024 A1 | 4/2020 |
| WO | WO-2020/109343 A1 | 6/2020 |
| WO | WO-2021/021909 A1 | 2/2021 |
| WO | WO-2021/252669 A1 | 12/2021 |
| WO | WO-2022/047128 A2 | 3/2022 |

OTHER PUBLICATIONS

Partial Supplementary European Search Report for European Application No. 19857913.8, dated Apr. 13, 2022 (17 pages).
Patient Information for TARPEYO (tar-PAY-oh) (budesonide) delayed release capsules, Calliditas Therapeutics AB, 2021 (2 pages).
Risitano et al., "Danicopan: an oral complement factor D inhibitor for paroxysmal nocturnal hemoglobinuria," Haematologica. 106(12):3188-97 (2021).
Varelas et al., "Complement in Sickle Cell Disease: Are We Ready for Prime Time?," J Blood Med. 12:177-87 (2021), available <https://www.ncbi.nlm.nih.gov/pmc/articles/PMC8001680/>, retrieved on May 26, 2022 (19 pages).
Willows et al., "The role of complement in kidney disease," Clin Med (Lond). 20(2):156-60 (2020) (9 pages).
U.S. Appl. No. 16/006,476, Wiles et al.
U.S. Appl. No. 16/006,533, Wiles et al.
"Are There Any Treatments for ALS?" WebMD, <https://www.webmd.com/brain/understanding-als-treatment#1>, retrieved on May 3, 2019 (8 pages).
"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).
"Cancer," MedLine Plus, <http://www.nlm.nih.gov/medlineplus/cancer.html>, retrieved Jul. 6, 2007 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, last reviewed May 31, 2017 (4 pages).
"What is Dementia?" Alzheimer's Association, <https://www.alz.org/alzheimers-dementia/what-is-dementia>, retrieved on Nov. 17, 2020 (6 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).

(56) References Cited

OTHER PUBLICATIONS

Babiker et al., "Transfer of prostasomal CD59 to CD59-deficient red blood cells results in protection against complement-mediated hemolysis," Am J Reprod Immunol. 47(3): 183-92 (2002) (Abstract Only).
Barraclough et al., "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).
Brodsky, "Eculizumab: another breakthrough," Blood. 129(8):922-3 (2017).
Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, created Aug. 20, 2012, retrieved Jul. 14, 2020 (9 pages).
Damasio, "Alzheimer's disease and related dementias," Cecil Textbook of Medicine, 20th Edition, vol. 2. Bennet and Plum, Jun. 1992 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C--H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) For Treatment of PNH, C3G and Complement-Mediated Diseases: Interim Phase 1 Results In Healthy Volunteers," European Hematology Association, Copenhagen 21st Congress, Jun. 9-12, Abstract ID: EHA-4145 (2016).
Extended European Search Report for European Application No. 18761960.6, dated Mar. 1, 2021 (10 pages).
Extended European Search Report for European Application No. 18840849.6, dated Mar. 17, 2021 (11 pages).
Extended European Search Report for European Application No. 19807154.0, dated Feb. 7, 2022 (9 pages).
Gadhachanda et al., CAplus Database Summary Sheet for Document No. 164:507515, Accession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood. 129(8):970-80 (2017).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
Hu et al., "Evidence of complement dysregulation in outer retina of Stargardt disease donor eyes," Redox Biol. 37:101787 (2020) (10 pages).
International Search Report and Written Opinion for International Application No. PCT/US2015/017523, mailed May 14, 2015 (7 pages).
International Search Report and Written Opinion for International Application No. PCT/US2015/017538, mailed May 14, 2015 (8 pages).
International Search Report and Written Opinion for International Application No. PCT/US2015/017554, mailed May 14, 2015 (7 pages).
International Search Report and Written Opinion for International Application No. PCT/US2015/017583, mailed May 27, 2015 (12 pages).
International Search Report and Written Opinion for International Application No. PCT/US2015/017593, mailed Jun. 16, 2015 (6 pages).
International Search Report and Written Opinion for International Application No. PCT/US2015/017597, mailed Jan. 29, 2016 (10 pages).
International Search Report and Written Opinion for International Application No. PCT/US2015/017600, mailed May 27, 2015 (12 pages).
International Search Report and Written Opinion for International Application No. PCT/US2015/017609, mailed May 29, 2015 (6 pages).

(56) References Cited

OTHER PUBLICATIONS

International Search Report and Written Opinion for International Application No. PCT/US2016/048688, mailed Dec. 28, 2016 (11 pages).
International Search Report and Written Opinion for International Application No. PCT/US2016/048690, mailed Dec. 28, 2016 (11 pages).
International Search Report and Written Opinion for International Application No. PCT/US2016/048693, mailed Jan. 13, 2017 (11 pages).
International Search Report and Written Opinion for International Application No. PCT/US2016/048695, mailed Dec. 30, 2016 (10 pages).
International Search Report and Written Opinion for International Application No. PCT/US2016/048696, mailed Jan. 5, 2017 (10 pages).
International Search Report and Written Opinion for International Application No. PCT/US2016/048701, mailed Jan. 10, 2017 (10 pages).
International Search Report and Written Opinion for International Application No. PCT/US2016/048704, mailed Dec. 27, 2016 (7 pages).
International Search Report and Written Opinion for International Application No. PCT/US2016/048707, mailed Jan. 5, 2017 (10 pages).
International Search Report and Written Opinion for International Application No. PCT/US2016/048709, mailed Jan. 17, 2017 (9 pages).
International Search Report and Written Opinion for International Application No. PCT/US2016/048710, mailed Jan. 5, 2017 (8 pages).
International Search Report and Written Opinion for International Application No. PCT/US2016/048779, mailed Dec. 27, 2016 (8 pages).
International Search Report and Written Opinion for International Application No. PCT/US2016/048783, mailed Feb. 3, 2017 (8 pages).
International Search Report and Written Opinion for International Application No. PCT/US2016/048787, mailed Jan. 5, 2017 (13 pages).
International Search Report and Written Opinion for International Application No. PCT/US2016/048788, mailed Jan. 5, 2017 (12 pages).
International Search Report and Written Opinion for International Application No. PCT/US2016/048793, mailed Dec. 28, 2016 (8 pages).
International Search Report and Written Opinion for International Application No. PCT/US2016/048795, mailed Feb. 17, 2017 (12 pages).
International Search Report and Written Opinion for International Application No. PCT/US2016/048797, mailed Jan. 5, 2017 (12 pages).
International Search Report and Written Opinion for International Application No. PCT/US2016/048799, mailed Nov. 15, 2016 (7 pages).
International Search Report and Written Opinion for International Application No. PCT/US2016/048800, mailed Jan. 5, 2017 (12 pages).
International Search Report and Written Opinion for International Application No. PCT/US21/18871, mailed May 24, 2021 (24 pages).
International Search Report and Written Opinion for International Application No. PCT/US21/21563, mailed May 18, 2021 (15 pages).
International Search Report for International Application No. PCT/US18/20530, mailed Jun. 25, 2018 (3 pages).
International Search Report for International Application No. PCT/US20/24017, mailed Jun. 26, 2020 (3 pages).
International Search Report for International Application No. PCT/US2018/020528, mailed Apr. 24, 2018 (3 pages).
International Search Report for International Application No. PCT/US2018/045057, mailed Nov. 15, 2018 (5 pages).
International Search Report for International Application No. PCT/US18/20531, dated May 15, 2018 (3 pages).
International Search Report for International Application No. PCT/US2019/034210, mailed Sep. 13, 2019 (4 pages).
International Search Report for International Application No. PCT/US2019/047252, mailed Dec. 17, 2019 (4 pages).
International Search Report for International Application No. PCT/US2019/050065, mailed Feb. 25, 2020 (4 pages).
International Search Report for International Application No. PCT/US2019/050073, mailed Nov. 21, 2019 (3 pages).
International Search Report for International Application No. PCT/US2019/053012, mailed Jan. 28, 2020 (4 pages).
International Search Report for International Application No. PCT/US2019/066999, mailed Feb. 12, 2020 (3 pages).
Ishibashi et al., "Four-year outcomes of intravitreal aflibercept treatment for neovascular age-related macular degeneration using a treat-and-extend regimen in Japanese patients," Ther Adv Ophthalmol. 13:1-5 (2021).
Jensen et al., "Associations between the Complement System and Choroidal Neovascularization in Wet Age-Related Macular Degeneration," Int J Mol Sci. 21(24):9752 (2020) (28 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019, (1 page).
Kinman, "COPD Drugs: A List of Medications to Help Relieve Your Symptoms," Healthline, <https://www.healthline.com/health/copd/drugs>, retrieved on May 3, 2019 (12 pages).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (2018) (1 page) (Abstract only).
Komiya et al., CAplus Database Summary Sheet for Document No. 162:229476, Accession No. 2015:126147, CAplus on STN. (2015) (2 pages).
Konar et al., "Eculizumab treatment and impaired opsonophagocytic killing of meningococci by whole blood from immunized adults," Blood. 130(7):891-9 (2017).
Krauss, "Laboratory Diagnosis of Paroxysmal Nocturnal Hemoglobinuria," Annals of Clinical & Laboratory Science. 33(4):401-406 (2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition*, vol. 2. J. Claude Bennett and Fred Plum, p. 2050-2057 (1996) (9 pages).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33(6):479-92 (2013).

(56) References Cited

OTHER PUBLICATIONS

Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Oshima et al., "Correlation between improvement in visual acuity and QOL after Ranibizumab treatment for age-related macular degeneration patients: Quatro study," BMC Ophthalmol. 21(1):58 (2021) (11 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria," 59th American Society of Hematology Annual Meeting and Exposition, Dec. 9-12, Atlanta, Georgia. Poster Abstract 2198 (2017).
Pearce et al., Chapter 18: Failure modes in anticancer drug discovery and development. *Cancer Drug Design and Discovery*. Stephen Neidle, 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann—Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).
Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure—Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," Plos One. 9(10):e110053 (2014) (9 pages).
Sica et al., "Eculizumab treatment: stochastic occurrence of C3 binding to individual PNH erythrocytes," J Hematol Oncol. 10(1): 126 (2017) (10 pages).
Simone, "Oncology: Introduction," Cecil Textbook of Medicine, 20th Edition, vol. 1, pp. 1004-1010, (1996).
Stanton et al., "Complement Factor D in Age-Related Macular Degeneration," Invest Ophthalmol Vis Sci. 52(12):8828-8834 (2011) (15 pages).
Steinle et al., "Impact of Baseline Characteristics on Geographic Atrophy Progression in the FILLY Trial Evaluating the Complement C3 Inhibitor Pegcetacoplan," Am J Ophthalmol. DOI: https://doi.org/10.1016/j.ajo.2021.02.031 (Journal Pre-proof version) (2021) (19 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al., "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
Written Opinion for International Application No. PCT/US18/20528, mailed Apr. 24, 2018 (6 pages).
Written Opinion for International Application No. PCT/US18/20530, mailed Jun. 25, 2018 (6 pages).
Written Opinion for International Application No. PCT/US18/20531, mailed May 15, 2018 (7 pages).
Written Opinion for International Application No. PCT/US19/47252, mailed Dec. 17, 2019 (6 pages).
Written Opinion for International Application No. PCT/US19/50065, mailed Feb. 25, 2020 (7 pages).
Written Opinion for International Application No. PCT/US19/53012, mailed Jan. 28, 2020 (5 pages).
Written Opinion for International Application No. PCT/US19/66999, mailed Feb. 12, 2020 (7 pages).
Written Opinion for International Application No. PCT/US20/24017, mailed Jun. 26, 2020 (6 pages).
Written Opinion for International Application No. PCT/US2018/045057, mailed Nov. 15, 2018 (7 pages).
Written Opinion for International Application No. PCT/US2019/034210, mailed Sep. 13, 2019 (17 pages).
Written Opinion for International Application No. PCT/US2019/050073, mailed Nov. 21, 2019 (4 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
Verbeeck et al., "Generic substitution: the use of medicinal products containing different salts and implications for safety and efficacy," Eur J Pharm Sci. 28(1-2):1-6 (May 2006).
Iyer et al., "Chemical Approaches to Modulating Complement-Mediated Diseases," J Med Chem. 61(8):3253-76 (Apr. 26, 2018).
Polymorphic Drugs, Lu Yang et al., People's Medical Publishing House, pp. 6, 24-26, 138, Publication date: Oct. 31, 2009 (7 pages).
Ohlsson, Chapter 14: Urinary Biomarkers in Glomerulonephritis. *An Update on Glomerulopathies—Etiology and Pathogenesis*. ed. Prof. Sharma Prabhakar, InTech, 269-276 (2011).
Garred et al., "Therapeutic Targeting of the Complement System: From Rare Diseases to Pandemics," Pharmacol Rev. 73(2):792-827 (Apr. 2021).

(56) References Cited

OTHER PUBLICATIONS

Caira, "Crystalline polymorphism of organic compounds," *Topics in Current Chemistry*, vol. 198. Springer Verlag Berlin Heidelberg, 163-208 (1998).

Yamano, M., "Approach to Crystal Polymorph in Process Research of New Drug," Journal of Synthetic Organic Chemistry, Japan. 65(9):907-13 (2007) (7 pages).

Takada, "API form screening and selection in drug discovery stage," Pharm Stage. 6(10):20-25 (2007) (9 pages).

"Complement Inhibitors as Therapeutic Agents," Biopharma PEG, Jul. 11, 2022, available <https://www.biochempeg.com/article/281.html>, (11 pages).

Michels et al., "Long-term follow-up including extensive complement analysis of a pediatric C3 glomerulopathy cohort," Pediatr Nephrol. 37(3):601-12 (Mar. 2022).

Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).

International Search Report for International Application No. PCT/US24/17823, mailed May 30, 2024 (3 pages).

Wermuth, Molecular Variations Based on Isosteric Replacements. *The Practice of Medicinal Chemistry*. Academic Press, 203-37 (1996).

International Preliminary Report on Patentability for International Application No. PCT/US2021/018871, mailed Sep. 1, 2022 (6 pages).

16th revision Japanese Pharmacopoeia, 2011, pp. 64-68, 2070.

Hilfiker et al., Chapter 1: Relevance of Solid-state Properties for Pharmaceutical Products. *Polymorphism: in the Pharmaceutical Industry*. Wiley, 1-19 (2006).

Pharmacy—Basics and Applications—, Nanzando Co., Ltd., Sep. 20, 1977, p. 142-145.

Oshima et al., "Crystallization of polymorphs and pseudo-polymorphs and its control," Pharm Stage. 6(10):48-53 (2007) (8 pages).

New General Theory of Pharmacy (revised 3rd edition), Apr. 10, 1987, Nankodo Co., Ltd., p. 111.

Written Opinion for International Application No. PCT/US24/17823, mailed May 30, 2024 (6 pages).

Kazuhide Ashizawa et al., Science of polymorphism and crystallization of pharmaceuticals, Japan, Maruzen Planet Co., Ltd., Sep. 20, 2002, p. 3-16, 273-278.

Braga et al., "Crystal polymorphism and multiple crystal forms," Structure Bond. 132: 25-50 (2009).

New Pharmaceutical Science, Nanzando Co., Ltd., Apr. 25, 1984, p. 102-103, 232-233.

Zhang et al., "Defining the complement biomarker profile of C3 glomerulopathy," Clin J Am Soc Nephrol. 9(11):1876-82 (supplemental materials) (Nov. 7, 2014) (10 pages).

Wiles et al., "Discovery and Development of the Oral Complement Factor D Inhibitor Danicopan (ACH-4471)," Curr Med Chem. 27(25):4165-80 (2020).

Marinozzi et al., "C5 nephritic factors drive the biological phenotype of C3 glomerulopathies," Kidney Int. 92(5):1232-41 (Nov. 2017).

Experimental Chemistry Course (continued) 2 Separation and Purification, Maruzen Co., Ltd., Jan. 25, 1967, p. 159-178, 186-187.

Extended European Search Report for European Application No. 21757829.3, dated May 27, 2024 (10 pages).

Office Action issued for Chinese Patent Application No. 201980086227.3, dated Jul. 4, 2024 (11 pages).

\* cited by examiner

PK-PD Relationship Between Compound 1 Plasma Concentrations (PK) and *Ex vivo* AP Hemolysis Inhibition (PD) Among Multiple Dose Subjects ($E_{max}$ model)

PK-PD Relationship Between Compound 1 Plasma Concentrations (PK) and *Ex vivo* AP Hemolysis Inhibition (PD) Among Multiple Dose Subjects (Sigmoidal model)

TARGETED DOSING FOR THE TREATMENT OF COMPLEMENT MEDIATED DISORDERS

CROSS-REFERENCE TO RELATED APPLICATIONS

This application claims the benefit of U.S. Provisional Application No. 62/780,573, filed Dec. 17, 2018, and U.S. Provisional Application No. 62/877,193, filed Jul. 22, 2019. These applications are incorporated by reference in their entireties.

FIELD OF THE INVENTION

This invention is in the area of advantageous dosage forms and methods of administering a small molecule complement factor D (fD) inhibitor—(1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide—which provide for specific pharmacokinetic and pharmacodynamic profiles in a human for the treatment of complement-mediated disorders based on human clinical trials. In one aspect, dosage forms that provide desirable pharmacokinetic and pharmacodynamic characteristics, including $C_{trough}$ are disclosed.

BACKGROUND

An immune disorder occurs when the immune system is not performing in a normal manner. Inflammation is a protective response that involves immune cells, the immune system generally, blood vessels, and molecular mediators. A wide variety of medical disorders are caused by detrimental immune or inflammatory responses, or the inability of a cell to respond to a normal immune or inflammatory process.

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells) and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within C3 to produce C3($H_2O$), which associates with Factor B to form the C3($H_2O$)B complex. Complement Factor D acts to cleave Factor B within the C3($H_2O$)B complex to form Ba and Bb. The Bb fragment remains associated with C3($H_2O$) to form the alternative pathway C3 convertase C3($H_2O$)Bb. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Other disorders that have been linked to the complement cascade include, but are not limited to, atypical hemolytic uremic syndrome (aHUS), hemolytic uremic syndrome (HUS), C3 glomerulopathy (C3G) or C3 glomerulonephritis (C3GN), abdominal aortic aneurysm, hemodialysis complications, hemolytic anemia, or hemodialysis, neuromyelitis (NMO), myasthenia gravis (MG), fatty liver, nonalcoholic steatohepatitis (NASH), liver inflammation, cirrhosis, liver failure, dermatomyositis, amyotrophic lateral sclerosis, age-related macular degeneration (AMD), multiple sclerosis, rheumatoid arthritis, and cytokine or inflammatory reactions in response to biotherapeutics (e.g. CAR T-cell therapy).

Factor D is an attractive target for inhibition or regulation of the complement cascade due to its early and essential role in the alternative complement pathway, and its potential role in signal amplification within the classical and lectin complement pathways. Inhibition of Factor D effectively interrupts the pathway and attenuates the formation of the membrane attack complex. While initial attempts have been made to develop inhibitors of Factor D, there are currently no clinically approved small molecule Factor D inhibitors. Examples of Factor D inhibitor compounds are described in the following disclosures Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications: WO2012093101, WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, and WO2016088082.

Additional complement factor D inhibitors are described in patent filings owned by Achillion Pharmaceuticals, Inc U.S. Pat. Nos. 9,598,446; 9,643,986; 9,663,543; 9,695,205; 9,732,103; 9,732,104; 9,758,537; 9,796,741; 9,828,396;

10,000,516; 10,005,802; 10,011,612; 10,081,645; 10,087,203; 10,092,584; 10,100,072; 10,138,225; 10,189,869; 10,106,563; 10,301,336; and 10,287,301; International Publication Nos. WO2019/028284; WO2018/160889; WO2018/160891; WO2018/160892; WO2017/035348; WO2017/035349; WO 2017/035351; WO 2017/035352; WO 2017/035353; WO 2017/035355; WO2017/035357; WO2017/035360; WO2017/035361; WO2017/035362; WO2017/035415; WO2017/035401; WO2017/035405; WO2017/035413; WO2017/035409; WO2017/035411; WO2017/035417; WO2017/035408 WO2015/130784; WO2015/130795; WO2015/130806; WO2015/130830; WO2015/130838; WO2015/130842; WO2015/130845; and WO2015/130854; and U.S. Patent Publication Nos. US 2016-0361329; US 2016-0362432; US 2016-0362433; US 2016-0362399; US 2017-0056428; US 2017-0057950; US 2017-0057993; US 2017-0189410; US 2017-0226142; US 2017-0260219; US 2017-0298084; US 2017-0298085; US 2018-0022766; US 2018-0022767; US 2018-0072762; US 2018-0030075; US 2018-0169109; US 2018-0177761; US 2018-0179185; US 2018-0179186; US 2018-0179236; US 2018-0186782; US 2018-0201580; US 2019-0031692; US 2019-0048033; US 2019-0144473; and US 2019-0211033.

Lifesci Pharmaceuticals PCT patent publication WO2017/098328 titled "Therapeutic Inhibitory Compounds" describes various Factor D inhibitors with variations in the central core heterocyclic ring. PCT patent publication WO2018/015818 is also titled "Therapeutic Inhibitory Compounds" and describes Factor D inhibitors without a cyclic central core.

Biocryst Pharmaceuticals U.S. Pat. No. 6,653,340 titled "Compounds useful in the complement, coagulation and kallikrein pathways and method for their preparation" describes fused bicyclic ring compounds that are inhibitors of Factor D. Development of the Factor D inhibitor BCX1470 was discontinued due to lack of specificity and short half-life of the compound.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibodies eculizumab (Soliris®) and ravulizumab-cwvz (Ultomiris®) are currently the only complement-specific antibody on the market, and the only approved treatments for paroxysmal nocturnal hemoglobinuria (PNH).

One particular difficulty associated with the treatment of complement-mediated disorders is the duration of anti-complement activity during dosing intervals, and the possibility for the development of breakthrough hemolysis prior to receiving the next course of therapy. For example, eculizumab dosing intervals longer than 17 days may be associated with a greater risk of breakthrough hemolysis in patients with PNH. Nakayama et al., Bio. Pharm. Bull. 2018; 39(2), 285-288.

Given the wide variety of medical disorders that are caused by detrimental immune or inflammatory responses, it is an object of the present invention to provide dosages and methods to treat patients having complement-mediated disorders that provide desirable pharmacokinetic and pharmacodynamic characteristics for inhibiting the alternative complement pathway which are durable between administration of therapeutic doses.

SUMMARY OF THE INVENTION

This invention is in the area of advantageous oral dosage forms and methods of administering the small molecule complement factor D (fD) inhibitor—(1R,3 S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1; see structure below) which provide a pharmacokinetic $C_{trough}$ over time that maintains the effectiveness of the drug while minimizing side effects. The $C_{trough}$ is defined as the mean plasma concentration at the end of the dosage interval or the minimum mean plasma concentration. A dosage interval is defined as the point just before repeating the dosage. For example, if the dosage is two times a day (BID), then the dosage interval is the time period between taking the first dose and taking the second dose that day, or the second dose and the first dose the next day.

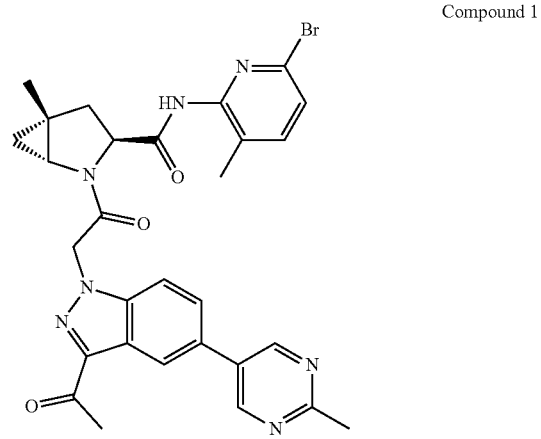 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)cc12]

Compound 1

This invention is important because of the criticality and sensitivity of the complement cascade given its role to attack and destroy cells that it perceives as foreign, diseased or infected. If the dose is too high, it is possible to cause undesired side effects such as inhibiting the ability to fight infection or causing organ toxicity. If the dose is too low, the drug is not effective to counterbalance the overactivity or dysfunctional activity of the alternative complement pathway system.

It has been surprisingly discovered that Compound 1 exhibits a diurnal metabolic pattern in humans, which means that it is metabolized significantly more during the day than at night. This could not have been predicted prior to human administration of the drug. For example, Table 6 provides the mean (ng/mL) at $C_{(0)}$ and $C_{(12)}$ at four doses (40, 80, 120, and 200 mg BID for 14 days) For each of the four dosage regimes, the $C_{(0)}$, which is measured in the morning is significantly higher, and in fact almost double, the $C_{(12)}$, which is measured in the evening. Surprisingly and unexpectedly, this is in contrast to a Complement Factor D inhibitor of a very similar structure, Compound 2 (below), (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide, which does not exhibit a diurnal metabolic pattern when administered to humans.

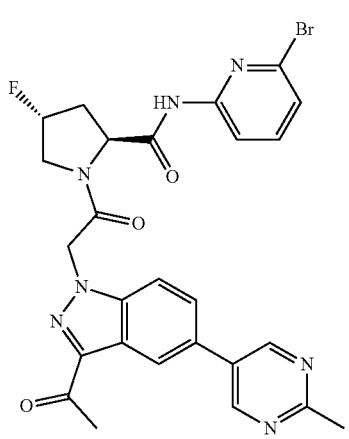

Compound 2

It has been discovered that at an oral dosage of Compound 1 of about 100 mg to 200 mg twice a day, more specifically about 120 mg to 180 mg twice a day, and even more specifically about 120 mg to 150 mg twice a day, or about 150 mg to about 200 mg twice a day, and in one embodiment about 120 mg twice a day, provides an optimal minimum mean plasma concentration ($C_{trough}$) at the end of the dosage interval such that the dosage does not fall below its $EC_{90}$ effectiveness at any time during the day. Specifically, a dosage regimen was discovered that maintains the lower of the two diurnal minimum mean plasma concentrations ($C_{trough}$) above the established $EC_{90}$. Modeling, as described further below, established an $EC_{90}$ of between 67-88 ng/mL will provide about 90% AP activity inhibition. Data derived from a multiple ascending dosing study (MAD; described further below) in healthy subject sera in ex vivo alternative pathway activity assays establishes that about 90% AP activity inhibition can be achieved at a minimum mean plasma concentration ($C_{trough}$) of about 80 ng/mL (see Table 6 and Table 7); a greater than 95% AP activity inhibition can be achieved at a minimum mean plasma concentration ($C_{trough}$) of about 150 ng/mL (see Table 6 and Table 7). Surprisingly, the minimum mean plasma concentration ($C_{trough}$) of about 80 ng/mL is achieved at the lower $C_{trough}$ level in the diurnal cycle of a 120 mg BID dosing regimen.

Therefore, as a result of human clinical trials as described in detail below, an oral dosage regime has been surprisingly identified that can guide the safe and effective long-term administration of a complement factor D (fD) inhibitor Compound 1, or a pharmaceutically acceptable salt thereof, that can be used to treat a subject having a dysfunction of, or excessive activation of complement, for example, but not limited to, paroxysmal nocturnal hemoglobinuria (PNH), C3 glomerulopathy (C3G) such as dense deposit disease (DDD) and C3 glomerulonephritis (C3GN), and immune-complex membranoproliferative glomerulonephritis (IC-MPGN). The dosages and methods described herein provide desirable pharmacokinetic (PK) and pharmacodynamic (PD) characteristics which inhibit alternative pathway complement activity, for example at least 85%, at least 90%, at least 95% or more inhibition of AP activity in vivo at dosages between 120 mg and 200 mg BID that provide a minimum mean plasma concentration ($C_{trough}$) of between about 65 and 450 ng/mL, sufficiently high enough to avoid complement breakthrough.

In some embodiments, a dosage is provided that provides for a minimum mean plasma concentration ($C_{trough}$) of between about 50 and 450 ng/mL. In some embodiments, a dosage is provided that provides for a minimum mean plasma concentration ($C_{trough}$) of between about 75 and 160 ng/mL. In some embodiments, a dosage is provided that provides for a minimum mean plasma concentration ($C_{trough}$) of between about 80 and 150 ng/mL.

In some embodiments, a dosage is provided that provides for a minimum mean plasma concentration ($C_{trough}$) of at least about 65 ng/mL at the lower $C_{trough}$ level in the diurnal cycle of a BID dosing regimen. In some embodiments, a dosage is provided that provides for a minimum mean plasma concentration ($C_{trough}$) of at least about 80 ng/mL at the lower $C_{trough}$ level in the diurnal cycle of a BID dosing regimen. In some embodiments, a dosage is provided that provides for a minimum mean plasma concentration ($C_{trough}$) of at least about 90 ng/mL at the lower $C_{trough}$ level in the diurnal cycle of a BID dosing regimen. In some embodiments, a dosage is provided that provides for a minimum mean plasma concentration ($C_{trough}$) of at least about 100 ng/mL at the lower $C_{trough}$ level in the diurnal cycle of a BID dosing regimen. In some embodiments, a dosage is provided that provides for a minimum mean plasma concentration ($C_{trough}$) of at least about 125 ng/mL at the lower $C_{trough}$ level in the diurnal cycle of a BID dosing regimen. In some embodiments, a dosage is provided that provides for a minimum mean plasma concentration ($C_{trough}$) of at least about 150 ng/mL at the lower $C_{trough}$ level in the diurnal cycle of a BID dosing regimen. In some embodiments, a dosage regimen is provided that provides a minimum mean plasma concentration ($C_{trough}$) of between about 65 ng/mL and 150 ng/mL at the lower $C_{trough}$ level in the diurnal cycle of a BID dosing regimen.

Furthermore, when dosed at 120 mg BID and higher (e.g., 200 mg BID), Compound 1 achieved near complete and sustained Alternative Pathway (AP) inhibition with a mean value of >90% at minimum mean plasma concentrations ($C_{trough}$) as measured by AP Hemolysis and AP Wieslab assays at 120 mg BID and about >95% at 200 mg BID (see Table 7). The $C_{trough}$ was effectively achieved with relatively low Compound 1 exposure, with a $C_{max}$ of less than about 1000 ng/mL observed with the 120 mg BID and a $C_{max}$ of less than 2000 ng/mL associated with the 200 mg BID. The ability to maintain inhibition of the AP between dosing allows for an advantageous dosing regimen that is safe and convenient to patients, reducing the risk of breakthrough hemolysis associated with ineffective $C_{trough}$ and toxicity associated with excessive $C_{max}$.

In one aspect, Compound 1 is provided in an oral dosage form and administration schedule for the treatment of a complement mediated disorder which provides a minimum mean plasma concentration ($C_{trough}$) during treatment of between about 50 and 200 ng/ml. In some embodiments, Compound 1 is provided in a dosage form and administration schedule which provides a minimum mean plasma concentration ($C_{trough}$) during treatment of between about 70 ng/mL and 170 ng/mL. In some embodiments, Compound 1 is provided in a dosage form and administration schedule which provides a minimum mean plasma concentration ($C_{trough}$) during treatment of between about 75 ng/mL and 160 ng/mL. In some embodiments, the $C_{trough}$ is at least about 50 ng/ml, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, or at least about 150 ng/mL. In one embodiment, the $C_{trough}$ is at least about 100 ng/mL. In some embodiments, the $C_{trough}$ is less than about 170 ng/ml, less than about 150 ng/ml, less than about 125 ng/mL, less than about 115 ng/mL, less than about 110 ng/mL, less than about 105 ng/mL, less than about 100 ng/mL, less than about 95 ng/mL, or less than about 90 ng/mL. It has been found that maintaining a $C_{trough}$ concentration of about 50 ng/mL provides, 85% AP inhibition at that concentration, while a $C_{trough}$ of about 67-88 ng/mL provides greater than 90% AP inhibition. In some embodiments, Compound 1 is provided in a dosage form and administration schedule which provides, during the course of the treatment, a $C_{trough}$ concentration of between about 50 ng/mL and about 200 ng/mL and a maximum mean plasma concentration ($C_{max}$) that is less than about 1000 ng/ml. In some embodiments, Compound 1 is provided in a dosage form and administration schedule which provides, during the course of the treatment, a $C_{trough}$ concentration of between about 70 ng/mL and about 170 ng/mL and a maximum mean plasma concentration ($C_{max}$) that is less than about 1000 ng/ml. In some embodiments, Compound 1 is provided in a dosage form and administration schedule which provides, during the course of the treatment, a $C_{trough}$ concentration of about 100 ng/mL and a $C_{max}$ that is less than about 1000 ng/ml. In some embodiments, Compound 1 is provided in a dosage form and administration schedule which provides, during the course of the treatment, a $C_{trough}$ concentration of less than about 125 ng/mL and a maximum mean plasma concentration ($C_{max}$) that is less than about 1000 ng/ml. In some embodiments, Compound 1 is provided in a dosage form and administration schedule which provides, during the course of the treatment, a $C_{trough}$ concentration of less than about 150 ng/mL and a maximum mean plasma concentration ($C_{max}$) that is less than about 1000 ng/ml. In some embodiments, Compound 1 is provided in a dosage form and administration schedule which provides, during the course of the treatment, a $C_{trough}$ concentration of less than about 175 ng/mL and a maximum mean plasma concentration ($C_{max}$) that is less than about 1000 ng/ml. In one embodiment, Compound 1 is administered in a dosage form of 120 mg BID. In one embodiment, the complement mediated disorder is PNH. In one embodiment, the complement mediated disorder is 3CG or IC-MPGN.

In one aspect, Compound 1 is provided in an oral dosage form and administration schedule for the treatment of a complement mediated disorder which provides a minimum mean plasma concentration ($C_{trough}$) during treatment of between about 225 and 450 ng/ml. In some embodiments, Compound 1 is provided in a dosage form and administration schedule which provides a minimum mean plasma concentration ($C_{trough}$) during treatment of between about 240 ng/mL and 400 ng/mL. In some embodiments, the $C_{trough}$ is at least about 225 ng/ml, at least about 250 ng/mL, at least about 275 ng/mL, at least about 300 ng/mL, at least about 325 ng/mL, at least about 350 ng/mL, at least about 375 ng/mL, at least about 400 ng/mL, at least about 425 ng/mL, or at least about 450 ng/mL. In one embodiment, the $C_{trough}$ is at least about 300 ng/mL. In some embodiments, the $C_{trough}$ is less than about 450 ng/ml, less than about 425 ng/ml, less than about 400 ng/mL, less than about 375 ng/mL, less than about 350 ng/mL, less than about 325 ng/mL, less than about 300 ng/mL, less than about 275 ng/mL, or less than about 250 ng/mL. In some embodiments, Compound 1 is provided in a dosage form and administration schedule which provides, during the course of the treatment, a $C_{trough}$ concentration of between about 225 ng/mL and about 450 ng/mL and a maximum mean plasma concentration ($C_{max}$) that is less than about 2000 ng/ml. In some embodiments, Compound 1 is provided in a dosage form and administration schedule which provides, during the course of the treatment, a $C_{trough}$ concentration of between about 240 ng/mL and about 400 ng/mL and a maximum mean plasma concentration ($C_{max}$) that is less than about 2000 ng/ml. In some embodiments, Compound 1 is provided in a dosage form and administration schedule which provides, during the course of the treatment, a $C_{trough}$ concentration of about 320 ng/mL and a $C_{max}$ that is less than about 2000 ng/ml. In some embodiments, Compound 1 is provided in a dosage form and administration schedule which provides, during the course of the treatment, a $C_{trough}$ concentration of less than about 400 ng/mL and a maximum mean plasma concentration ($C_{max}$) that is less than about 2000 ng/ml. In one embodiment, Compound 1 is administered at 200 mg BID. In one embodiment, the complement mediated disorder is PNH. In one embodiment, the complement mediated disorder is 3CG or IC-MPGN.

In one aspect, Compound 1 is administered at a particular dosage as described herein. In some embodiments, Compound 1 is administered so that a single dose provides a specific PK blood profile as described herein. In some embodiments, the dose administered to the subject is between about 25 mg to about 275 mg. In some embodiments, the dosage administered is between about 40 mg to about 160 mg. In some embodiments, the dosage administered is at least about 40 mg, at least about 50 mg, at least about 60 mg, at least about 75 mg, at least about 90 mg, at least about 100 mg, at least about 125 mg, at least about 150 mg, at least about 160 mg, at least about 170 mg, at least about 175 mg, at least about 180 mg, at least about 190 mg, at least about 200 mg, at least about 210 mg, at least about 220 mg, at least about 230 mg, at least about 240 mg, at least about 250 mg, at least about 260 mg, or at least about 275 mg. In some embodiments, Compound 1 is administered as a 120 mg dose twice a day during treatment. In some embodiments, Compound 1 is administered as a 150 mg dose twice a day during treatment. In some embodiments, Compound 1 is administered as a 175 mg dose twice a day during treatment. In some embodiments, Compound 1 is administered as a 200 mg dose twice a day during treatment. In some embodiments, Compound 1 is administered as a 220 mg dose twice a day during treatment. In some embodiments, Compound 1 is administered as a 240 mg dose twice a day during treatment. In some embodiments, Compound 1 is administered as a 240 mg dose once a day during treatment.

Accordingly, certain embodiments provided herein include, but are not limited to:
A) A BID oral dosage form comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a lower of two different diurnal $C_{trough}$ levels in human plasma of between about 65 ng/mL and 95 ng/mL.
B) A BID oral dosage form comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a lower of two different diurnal $C_{trough}$ levels in human plasma of about 90 ng/mL+/−10%.

C) An oral dosage form comprising an effective amount to reduce alternative complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a $C_{trough}$ level in human plasma of between about 65 ng/mL and 95 ng/mL.

D) An oral dosage form comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a $C_{trough}$ level in human plasma of about 90 ng/mL+/−10%.

E) A BID oral dosage form comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a lower of two different diurnal $C_{trough}$ levels in human plasma of at least 65 ng/mL.

F) An oral dosage form comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a human plasma $C_{trough}$ in a human of at least 65 ng/mL.

G) A BID oral dosage form comprising an effective amount to reduce complement D pathway activity (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a lower of two different diurnal $C_{trough}$ levels in human plasma of about 100 ng/mL+/−10%.

H) An oral dosage regimen comprising an effective amount to reduce complement D pathway activity of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), or a pharmaceutically acceptable salt thereof, that provides a $C_{trough}$ in human plasma of at least 100 ng/mL+/−10%.

I) The oral dosage regimen of any of A) to H) above, wherein the dosage form comprises between about 100 mg and 200 mg.

J) The oral dosage of I) above, which comprises about 120 mg.

K) The oral dosage of claim I) above, which comprises about 200 mg.

L) The oral dosage form of any of A) to K) above, wherein the $C_{trough}$ level in human plasma is measured in a patient with paroxysmal nocturnal hemoglobinuria (PNH).

M) The oral dosage form of any of A) to K) above, wherein the $C_{trough}$ level in human plasma is measured in a patient with a disorder selected from fatty liver, such as nonalcoholic steatohepatitis (NASH), liver inflammation, cirrhosis, or liver failure.

N) The oral dosage form of any of A) to K) above, wherein the $C_{trough}$ level in human plasma is measured in a patient with a disorder selected from amyotrophic lateral sclerosis; rheumatoid arthritis, a complement alternative pathway (AP)-associated nephropathy, a component 3 glomerulopathy (C3G) disorder, C3 glomerulonephritis (C3GN), dense deposit disease (DDD), a membranoproliferative glomerulonephritis (MPGN) and immune-complex membranoproliferative glomerulonephritis (IC-MPGN).

O) The oral dosage form of any of A) to K) above, wherein the $C_{trough}$ level in human plasma is measured in a patient with a disorder selected from amyotrophic lateral sclerosis; rheumatoid arthritis, a complement alternative pathway (AP)-associated nephropathy, and glomerulopathy.

P) The oral dosage form of any of A) to K) above, wherein the $C_{trough}$ level in human plasma is measured in a patient with a disorder selected from age-related macular degeneration (AMD), retinal degeneration, ophthalmic disease, geographic atrophy, early or neovascular age-related macular degeneration, autoimmune dry eye diseases and environmental dry eye disease.

Q) A method for treating a patient with a complement D related disorder comprising administering an effective amount of the oral dosage form of any of A) to K) above.

R) The method of Q) above, wherein the patient has paroxysmal nocturnal hemoglobinuria (PNH).

S) The method of Q) above, wherein the patient has a disorder selected from fatty liver, such as nonalcoholic steatohepatitis (NASH), liver inflammation, cirrhosis, or liver failure.

T) The method of Q) above, wherein the patient has a disorder selected from amyotrophic lateral sclerosis; rheumatoid arthritis, a complement alternative pathway (AP)-associated nephropathy, a component 3 glomerulopathy (C3G) disorder, C3 glomerulonephritis (C3GN), dense deposit disease (DDD), a membranoproliferative glomerulonephritis (MPGN) and immune-complex membranoproliferative glomerulonephritis (IC-MPGN).

U) The method of Q) above, wherein the patient has a disorder selected from amyotrophic lateral sclerosis; rheumatoid arthritis, a complement alternative pathway (AP)-associated nephropathy, and glomerulopathy.

V) The method of Q) above, wherein the patient has a disorder selected from age-related macular degeneration (AMD), retinal degeneration, ophthalmic disease, geographic atrophy, early or neovascular age-related macular degeneration, autoimmune dry eye disease and environmental dry eye disease.

W) The method of any of Q) to V) above, wherein the dosage form is administered for one month of longer.

X) The method of any of Q) to V) above, wherein the dosage form is administered for at least six months.

Y) The oral dosage form of any of A) to K) above, which provides a $C_{max}$ of less than about 2000 ng/mL.

Z) The oral dosage form of any of A) to K) above, which provides a $C_{max}$ of less than about 1000 ng/mL.

AA) The oral dosage form of any of A) to K) above, for use to treat a patient with a complement D related disorder.

BB) A method for the manufacture of a medicament to treat a patient with a complement D related disorder comprising preparing an oral dosage form of any of A) to K) above.

CC) The oral dosage form of BB) above for use to treat any of the disorders listed in any of R) to V) above.

DD) The method of CC) above, to treat any of the disorders listed in R) to V) above.

DETAILED DESCRIPTION

Figure 1:
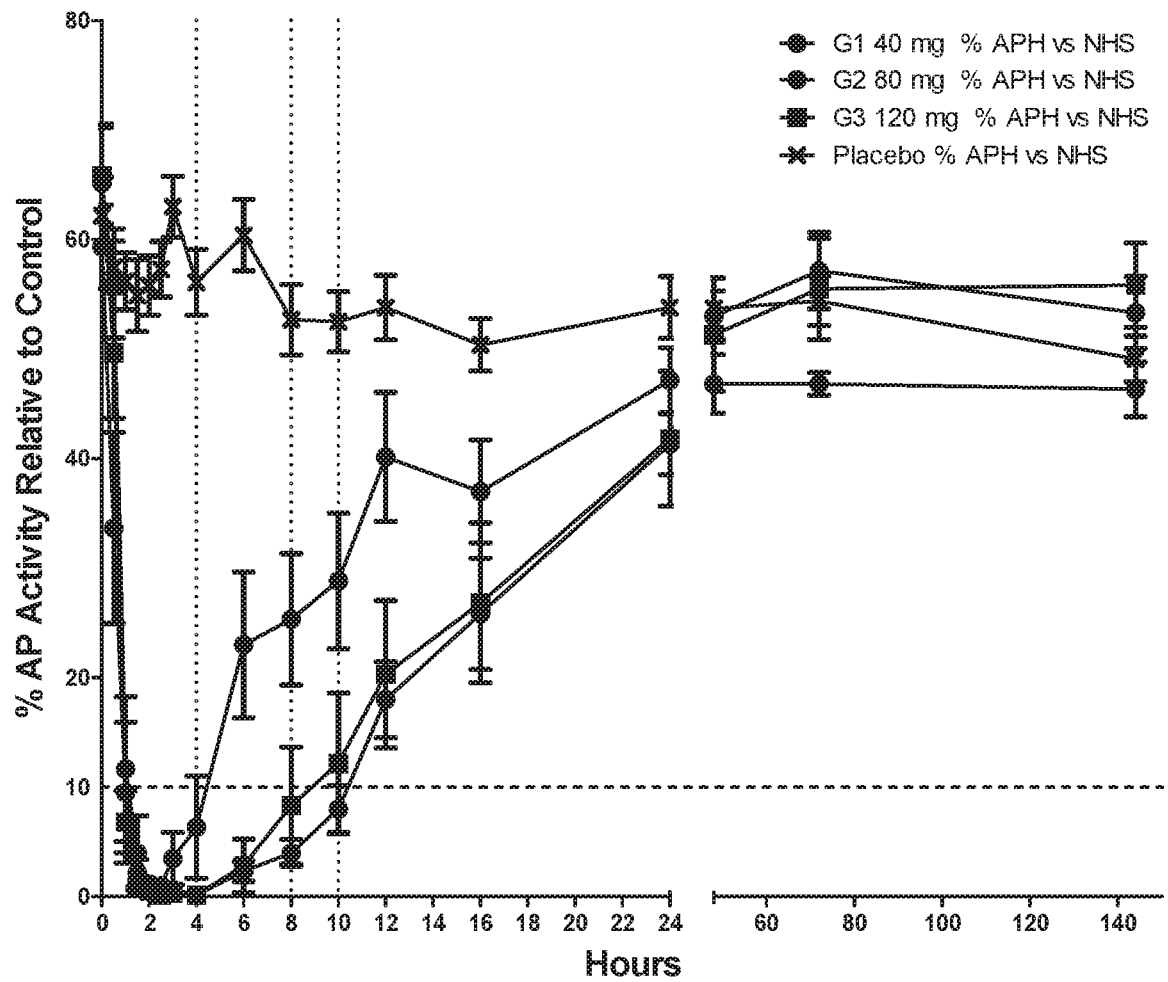
FIG. 1 is a graph representing the percent AP activity measured by AP hemolysis after single doses of 40, 80, and 120 mg Compound 1, or Placebo. Groups 1 through 3 were administered Compound 1 as a single dose on Day 1 Hour 0. The y-axis represents the % inhibition of AP activity relative to control. The x-axis represents time from first administration of Compound 1.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. It has been discovered that at an oral dosage of Compound 1 of about 100 mg to 200 mg twice a day, more specifically about 120 mg to 180 mg twice a day, and even more specifically about 120 mg to 150 mg twice a day, or about 150 mg to about 200 mg twice a day, and in one embodiment about 120 mg twice a day, provides an optimal minimum mean plasma concentration ($C_{trough}$) at the end of the dosage interval such that the dosage does not fall below its $EC_{90}$ effectiveness at any time during the day. Specifically, a dosage regimen was discovered that maintains the lower of the two diurnal minimum mean plasma concentrations ($C_{trough}$) above the established $EC_{90}$. Modeling, as described further below, established an $EC_{90}$ of between 67-88 ng/mL will provide about 90% AP activity inhibition. The administration of Compound 1 in the dosing profiles described herein results in the potent inhibition of AP activity, greater than 85% inhibition at a $C_{trough}$ of just 65 ng/mL to 95 ng/mL. Specifically, the invention includes oral dosage forms, for example solid dosage forms or liquid gel-based dosage forms, comprising Compound 1, having the structure:

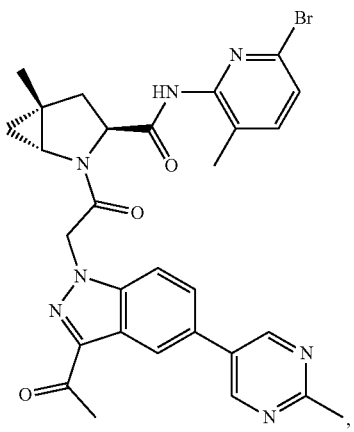 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)cc12]

or a pharmaceutically acceptable composition, salt, isotopic analog, or prodrug thereof, to a subject, preferably a human, for the treatment of a disorder mediated by dysfunction of or excessive activation of complement ("a complement-mediated disorder") so that a specific PK and/or PD blood profile described herein is attained. It has been discovered that dosing a human subject with Compound 1 to a mean blood plasma concentration level of about 65 ng/mL to 95 ng/mL provides potent inhibition of the AP. Methods of making Compound 1 are described in PCT Publication No.: 2017/035353, incorporated herein by reference.

Definitions

"AUC" (Amount*time/volume) as used herein means the area under the plasma concentration-time curve.

"$AUC_{(0-inf)}$" (Amount*time/volume) as used herein means the area under the plasma concentration-time curve from time zero to infinity.

"$AUC_{(0-24)}$" (Amount*time/volume) as used herein means the area under the plasma concentration time curve from time zero to 24 hours after dosing.

"AUEC" as used herein means the area under the pharmacodynamic (PD) effect curve.

"$AUEC_{0-12}$" as used herein means the AUEC from 0 hr. through 12 hr.

"% $AUEC_{0-12}$" as used herein means $AUEC_{0-12}$ as a percent of its maximum value.

"$A_{405}$" as used herein means Optical Absorbance at 405 nM.

"BID" as used herein means "bis en die" or twice daily.

"$C_{max}$" (Amount/volume) as used herein means the maximum (peak) plasma drug concentration.

"$C_{trough}$" (Amount/volume) as used herein means the mean plasma concentration at the end of the dosage interval or the minimum mean plasma concentration.

"CSR" as used herein means Clinical Study Report.

"$DURATION_{0-12}$" as used herein means the duration of pharmacodynamic (PD) effect from 0 hr. to 12 hr.

"$EC_{50}$ (or $EC_{90}$)" as used herein means 50% (or 90%) Effective Concentration.

"Minimum mean plasma concentration" as used herein means the $C_{trough}$.

"$t_{max}$" (Time) as used herein means time to reach maximum (peak) plasma concentration following drug administration.

"% CV" as used herein means Coefficient of Variation.

"AP" as used herein means alternative complement pathway.

"Bb" as used herein means Bb fragment of complement Factor B.

"ELISA" as used herein means Enzyme-linked immunosorbent assay.

"FD" as used herein means Complement Factor D.

"MAD" as used herein means Multiple Ascending Dose.

"N" as used herein means total number of patients.

"PD" as used herein means pharmacodynamic.

"PK" as used herein means pharmacokinetic.

"SAD" as used herein means single ascending dose.

"SD" as used herein means standard deviation.

The term "carrier" applied to pharmaceutical compositions/combinations of the invention refers to a diluent, excipient, or vehicle with which Compound I is provided.

A "dosage form" means a unit of administration of an active agent. Examples of dosage forms include tablets, capsules, suspensions, liquids, emulsions, particles, spheres, buccal, sublingual, gel, mucosal, and the like.

A "patient" or "host" or "subject" is a human or non-human animal in need of treatment or prevention of any of the disorders as specifically described herein, including but not limited to by modulation of the complement Factor D pathway. Typically the host is a human. A "patient" or "host"

or "subject" also refers to for example, a mammal, primate (e.g., human), cows, sheep, goat, horse, dog, cat, rabbit, rat, mice, fish, bird and the like.

The term "pharmaceutically acceptable salt" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salt" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable excipient" means an excipient that is useful in preparing a pharmaceutical composition/combination that is generally safe, non-toxic and neither biologically nor otherwise inappropriate for administration to a host, typically a human. In some embodiments, an excipient is used that is acceptable for veterinary use.

Throughout the specification and claims, a given chemical formula or name shall encompass all optical and stereoisomers, as well as racemic mixtures where such isomers and mixtures exist, unless otherwise noted.

In the description below and herein generally, whenever any of the terms referring to Compound 1 are used, it should be understood that pharmaceutically acceptable salts or compositions are considered included, unless otherwise stated or inconsistent with the text.

As contemplated herein and for purposes of the disclosed ranges herein, all ranges described herein include any and all numerical values occurring within the identified ranges. For example, a range of 1 to 10, or between 1 and 10, as contemplated herein, would include the numerical values 1, 2, 3, 4, 5, 6, 7, 8, 9, 10, as well as fractions thereof.

Dosage forms of (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide The invention provides particular dosage forms which provide blood profile ranges of the complement factor D (fD) inhibitor (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (Compound 1), and methods using said dosage forms for treating a subject having a complement-mediated disorder.

In one aspect, Compound 1 is administered to a subject having a complement-mediated disorder so that a single dose of Compound 1 provides a specific PK and/or PD blood profile as described herein. In some embodiments, Compound 1 is administered so that a minimum mean plasma concentration ($C_{trough}$) of from about 50 ng/mL to about 200 ng/mL is maintained above the lower $C_{trough}$ level in the diurnal cycle of a BID dosing regimen during treatment. In some embodiments, Compound 1 is administered so that a minimum mean plasma concentration ($C_{trough}$) of from about 75 ng/mL to about 125 ng/mL is maintained above the lower $C_{trough}$ level in the diurnal cycle of a BID dosing regimen during treatment. In some embodiments the $C_{trough}$ is at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, at least about 160 ng/mL, at least about 165 ng/mL, at least about 170 ng/mL, at least about 175 ng/mL, at least about 180 ng/mL, at least about 185 ng/mL, at least about 190 ng/mL, at least about 195 ng/mL, or at least about 200 ng/mL. In some embodiments, Compound 1 is administered so that a minimum mean plasma concentration ($C_{trough}$) of less than about 150 ng/mL is maintained above the lower $C_{trough}$ level in the diurnal cycle of a BID dosing regimen during treatment. In some embodiments the $C_{trough}$ is less than about 50 ng/mL, less than about 55 ng/mL, less than about 60 ng/mL, less than about 65 ng/mL, less than about 70 ng/mL, less than about 75 ng/mL, less than about 80 ng/mL, less than about 85 ng/mL, less than about 90 ng/mL, less than about 95 ng/mL, less than about 100 ng/mL, less than about 110 ng/mL, less than about 120 ng/mL, less than about 130 ng/mL, less than about 140 ng/mL, less than about 150 ng/mL, less than about 160 ng/mL, less than about 175 ng/mL, less than about 190 ng/mL, or less than about 200 ng/mL. In some embodiments, Compound 1 is administered so that a $C_{trough}$ of at least about 125 ng/mL is maintained above the lower $C_{trough}$ level in the diurnal cycle of a BID dosing regimen during treatment. In some embodiments, Compound 1 is administered so that a $C_{trough}$ of at least about 100 ng/mL is maintained above the lower $C_{trough}$ level in the diurnal cycle of a BID dosing regimen during treatment. In some embodiments, Compound 1 is administered so that a $C_{trough}$ of at least about 85 ng/mL is maintained above the lower $C_{trough}$ level in the diurnal cycle of a BID dosing regimen during treatment. In some embodiments, Compound 1 is administered so that a $C_{trough}$ of at least about 67 ng/mL is maintained above the lower $C_{trough}$ level in the diurnal cycle of a BID dosing regimen during treatment. In some embodiments, Compound 1 is administered so that a $C_{trough}$ of at least about 50 ng/mL is maintained above the lower $C_{trough}$ level in the diurnal cycle of a BID dosing regimen during treatment. In some embodiments, Compound 1 is administered so that a $C_{trough}$ of at least 50 ng/mL+/−10% is maintained above the lower $C_{trough}$ level in the diurnal cycle of a BID dosing regimen during treatment. In some embodiments, Compound 1 is administered so that a $C_{trough}$ of at least 67 ng/mL+/−10% is maintained above the lower $C_{trough}$ level in the diurnal cycle of a BID dosing regimen during treatment. In some embodiments, Compound 1 is administered so that a $C_{trough}$ of at least 85 ng/mL+/−10% is maintained above the lower $C_{trough}$ level in the diurnal cycle of a BID dosing regimen during treatment. In some embodiments, Compound 1 is administered so that a $C_{trough}$ of 100 ng/mL+/−10% is maintained above the lower $C_{trough}$ level in the diurnal cycle of a BID dosing regimen during treatment. It has been found that maintaining a $C_{trough}$ concentration of about 50 ng/mL provides >85% AP inhibition, and a $C_{trough}$ of about 88 ng/mL provides >90% AP inhibition.

In one aspect, Compound 1 is provided in a dosage form, for example in an oral dosage form such as a solid dosage form or liquid gel-based dosage form, which provides a maximum mean plasma concentration ($C_{max}$). In some embodiments, Compound 1 is provided in a dosage form that provides a maximum mean plasma concentration ($C_{max}$) of between 300 ng/mL is at least about 3000 ng/mL. In some embodiments, the $C_{max}$ is at least about 300 ng/mL, is at least about 325 ng/mL, is at least about 350 ng/mL, is at least about 375 ng/mL, is at least about 400 ng/mL, is at least about 425 ng/mL, is at least about 450 ng/mL, is at least about 475 ng/mL, is at least about 500 ng/mL, is at least about 525 ng/mL, is at least about 550 ng/mL, is at least about 575 ng/mL, is at least about 600 ng/mL, is at least about 625 ng/mL, is at least about 650 ng/mL, is at least about 675 ng/mL, is at least about 700 ng/mL, is at least about 725 ng/mL, is at least about 750 ng/mL, is at least about 775 ng/mL, is at least about 800 ng/mL, is at least about 825 ng/mL, is at least about 850 ng/mL, is at least about 875 ng/mL, is at least about 900 ng/mL, is at least about 925 ng/mL, is at least about 950 ng/mL, is at least about 975 ng/mL, is at least about 1000 ng/mL, is at least about 1150 ng/mL, is at least about 1200 ng/mL, is at least about 1250 ng/mL, is at least about 1300 ng/mL, is at least about 1350 ng/mL, is at least about 1400 ng/mL, is at least about 1450 ng/mL, is at least about 1500 ng/mL, is at least about 1550 ng/mL, is at least about 1600 ng/mL, is at least about 1650 ng/mL, is at least about 1700 ng/mL, is at least about 1750 ng/mL, is at least about 1800 ng/mL, is at least about 1850 ng/mL, is at least about 1900 ng/mL, is at least about 1950 ng/mL, is at least about 2000 ng/mL, is at least about 2050 ng/mL, is at least about 2100 ng/mL, is at least about 2150 ng/mL, is at least about 2200 ng/mL, is at least about 2250 ng/mL, is at least about 2300 ng/mL, is at least about 2350 ng/mL, is at least about 2400 ng/mL, is at least about 2450 ng/mL, is at least about 2500 ng/mL, is at least about 2550 ng/mL, is at least about 2600 ng/mL, is at least about 2650 ng/mL, is at least about 2700 ng/mL, is at least about 2750 ng/mL, is at least about 2800 ng/mL, is at least about 2850 ng/mL, is at least about 2900 ng/mL, is at least about 2950 ng/mL, or is at least about 3000 ng/mL. In some embodiments, the $C_{max}$ is less than about 2500 ng/mL. In some embodiments, the $C_{max}$ is less than about 2000 ng/mL. In some embodiments, the $C_{max}$ is less than about 1500 ng/mL. In some embodiments, the $C_{max}$ is less than about 1000 ng/mL. In some embodiments, the $C_{max}$ is less than about 500 ng/mL. In some embodiments, the $C_{max}$ is less than about 2500 ng/mL+/−10%. In some embodiments, the $C_{max}$ is less than about 2000 ng/mL+/−10%. In some embodiments, the $C_{max}$ is less than about 1500 ng/mL+/−10%. In some embodiments, the $C_{max}$ is less than about 1000 ng/mL+/−10%. In some embodiments, the $C_{max}$ is less than about 500 ng/mL+/−10%.

In one aspect, Compound 1 is provided in a dosage form, for example in an oral dosage form such as a solid dosage form or liquid gel-based dosage form, which provides an $AUC_{(0-24)}$ as described herein. In some embodiments, Compound 1 is provided in a dosage form that provides an $AUC_{(0-24)}$ of between about 6000 ng*hr/mL to about 20000 ng*hr/mL. In some embodiments, Compound 1 is provided in a dosage form providing an $AUC_{(0-24)}$ of is at least about 6000 ng*hr/mL, is at least about 6500 ng*hr/mL, is at least about 7000 ng*hr/mL, is at least about 7500 ng*hr/mL, is at least about 8000 ng*hr/mL, is at least about 8500 ng*hr/mL, is at least about 9000 ng*hr/mL, is at least about 9500 ng*hr/mL, is at least about 10000 ng*hr/mL, is at least about 10500 ng*hr/mL, is at least about 11000 ng*hr/mL, is at least about 11500 ng*hr/mL, is at least about 12000 ng*hr/mL, is at least about 12500 ng*hr/mL, is at least about 13000 ng*hr/mL, is at least about 13500 ng*hr/mL, is at least about 14000 ng*hr/mL, is at least about 14500 ng*hr/mL, is at least about 15000 ng*hr/mL, is at least about 15500 ng*hr/mL, is at least about 16000 ng*hr/mL, is at least about 16500 ng*hr/mL, is at least about 17000 ng*hr/mL, is at least about 17500 ng*hr/mL, is at least about 18000 ng*hr/mL, is at least about 18500 ng*hr/mL, is at least about 19000 ng*hr/mL, is at least about 19500 ng*hr/mL, or is at least about 20000 ng*hr/mL. In some embodiments, the $AUC_{(0-24)}$ is at least about 1450 ng*hr/mL. In some embodiments, the $AUC_{(0-24)}$ is less than about 8000 ng*hr/mL. In some embodiments, the $AUC_{(0-24)}$ is at least about 8000 ng*hr/mL+/−10%. In some embodiments, the $AUC_{(0-24)}$ is less than about 8000 ng*hr/mL+/−10%.

Two additional measures of pharmacodynamic activity were calculated for each sampled 12-hour dosing interval: $Duration_{(0-12)}$ and $AUEC_{(0-12)}$ (Area Under the Effect Curve). $Duration_{(0-12)}$ represents the time during a 12-hour dosing interval over which AP inhibition was 90% or greater; a maximum value of 12 hours indicates 90% or more inhibition continuously through the interval. $AUEC_{(0-12)}$ represents the integrated magnitude of AP inhibition over time during the interval. Further, % $AUEC_{(0-12)}$ expresses $AUEC_{(0-12)}$ as a percent of the maximal AP inhibition over the interval (100% inhibition×12 hours).

In one aspect, Compound 1 is provided in a dosage form, for example in an oral dosage form such as a solid dosage form or liquid filled capsule or gel-based dosage form, which provides a time of maximum plasma concentration $Duration_{(0-12)}$ as described herein. In one aspect, Compound 1 is administered to a subject having a complement-mediated disorder resulting in a minimum mean $Duration_{(0-12)}$ of between 10 and 12 hours. In some embodiments Compound 1 is provided in a dosage form that provides a $Duration_{(0-12)}$ of at least about 10 hrs, at least about 10.25 hrs, at least about 10.5 hrs, at least about 10.75 hrs, at least about 11 hrs, at least about 11.25 hrs, at least about 11.5 hrs, at least about 11.75 hrs, at least about 12 hrs. In some embodiments, Compound 1 is provided in a dosage form that provides a $Duration_{(0-12)}$ of at least about 12 hrs.

In one aspect, Compound 1 is provided in a dosage form, for example in an oral dosage form such as a solid dosage form or liquid filled capsule or gel-based dosage form, which provides a time of maximum plasma concentration % $AUEC_{(0-12)}$ as described herein. In one aspect, Compound 1 is administered to a subject having a complement-mediated disorder resulting in a minimum mean % $AUEC_{(0-12)}$ of between 80% and 100%. In one aspect, Compound 1 is administered to a subject having a complement-mediated disorder resulting in a minimum mean % $AUEC_{(0-12)}$ of between 90% and 100%. In some embodiments Compound 1 is provided in a dosage form that provides a % $AUEC_{(0-12)}$ of at least about 80%, at least about 85%, at least about 90%, at least about 95%, or at least about 100%.

In one aspect, Compound 1 is provided in a dosage form, for example in an oral dosage form such as a solid dosage form or liquid filled capsule or gel-based dosage form, which provides a time of maximum plasma concentration ($t_{max}$) as described herein. In some embodiments, Compound 1 is provided in a dosage form that provides a $t_{max}$ of between about 0.5 hr and 3 hr. In some embodiments Compound 1 is provided in a dosage form that provides a $t_{max}$ of at least about 3 hrs, at least about 2.75 hrs, at least about 2.5 hrs, at least about 2.25 hrs, at least about 2.0 hrs, at least about 1.75 hrs, at least about 1.5 hrs, at least about 1.25 hrs, at least about 1 hr, at least about 0.75 hrs, or at least about 0.5 hrs. In some embodiments, Compound 1 is provided in a dosage form that provides a $t_{max}$ of at least about 2 hrs. In some embodiments, Compound 1 is provided in a dosage form that provides a $t_{max}$ of at least about 1 hr.

In some embodiments, Compound 1 is administered so that a single dose provides a specific PK and/or PD blood profile as described herein. In some embodiments, the dose administered to the subject is between about 25 mg to about 275 mg. In some embodiments, the dosage administered is at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 210 mg, at least about 220 mg, at least about 230 mg, at least about 240 mg, at least about 250 mg, at least about 260 mg, at least about 270 mg, or at least about 275 mg. In some embodiments, Compound 1 is administered in a single dose of at least about 120 mg. In some embodiments, Compound 1 is administered in a single dose of at least about 240 mg. In some embodiments, Compound 1 is administered in a single dose of 120 mg+/−10%. In some embodiments, Compound 1 is administered once a day during treatment. In some embodiments, Compound 1 is administered twice a day during treatment (BID). In some embodiments, Compound 1 is administered at least twice a day during treatment. In some embodiments, Compound 1 is administered three or more times during treatment. In some embodiments, Compound 1 is administered in a single dose of at least about 120 mg twice a day. In some embodiments, Compound 1 is administered in a single dose of at least about 150 mg twice a day. In some embodiments, Compound 1 is administered in a single dose of at least about 175 mg twice a day. In some embodiments, Compound 1 is administered in a single dose of at least about 200 mg twice a day. In some embodiments, Compound 1 is administered in a single dose of at least about 210 mg twice a day. In some embodiments, Compound 1 is administered in a single dose of at least about 225 mg twice a day. In some embodiments, Compound 1 is administered in a single dose of at least about 250 mg twice a day. In some embodiments, Compound 1 is administered twice a day, with each dose spaced approximately 12 hours apart. In some embodiments, Compound 1 is administered two times a day, with each dose spaced about 12 hours apart, for 28 days. In some embodiments, Compound 1 is administered two times a day for at least about 4 weeks, at least about 5 weeks, at least about 6 weeks, or at least about 12 weeks. In some embodiments, Compound 1 is administered two times a day for at least about 3 months, at least about 6 months, or at least about 9 months.

Pharmaceutical Preparations

Compound 1 can be administered as the neat chemical. Alternatively, Compound 1 can be administered as a pharmaceutical composition, that includes an effective amount for a host, typically a human, in need of such treatment of Compound 1, as described herein. Accordingly, the disclosure provides neat and pharmaceutical compositions comprising a dosage form of Compound 1 in an amount of compound or pharmaceutically acceptable salt together with at least one pharmaceutically acceptable carrier to achieve the blood profile ranges described herein. The pharmaceutical composition may contain a compound or salt as the only active agent, or, in an alternative embodiment, the compound and at least one additional active agent. The pharmaceutical composition may also include a molar ratio of the active compound and an additional active agent.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with Compound 1 is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from at least about 25 wt. % to at least about 50 wt. % or from at least about 5 wt. % to at least about 75 wt. % of the compound.

Methods of Treatment

As contemplated herein, a dosage form providing PK and/or PD blood profiles as described herein can be used to treat a complement-mediated disorder. By attaining and/or maintaining certain blood profiles as described herein, the alternative complement pathway can be inhibited, providing a dosing regimen useful to treat disorders that are the result of defective or overactive complement reactions.

In some embodiments, Compound 1 is administered so that a minimum mean plasma concentration ($C_{trough}$) of from about 50 ng/mL to about 200 ng/mL is maintained above the lower $C_{trough}$ level in the diurnal cycle of a BID dosing regimen during treatment. In some embodiments, Compound 1 is administered so that a minimum mean plasma concentration ($C_{trough}$) of from about 75 ng/mL to about 125 ng/mL is maintained above the lower $C_{trough}$ level in the diurnal cycle of a BID dosing regimen during treatment. In some embodiments, Compound 1 is administered so that a $C_{trough}$ of at least about 50 ng/mL is maintained above the lower $C_{trough}$ level in the diurnal cycle of a BID dosing regimen during treatment. In some embodiments, Compound 1 is administered so that a $C_{trough}$ of about 67 ng/mL is maintained above the lower $C_{trough}$ level in the diurnal cycle of a BID dosing regimen during treatment. In some embodiments, Compound 1 is administered so that a $C_{trough}$ of about 85 ng/mL is maintained above the lower $C_{trough}$ level in the diurnal cycle of a BID dosing regimen during treatment. In some embodiments, Compound 1 is administered so that a $C_{trough}$ of about 100 ng/mL is maintained above the lower $C_{trough}$ level in the diurnal cycle of a BID dosing regimen during treatment. In some embodiments, Compound 1 is administered so that a $C_{trough}$ of about 125 ng/mL is maintained above the lower $C_{trough}$ level in the diurnal cycle of a BID dosing regimen during treatment. In some embodiments, Compound 1 is administered so that a $C_{trough}$ of at least 50 ng/mL+/−10% is maintained above the lower $C_{trough}$ level in the diurnal cycle of a BID dosing regimen during treatment. In some embodiments, Compound 1 is administered so that a $C_{trough}$ of at least 67 ng/mL+/−10% is maintained above the lower $C_{trough}$ level in the diurnal cycle of a BID dosing regimen during treatment. In some embodiments, Compound 1 is administered so that a $C_{trough}$ of at least 85 ng/mL+/−10% is maintained above the lower $C_{trough}$ level in the diurnal cycle of a BID dosing regimen during treatment. In some embodiments, Compound 1 is administered so that a $C_{trough}$ of at least 100 ng/mL+/−10% is maintained above the lower $C_{trough}$ level in the diurnal cycle of a BID dosing regimen during treatment. In some embodiments, Compound 1 is administered so that a $C_{trough}$ of at least 125 ng/mL+/−10% is maintained above the lower $C_{trough}$ level in the diurnal cycle of a BID dosing regimen during treatment. In some embodiments, Compound 1 is administered so that a $C_{trough}$ of 50 ng/mL+/−10% is maintained above the lower $C_{trough}$ level in the diurnal cycle of a BID dosing regimen during treatment. In some embodiments, Compound 1 is administered so that a $C_{trough}$ of 67 ng/mL+/−10% is maintained above the lower $C_{trough}$ level in the diurnal cycle of a BID dosing regimen during treatment. In some embodiments, Compound 1 is administered so that a $C_{trough}$ of 85 ng/mL+/−10% is maintained above the lower $C_{trough}$ level in the diurnal cycle of a BID dosing regimen during treatment. In some embodiments, Compound 1 is administered so that a $C_{trough}$ of 100 ng/mL+/−10% is maintained above the lower $C_{trough}$ level in the diurnal cycle of a BID dosing regimen during treatment.

In some embodiments, Compound 1 is administered so that a $Duration_{(0-12)}$ of between about 10 and about 12 hours is attained during treatment. In some embodiments, Compound 1 is administered so that a $Duration_{(0-12)}$ of between about 11 and about 12 hours is attained during treatment. In some embodiments, Compound 1 is administered so that a $Duration_{(0-12)}$ of at least 10 hours is attained during treatment. In some embodiments, Compound 1 is administered so that a $Duration_{(0-12)}$ of at least 11 hours is attained during treatment. In some embodiments, Compound 1 is administered so that a $Duration_{(0-12)}$ of at least 12 hours is attained during treatment.

In some embodiments, Compound 1 is administered so that a % $AEUC_{(0-12)}$ of between about 80% and about 100% is attained during treatment. In some embodiments, Compound 1 is administered so that a % $AEUC_{(0-12)}$ of between about 90% and about 100% is attained during treatment. In some embodiments, Compound 1 is administered so that a % $AEUC_{(0-12)}$ of at least 80% is attained during treatment. In some embodiments, Compound 1 is administered so that a % $AEUC_{(0-12)}$ of at least 90% is attained during treatment. In some embodiments, Compound 1 is administered so that a % $AEUC_{(0-12)}$ of at least 100% is attained during treatment.

In some embodiments, Compound 1 is administered so that a $C_{max}$ of less than about 3000 ng/mL is attained during treatment. In some embodiments, Compound 1 is administered so that a $C_{max}$ of less than about 2000 ng/mL is attained during treatment. In some embodiments, Compound 1 is administered so that a $C_{max}$ of less than about 1000 ng/mL is attained during treatment. In some embodiments, Compound 1 is administered so that a $C_{max}$ of between about 600 ng/mL and about 1700 ng/mL is attained during treatment. In some embodiments, Compound 1 is administered so that a $C_{max}$ of less than 3000 ng/mL+/−10% is attained during treatment. In some embodiments, Compound 1 is administered so that a $C_{max}$ of less than 2000 ng/mL+/−10% is attained during treatment. In some embodiments, Compound 1 is administered so that a $C_{max}$ of less than 1000 ng/mL+/−10% is attained during treatment. In some embodiments, Compound 1 is administered so that a $C_{max}$ of less than 600 ng/mL+/−10% is attained during treatment. In some embodiments, Compound 1 is administered so that a $C_{max}$ of between 800 ng/mL+/−10% and 1500 ng/mL+/−10% is attained during treatment.

In some embodiments, Compound 1 is administered so that an $AUC_{(0-24)}$ of between about 6000 ng*hr/mL and 20000 ng*hr/mL is attained during treatment. In some embodiments, Compound 1 is administered so that an $AUC_{(0-24)}$ of at least about 6000 ng*hr/mL is attained during treatment.

In some embodiments, a method for the treatment of a disorder associated with a dysfunction in the complement cascade in a host is provided that includes the administration that includes administering Compound 1 to achieve a specific PK and/or PD blood profile as described herein. In some embodiments, a method of inhibiting activation of the alternative complement pathway in a subject is provided that includes the administration of that includes administering Compound 1 to achieve a specific PK and/or PD blood profile as described herein. In some embodiments, a method of modulating Factor D activity in a subject is provided that includes the administration of an that includes administering Compound 1 to achieve a specific PK and/or PD blood profile as described herein.

In some embodiments, the disorder is paroxysmal nocturnal hemoglobinuria (PNH). In one aspect, Compound 1 is administered to a subject having PNH in an amount sufficient wherein lactate dehydrogenase (LDH) levels, a biomarker of intravascular hemolysis, are reduced from a baseline LDH level measured prior to administration by at least about 30%, at least about 40%, at least about 50%, at least about 60%, at least about 70%, at least about 80%, or greater than 80% from baseline during the course of treatment. In one aspect, Compound 1 is administered to a subject having PNH in an amount sufficient wherein hemoglobin levels are increased from a baseline level measured prior to administration by at least about 10%, at least about 15%, at least about 20%, at least about 25%, or greater than 25% from baseline during the course of treatment.

In some embodiments, the disorder is membranoproliferative glomerulonephritis (MPGN). MPGN is a disease that affects the glomeruli, or filters, of the kidneys. Until recently, membranoproliferative glomerulonephritis (MPGN) was clinically classified as either primary, idiopathic MPGN or as secondary MPGN when an underlying aetiology was identifiable. Primary MPGN was further classified into three types-type I, type II, and type III-based principally on the ultrastructural appearance and location of electron-dense deposits. Both the clinical and histopathologic schemes presented problems, however, as neither was based on disease pathogenesis. An improved understanding of the role of complement in the pathogenesis of MPGN has led to a proposed reclassification into immunoglobulin-mediated disease (driven by the classical complement pathway) and non-immunoglobulin-mediated disease (driven by the alternative complement pathway). This reclassification has led to improved diagnostic clinical algorithms and the emergence of a new grouping of diseases known as the C3 glomerulopathies, best represented by dense deposit disease (DDD) and C3 glomerulonephritis (C3GN).

In some embodiments, the disorder is C3 glomerulopathy. C3 glomerulopathy is a group of related conditions that cause the kidneys to malfunction. The major features of C3 glomerulopathy include high levels of protein in the urine (proteinuria), blood in the urine (hematuria), reduced amounts of urine, low levels of protein in the blood, and swelling in many areas of the body. Affected individuals may have particularly low levels of complement component 3 (or C3) in the blood. The kidney problems associated with C3 glomerulopathy tend to worsen over time. About half of affected individuals develop end-stage renal disease (ESRD) within 10 years after their diagnosis. ESRD is a life-threatening condition that prevents the kidneys from filtering fluids and waste products from the body effectively.

In some embodiments, the disease is dense deposit disease (DDD). In some embodiments, the disease is C3 glomerulonephritis (C3GN).

In some embodiments, the disease is immune-complex membranoproliferative glomerulonephritis (IC-MPGN)). IC-MPGN is a renal disease which shares many clinical, pathological, genetic and laboratory features with C3G. Up to 40% of patients with IC-MPGN have no identifiable underlying etiology, and are considered to have idiopathic IC-MPGN. Subjects with idiopathic IC-MPGN can have low C3 and normal C4 levels, similar to those observed in C3G, as well as many of the same genetic or acquired factors that are associated with abnormal alternative pathway activity. Those subjects with a low C3 and a normal C4 are likely to have significant over-activity of the alternative pathway. The presence of C3Nef is identified as frequently in patients with MPGN type 1 as those with C3GN. Mutations in genes encoding alternative pathway proteins including fH and fI are found in IC-MPGN patients. Despite immunopositive fluorescence staining for IgG, IgM, and C1q (in a fraction of cases) in kidney biopsy, approximately 46% of the IC-MPGN cases exhibit reduced C3 levels and normal C4.

These data demonstrate that the alternative pathway is dysregulated in IC-MPGN In some embodiments, Compound 1 is administered so that the LDH level decreases from a level greater than or equal to 1.5× the upper limit of normal (ULN) during treatment. In some embodiments, Compound 1 is administered so that the Hgb level increases during treatment.

Additional disorders that may be treated or prevented by Compound 1 or its salt or composition as described herein also include, but are not limited to:

(i) abdominal aortic aneurysm, hemodialysis complications, hemolytic anemia, or hemodialysis, neuromylitis (NMO), fatty liver, nonalcoholic steatohepatitis (NASH), liver inflammation, cirrhosis, liver failure, dermatomyocitis, amyotrophic lateral sclerosis, age-related macular degeneration (AMD), rheumatoid arthritis, and cytokine or inflammatory reactions in response to biotherapeutics (e.g. CAR T-cell therapy), paroxysmal nocturnal hemoglobinuria (PNH), hereditary angioedema, capillary leak syndrome, atypical hemolytic uremic syndrome (aHUS), hemolytic uremic syndrome (HUS), abdominal aortic aneurysm, hemodialysis complications, hemolytic anemia, or hemodialysis;

(ii) myasthenia gravis (MG), multiple sclerosis, neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;

(iii) inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), Crohn's disease, rheumatoid arthritis, inflammatory bowel disease, lupus nephritides, arthritis, immune complex disorders and autoimmune diseases, systemic lupus, or lupus erythematosus;

(iv) ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes;

(v) Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite;

(vi) asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

Combination Therapy

In some embodiments, Compound 1 may be provided in combination or alternation with at least one additional therapeutic agent, for example, for treatment of a disorder listed herein. In some embodiments, Compound 1 may be administered to achieve a specific PK and/or PD blood profile as described herein in combination or alternation with at least one additional inhibitor of the complement system or a second active compound with a different biological mechanism of action, for example a C5 inhibitor, a C3 inhibitor, Complement Factor B inhibitor, or a pan-complement inhibitor.

C5 Inhibitors

C5 inhibitors are known in the art. In some embodiments, the C5 inhibitor is a monoclonal antibody targeting C5. In some embodiments, the C5 inhibitor is eculizumab (Soliris™ Alexion Pharmaceuticals, New Haven, CT, see, e.g., U.S. Pat. No. 9,352,035). In some embodiments, the C5 inhibitor is ravulizumab-cwvz (Ultomiris™ Alexion Pharmaceuticals, New Haven, CT.).

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (small animal protein, Volution Immuno-pharmaceuticals, Geneva, Switzerland; see e.g. Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883,158); ARC-1905 (pegylated RNA aptamer, Ophthotech, Princeton, NJ and New York, NY; see Keefe et al., Nature Reviews Drug Discovery, 9, 537-550); RA101348 and RA101495 (macrocyclic peptides, Ra Pharmaceuticals, Cambridge, MA); SOBI002 (affibody, Swedish Orphan Biovitrum, Stockholm, Sweden); ALN-CC5 (Si-RNA, Alnylam Pharmaceuticals, Cambridge, MA); ARC1005 (aptamers, Novo Nordisk, Bagsvaerd, Denmark); SOMAmers (aptamers, SomaLogic, Boulder, Co); SSL7 (bacterial protein toxin, see, e.g. Laursen et al. Proc. Natl. Acad. Sci. U.S.A., 107(8):3681-6); MEDI7814 (monoclonal antibody, MedImmune, Gaithersburg, MD); aurin tricarboxylic acid; aurin tricarboxylic acid derivatives (Aurin Biotech, Vancouver, BC, see U.S. Patent Appl. Pub. 2013/003592); RG6107 (anti-C5 recycling antibody, Roche Pharmaceuticals, Basel, Switzerland); ALXN1210 and ALXN5500 (monoclonal antibodies, Alexion Pharmaceuticals, New Haven, CT); TT30 (fusion protein, Alexion Pharmaceuticals, New Haven, CT); REGN3918 (monoclonal antibody, Regeneron, Tarrytown, NY); ABP959 (eculizumab biosimilar, Amgen, Thousand Oaks, CA); or combinations thereof.

In some embodiments, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In some embodiments, the C5 inhibitor is coversin. Coversin is a recombinant protein derived from a protein discovered in the saliva of the *Ornithodoros moubata* tick currently developed as a recombinant protein by Akari Therapeutics. Coversin is described in Penabad et al. Lupus 2012, 23(12):1324-6.

In some embodiments, the C5 inhibitor is Tesidolumab/LFG316. Tesidolumab is a monoclonal antibody developed by Novartis and Morphosys. Tesidolumab is described in U.S. Pat. Nos. 8,241,628 and 8,883,158.

In some embodiments, the C5 inhibitor is ARC-1905. ARC-1905 is a pegylated RNA aptamer developed by Ophthotech. ARC-1905 is described in Keefe et al. Nature Reviews Drug Discovery, 9:537-550.

In some embodiments, the C5 inhibitor is RA101348. RA101348 is a macrocyclic peptide developed by Ra Pharmaceuticals.

In some embodiments, the C5 inhibitor is RA101495. RA101495 is a macrocyclic peptide developed by Ra Pharmaceuticals.

In some embodiments, the C5 inhibitor is SOBI002. SOBI002 is an affibody developed by the Swedish Orphan Biovitrum.

In some embodiments, the C5 inhibitor is ARC1005. ARC1005 is an aptamer developed by Novo Nordisk.

In some embodiments, the C5 inhibitor is SOMAmers for C5. SOMAmers are aptamers developed by SomaLogic.

In some embodiments, the C5 inhibitor is SSL7. SSL7 is a bacterial protein toxin described in Laursen et al. Proc. Natl. Acad. Sci. U.S.A., 107(8):3681-6.

In some embodiments, the C5 inhibitor is MEDI7814. MEDI7814 is a monoclonal antibody developed by MedImmune.

In some embodiments, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In some embodiments, the C5 inhibitor is RG6107/SKY59. RG6107/SKY59 is an anti-C5 recycling antibody developed by Roche Pharmaceuticals.

In some embodiments, the C5 inhibitor is ALXN1210. In another embodiment, the C5 inhibitor is ALXN5500. ALXN1210 and ALXN5500 are monoclonal antibodies developed by Alexion Pharmaceuticals.

In some embodiments, the C5 inhibitor is TT30. TT30 is a fusion protein developed by Alexion Pharmaceuticals.

In some embodiments, the C5 inhibitor is ABP959. ABP959 is an eculizumab biosimilar monoclonal antibody developed by Amgen.

In some embodiments, the C5 inhibitor is Anti-C5 siRNA. Anti-C5 siRNA was developed by Alnylam Pharmaceuticals.

In some embodiments, the C5 inhibitor is Erdigna®. Erdigna® is an antibody developed by Adienne Pharma.

In some embodiments, the C5 inhibitor is avacincaptad pegol/Zimura®. Avacincaptad pegol is an aptamer developed by Opthotech.

In some embodiments, the C5 inhibitor is SOBI005. SOBI005 is a protein developed by the Swedish Orphan Biovitrum.

In some embodiments, the C5 inhibitor is ISU305. ISU305 is a monoclonal antibody developed by ISU ABXIS.

In some embodiments, the C5 inhibitor is REGN3918. REGN3918 is a monoclonal antibody developed by Regeneron.

C3 Inhibitors

Provided herein are methods for treating PNH in a subject comprising administering to the subject an effective amount of a C3 inhibitor in combination or alternation with an effective amount of a CFD inhibitor selected from Formula I or Formula II.

C3 inhibitors are known in the art. In some embodiments, Compound 1 is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9,371,365; 9,169,307; 8,946,145; 7,989,589; 7,888,323; 6,319,897; and US Patent Appl. Pub. Nos. 2016/0060297; 2016/0015810; 2016/0215022; 2016/0215020; 2016/0194359; 2014/0371133; 2014/0323407; 2014/0050739; 2013/0324482; and 2015/0158915. In yet another embodiment, the compstatin analog is 4(1MeW)POT-4. 4(1MeW)POT-4 was developed by Potentia. In yet another embodiment, the compstatin analog is AMY-201. AMY-201 was developed by Amyndas Pharmaceuticals.

In some embodiments, Compound 1 can be combined with C3 inhibitors that include, but are not limited to: H17 (monoclonal antibody, EluSys Therapeutics, Pine Brook, NJ); mirococept (CR1-based protein); sCRI (CR1-based protein, Celldex, Hampton, NJ); TT32 (CR-1 based protein, Alexion Pharmaceuticals, New Haven, CT); HC-1496 (recombinant peptide); CB 2782 (enzyme, Catalyst Biosciences, South San Francisco, CA); APL-2 (pegylated synthetic cyclic peptide, Apellis Pharmaceuticals, Crestwood, KY); or combinations thereof.

In some embodiments, the C3 inhibitor is H17. H17 is a humanized monoclonal antibody in development by EluSys Therapeutics. H17 is described in Paixao-Cavalcante et al. J. Immunol. 2014, 192(10):4844-4851.

In some embodiments, the C3 inhibitor is mirococept. Mirococept is a CR1-based protein developed by Inflazyme Pharmaceuticals.

In some embodiments, the C3 inhibitor is sCRI. sCRI is a soluble form of the CR1 protein developed by Celldex.

In some embodiments, the C3 inhibitor is TT32. TT32 is a CR-1 based protein developed by Alexion Pharmaceuticals.

In some embodiments, the C3 inhibitor is HC-1496. HC-1496 is a recombinant peptide developed by InCode.

In some embodiments, the C3 inhibitor is CB 2782. CB 2782 is novel protease derived from human membrane type serine protease 1 (MTSP-1) that was developed by Catalyst Biosciences.

In some embodiments, the C3 inhibitor is APL-2. APL-2 is a pegylated version of APL-1 developed by Apellis Pharmaceuticals.

Complement Factor B (CFB) Inhibitors

CFB inhibitors are known in the art. In some embodiments, Compound 1 can be combined with CFB inhibitors that include, but are not limited to: anti-FB SiRNA (Alnylam Pharmaceuticals, Cambridge, MA); TA106 (monoclonal antibody, Alexion Pharmaceuticals, New Haven, CT); LNPO23 (small molecule, Novartis, Basel, Switzerland); SOMAmers (aptamers, SomaLogic, Boulder, CO); bikaciomab (Novelmed Therapeutics, Cleveland, OH); complin (see, Kadam et al., J. Immunol. 2010, DOI:10.409/jimmunol.10000200); Ionis-FB-LRx (ligand conjugated antisense drug, Ionis Pharmaceuticals, Carlsbad, CA); or a combination thereof. In another embodiment, CFB inhibitors that can be combined with Compound 1 as described herein include those disclosed in PCT/US17/39587. In another embodiment, CFB inhibitors that can be combined with Compound 1 as described herein include those disclosed in PCT/US17/014458. In another embodiment, CFB inhibitors that can be combined with Compound 1 as described herein include those disclosed in U.S. Patent Appl. Pub. No. 2016/0024079 (assigned to Novartis AG). In some embodiments, the CFB inhibitor is

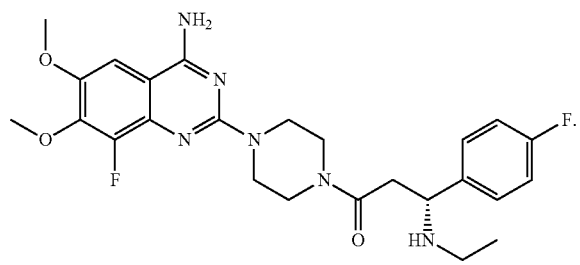 [SMILES: CCN[C@H](CC(=O)N1CCN(c2nc(N)c3cc(OC)c(OC)c(F)c3n2)CC1)c1ccc(F)cc1]

In some embodiments, the CFB inhibitor is anti-FB siRNA. Anti-FB siRNA was developed by Alnylam Pharmaceuticals.

In some embodiments, the CFB inhibitor is TA106. TA106 is a monoclonal antibody developed by Alexion Pharmaceuticals.

In some embodiments, the CFB inhibitor is LNP023. LNP023 is a small molecule inhibitor of CFB developed by Novartis. LNP023 and related inhibitors are described in Maibaum et al. Nat. Chem. Biol. 2016, 12:1105-1110.

In some embodiments, the CFB inhibitor is complin. Complin is a peptide inhibitor that is described in Kadam et al. J. Immunol. 2010 184(12):7116-24.

In some embodiments, the CFB inhibitor is Ionis-FB-LRx. Ionis-FB-LRx is a ligand conjugated antisense drug developed by Ionis Pharmaceuticals.

Pan-Inhibitors of Complement Components

Pan-inhibitors of complement components are known in the art. In some embodiments, the inhibitor is FUT-175.

EXAMPLES

Phase I Single Ascending Dose Study

A single ascending dose (SAD) study was the first-in-human study of Compound 1. The primary objective was to demonstrate the safety and tolerability of single ascending oral doses of Compound 1, an orally administered complement factor D inhibitor, in healthy volunteers. Secondary objectives included evaluation of the pharmacokinetic (PK) profile and the relationship between Compound 1 PK and pharmacodynamic (PD) characteristics, that is, the inhibition of complement alternative pathway (AP) activity (PK/PD).

Eighteen healthy volunteers were dosed and evaluated in 4 dose groups with ten subjects receiving placebo (Table 1). The first dose group had 6 active and 6 placebo subjects; subsequent groups had 6 active and 2 placebo subjects each. Each group was followed for 28 days after dosing. All subjects were monitored for safety through the last scheduled visit at Day 28. Blood and urine samples were collected at predefined time points from Days 1 to 4 to determine plasma and urine concentrations of Compound 1 and from Days 1 to 7 to determine complement related activities. Results of serum AP activity measured by AP Wieslab assay as well as plasma Bb, factor D level and several other PD biomarkers were determined.

TABLE 1

Dose Groups in ACH228-001 (SAD Study)

| Group | Dose (mg) | Regimen | Active (N) | Placebo (N) | Fasted vs Fed |
|---|---|---|---|---|---|
| 1 | 40 mg or PBO | Single Dose | 6 | 6 | Fasted |
| 2 | 80 mg or PBO | Single Dose | 6 | 2 | Fasted |
| 3 | 120 mg or PBO | Single Dose | 6 | 2 | Fasted |

PBO = placebo

Materials and Methods
Materials

Rabbit red blood cells (RBCs), gelatin veronal buffer without Ca++ and Mg++ (GVB0), and 100 mM MgCl2—100 mM EGTA (MgEGTA) were purchased from Complement Technology, Inc, (Tyler, TX). GVB0-MgEGTA buffer was prepared by mixing GVB0 and 100 mM MgEGTA at a 9:1 ratio. RBCs were used within two weeks of purchase; cells were collected each day prior to assay by centrifugation at 800×g and 4° C. for 3 min and resuspended in equal volume fresh cold GVB0·MgEGTA to a density of 5×10$^8$ cells/mL. Information of commercial ELISA kits used in this study is included in each specific assay below.

Human Serum/Plasma Preparation, Storage and Delivery

For human serum preparation, venous blood was collected by standard clinical procedures into a Gold Top, SST vacutainer (BD Vacutainer). After clotting at room temperature for 30 minutes or longer, the tube was centrifuged at ~1,300×g at 4° C. for 15 minutes to separate the serum from the clot. Serum was then aliquotted into pre-chilled cryovials (50-200 μl/vial) for storage at ~80° C. Each vial was thawed only once and used for each complement related assay, the remaining sample was discarded without further usage. For preparation of plasma, venous blood was collected into a Lavender Top, K2EDTA vacutainer and gently inverted several times to allow for complete mixing of the blood sample with the anticoagulant. The tube was placed in an ice-bath for 30 minutes and then centrifuged for 15 minutes at ~1300×g at 4° C. to separate the plasma from the blood cells. Plasma was divided into aliquots in pre-chilled cryogenic storage tubes and stored at a ~80° C. freezer within one hour of having collected the blood sample. For delivery, tubes containing either serum or plasma were shipped in the presence of dry ice without additional freeze-thaw cycle.

Serum AP Hemolysis Assay

Ex vivo serum AP hemolysis assays were conducted in 96-well microtiter plates divided into two parts, one for hemolysis and the other for serum background color subtraction. Briefly, a suspension of rabbit red blood cells (RBCs) was centrifuged at 800×g at 4° C. for 3 minutes and the supernatant was removed to get rid of the RBC debris. The RBC cell pellet was re-suspended gently with pre-chilled gelatin veronal buffer (GVB0) containing 10 mM MgEGTA to a density of 5×10$^8$ cells/mL. Other controls including buffer, spontaneous rabbit RBC lysis, 100% RBC lysis (in water), and normal serum control were set up alongside the test samples as well. Serum was placed in a 37° C. water-bath until mostly thawed and immediately transferred to ice bath. 20% serum was prepared with GVB0-MgEGTA buffer and kept at ice bath before testing. Reactions were carried out in a 96 well plate by mixing 50 μl of 20% serum with equal volume of GVB0-MgEGTA buffer and then quickly adding 20 μl of RBC suspension. The plate was shaken on a microtiter plate shaker for 5 seconds and then incubated at 37° C. for 30 minutes. Halfway during the incubation period, the plate was shaken for another 5 seconds as described above. At the end of the incubation, the plate was centrifuged at 800×g at 4° C. for 3 minutes to pellet the un-lysed rabbit RBCs. 80 μl of supernatant was removed carefully from all wells and transferred to a clear flat-bottom microtiter plate for the measurement of optical absorbance at 405 nm ($A_{405}$) in a Molecular Devices Spectramax Plus plate reader. AP hemolysis in each well was calculated relative to the activity of the NHS reference sample formulas as follows:

Hemolysis (%)=(($Hm$−$Bk$)−($Sp$−$Bf$))/(($NH$−BkNH)−($Sp$−$Bf$))×100% where Hm=$A_{405}$ in the hemolysis well, Bk=$A_{405}$ in the corresponding background well, Sp=mean $A_{405}$ in the spontaneous hemolysis wells, Bf=mean $A_{405}$ in the buffer alone wells, NH=mean $A_{405}$ in the reference NHS wells, and BkNH=mean $A_{405}$ in the corresponding background wells.

PK-PD Analysis

The PK-PD relationship was evaluated using time-matched plasma Compound 1 concentrations and serum AP inhibition values by non-linear regression with GraphPad Prism (La Jolla, CA) using the following two models:
1. The simple $E_{max}$ model to determine the 50% effective concentration ($EC_{50}$):

$Y=E_0+E_{max}\times X/(EC_{50}+X)$ where X=plasma Compound 1 concentration, Y=percent inhibition in the corresponding serum sample, $E_0$=0% inhibition (pre-dose AP activity), and $E_{max}$=100% inhibition.
2. The four-parameter sigmoidal model to determine $EC_{50}$ and the 90% effective concentration ($EC_{90}$):

$Y=E_0+(E_{max}-E_0)/(1+10^{((\log EC_{50}-X)\times HillSlope)})$ where X, Y, $E_0$, and $E_{max}$ are defined as above ($E_{max}$ model) and HillSlope=the slope factor or Hill slope.

Pharmacodynamic and Pharmacokinetic Results
AP Activity Measured with AP Hemolysis For all subjects, blood samples were collected at specific protocol-defined time points from Day 1 to 7 to determine serum AP activity ex vivo using AP hemolysis assay and AP Wieslab assay.

Figure 2:
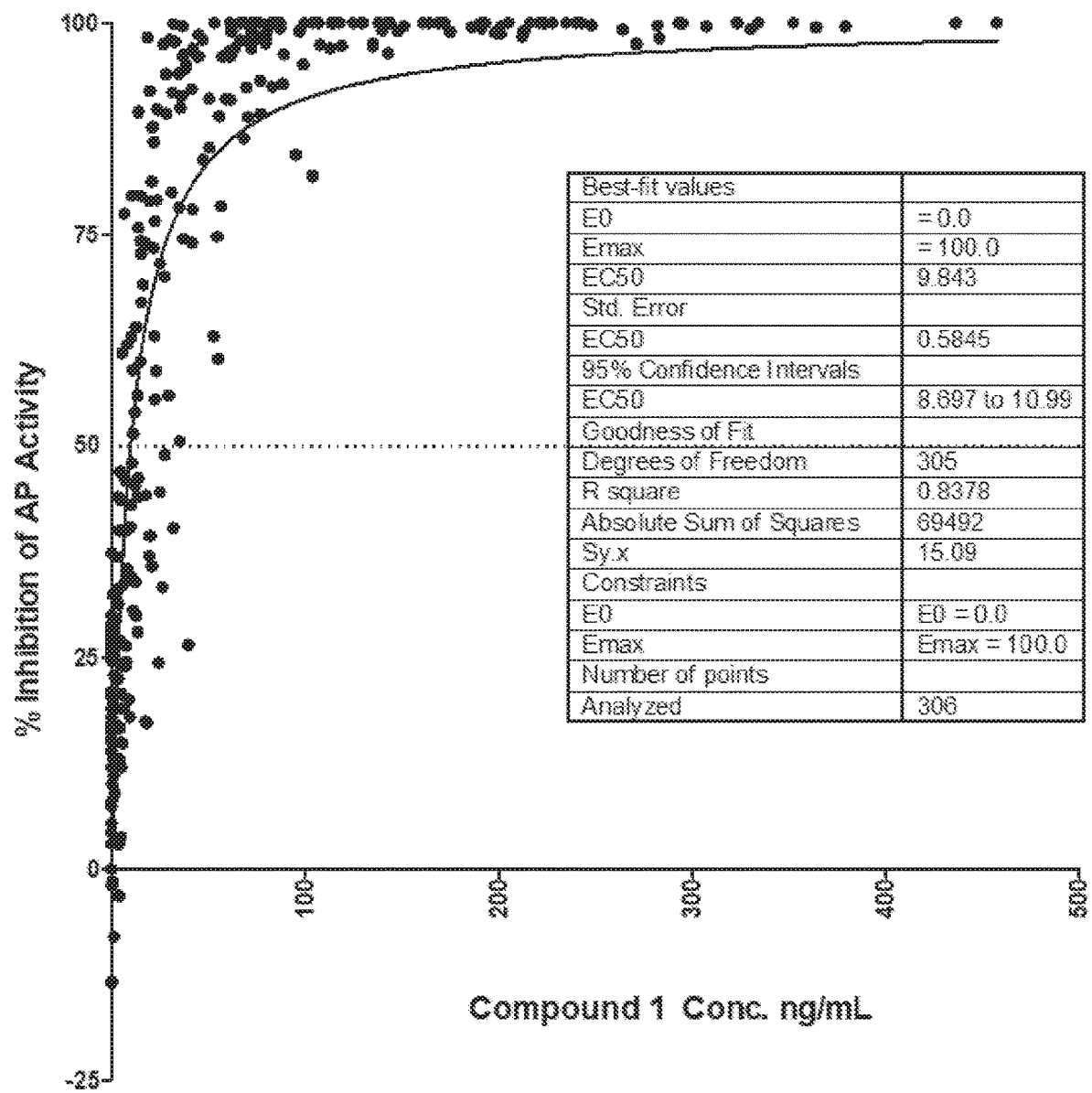
FIG. 2 is a graph representing PK-PD analysis of the relationship between plasma concentration of Compound 1 and inhibition of serum AP activity evaluated by AP hemolysis assay. The y-axis represents the percent inhibition of AP activity. The x-axis represents the plasma concentration of Compound 1.

Potent inhibition of AP activity was observed for all subjects administered a single dose of Compound 1 at 40, 80, or 120 mg (FIG. 1). Specifically, subjects in all groups achieved complete inhibition of the AP activity after Compound 1 dosing. In Group 1, approximately 90% or greater inhibition was maintained for at least 4 hours after dosing, based on the AP hemolysis assay. In Groups 2 and 3, approximately 90% or greater inhibition was maintained for at least 8 hours after dosing. In contrast, no significant change in AP activity was observed in placebo subjects (FIG. 1). The relationship between plasma Compound 1 concentration (PK) and serum AP activity as determined by the hemolysis assay for all subjects was analyzed using a simple $E_{max}$ model (FIG. 2). Based on this analysis, the $EC_{50}$ value of Compound 1 was 11.1 ng/mL.

Figure 3:
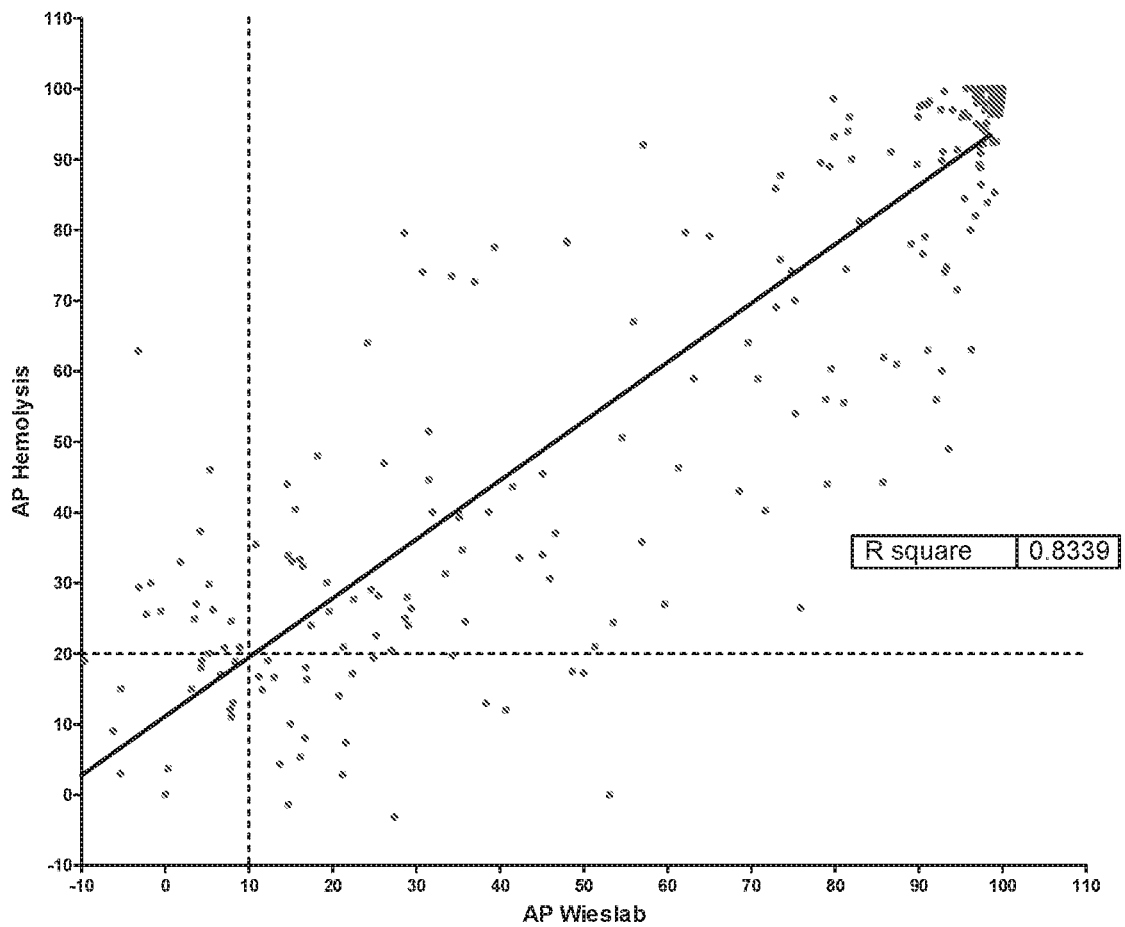
FIG. 3 is a graph representing the linear regression of the percent of AP activity between two endpoints.

In addition, AP activity in all serum samples measured by the AP hemolysis assay described herein were well correlated with AP Wieslab data (the correlation coefficient, r=0.83) for Compound 1-treated subjects and placebo subjects in Groups 3 (FIG. 3). The relationship between plasma Compound 1 concentration and serum AP inhibition by hemolysis assay was analyzed for all dosed subjects enrolled in the SAD study with the following simple $E_{max}$ dose-response model: $Y=E_0+E_{max} \cdot X/(EC_{50}+X)$ where $E_0$=uninhibited AP activity (0% inhibition) and $E_{max}$=fully inhibited AP activity (100%). Total sample number was 306. Serum samples were collected at specified time points following dosing and was assessed with both AP Wieslab and AP hemolysis assay for determination of AP activity. The AP activity at each time point was normalized to pre-dosing AP activity from the same subject (100%). The relationship between the two endpoints was analyzed by linear regression (Prism Software, GraphPad, La Jolla, CA).

For the 18 subjects comprising the Groups 1-3 SAD PK population, a total of 306 plasma samples (17 samples from each subject collected pre-dose and 0.5, 1, 1.5, 2, 2.5, 3, 4, 6, 8, 10, 12, 16, 24 [Day 2], 48 [Day 3], 72 [Day 4], and 144 [Day 7] hours post-dose) were available for PK determination in plasma.

Figure 4A:
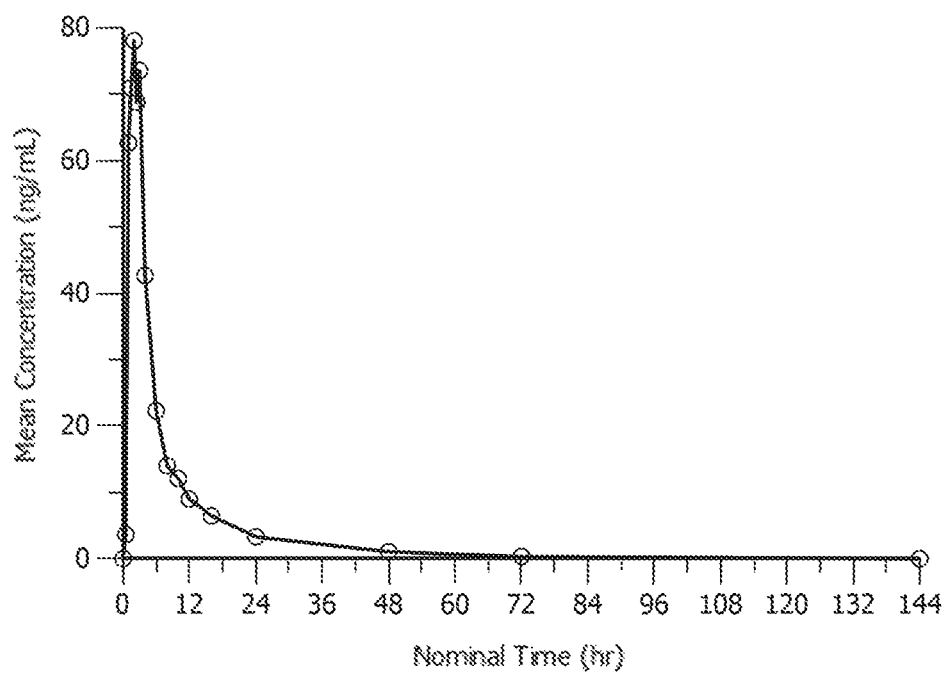
FIG. 4A and FIG. 4B are graphs representing mean plasma Compound 1 concentration-time profiles from 0 to 144 Hours (Day 7) (Linear [FIG. 4A] and Semi-Log [FIG. 4B] Scale) for the 40 mg Compound 1 dose.
Figure 4B:
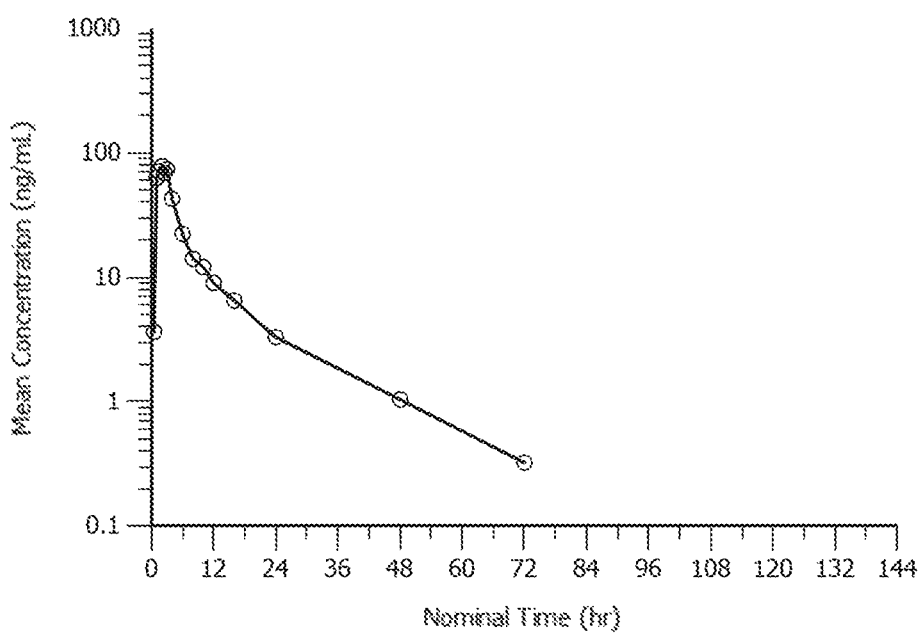
Figure 5A:
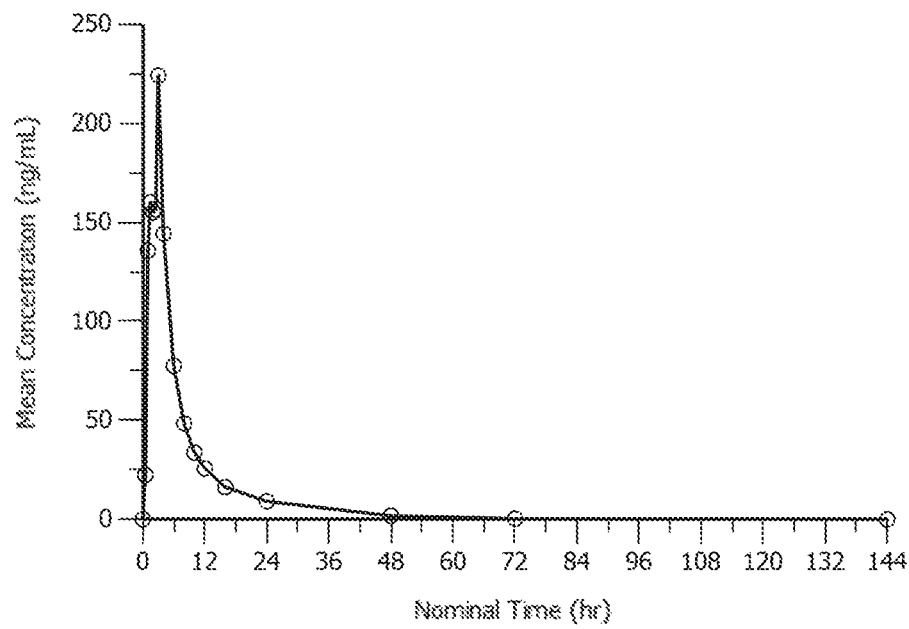
FIG. 5A and FIG. 5B are graphs representing mean plasma Compound 1 concentration-time profiles from 0 to 144 Hours (Day 7) (Linear [FIG. 5A] and Semi-Log [FIG. 5B] Scale) for the 80 mg Compound 1 dose.
Figure 5B:
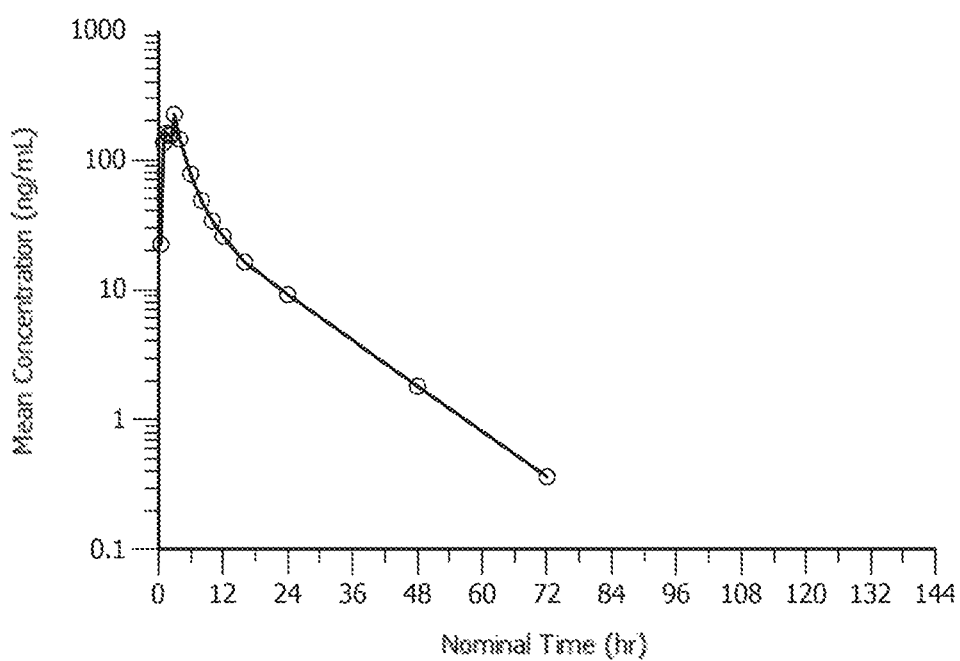
Figure 6A:
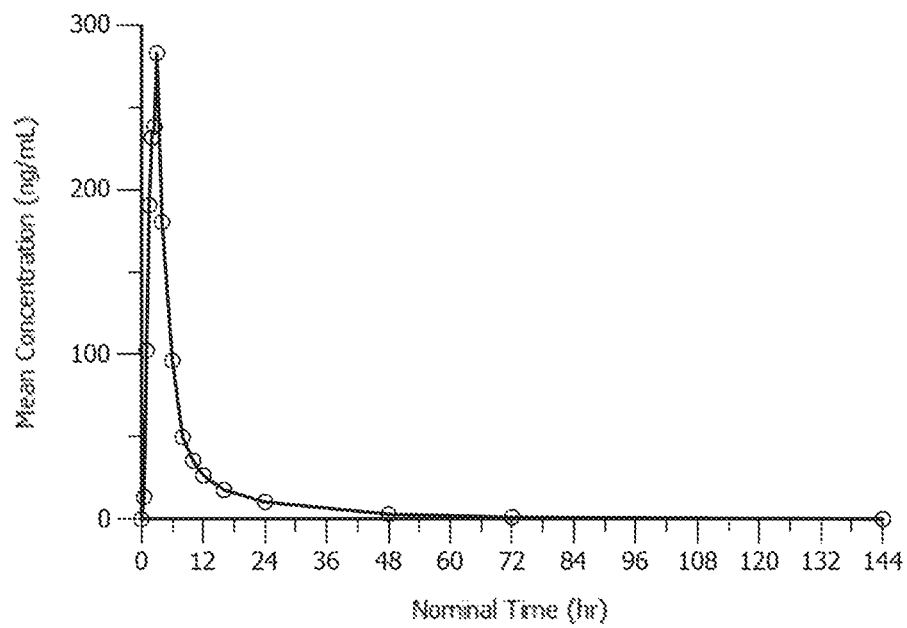
FIG. 6A and FIG. 6B are graphs representing mean plasma Compound 1 concentration-time profiles from 0 to 144 Hours (Day 7) (Linear [FIG. 6A] and Semi-Log [FIG. 6B] Scale) for the 120 mg Compound 1 dose.
Figure 6B:
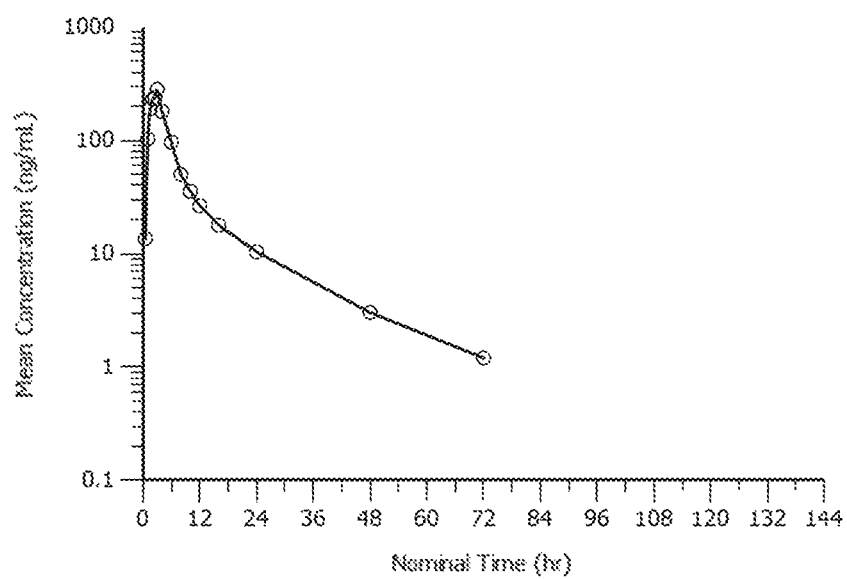

Concentrations of plasma Compound 1 prior to dosing were below the LLOQ (i.e., <0.100 ng/mL) in all 18 subjects comprising the PK population. Compound 1 was rapidly absorbed after dosing, with all 18 subjects having measurable plasma Compound 1 concentration at the first post-dose sampling time point evaluated (i.e., 0.5 hours post-dose). Plots of mean plasma Compound 1 concentration versus-time curves by randomized treatment group are presented in FIG. 4A (40 mg), FIG. 5A (80 mg), FIG. 6A (120 mg) (linear scale) and FIG. 4B (40 mg), FIG. 5B (80 mg), and FIG. 6B (120 mg) (semi-log scale), respectively, with summary statistics provided in Table 2. Maximum mean plasma concentrations (78.03±19.65 ng/mL in the 40 mg group, 224.05±108.27 ng/mL in the 80 mg group, and 282.83±89.15 ng/mL in the 120 mg group) occurred between 1 and 3 hours post-dose. Based on the mean concentration profiles, plasma Compound 1 concentrations appeared to increase in a dose-proportional manner following single dose administration of up to 120 mg. In all dose groups, plasma Compound 1 concentrations were last detected at the 72 hours post-dose time point.

Single ascending doses of Compound 1 were evaluated to determine plasma and urine PK parameters over the dose range of 40 mg to 120 mg studied. Summary statistics for plasma and urine Compound 1 concentration at each nominal sampling time point are presented by randomized treatment group in Table 2.

Plasma Compound 1 $C_{max}$ and AUCs increased proportionally with increasing dose (i.e., 40, 80, and 120 mg) of Compound 1 administered. In the 40 mg and 120 mg dose groups, variability in plasma Compound 1 PK parameters $C_{max}$ and AUC was generally low and similar, with geometric CV for $C_{max}$ of 30% (for the 40 mg group) or 31% (for the 120 mg group), and geometric CV for AUCs ranging from 23% to 32%. In the 80 mg dose group, there was considerably more variability in $C_{max}$ (geometric CV of 51%) and AUCs (geometric CV range from 50% to 53%) compared with the 40 mg and 120 mg dose groups. Rapid absorption of Compound 1 was observed with similar Median $t_{max}$ (1.50 hours to 2.75 hours) values over the dose range of 40 mg to 120 mg studied. Mean terminal elimination half-life ($t_{1/2\ term}$) values ranged from approximately 9.92 hours to 13.90 hours over the studied dose range.

Figure 7A:
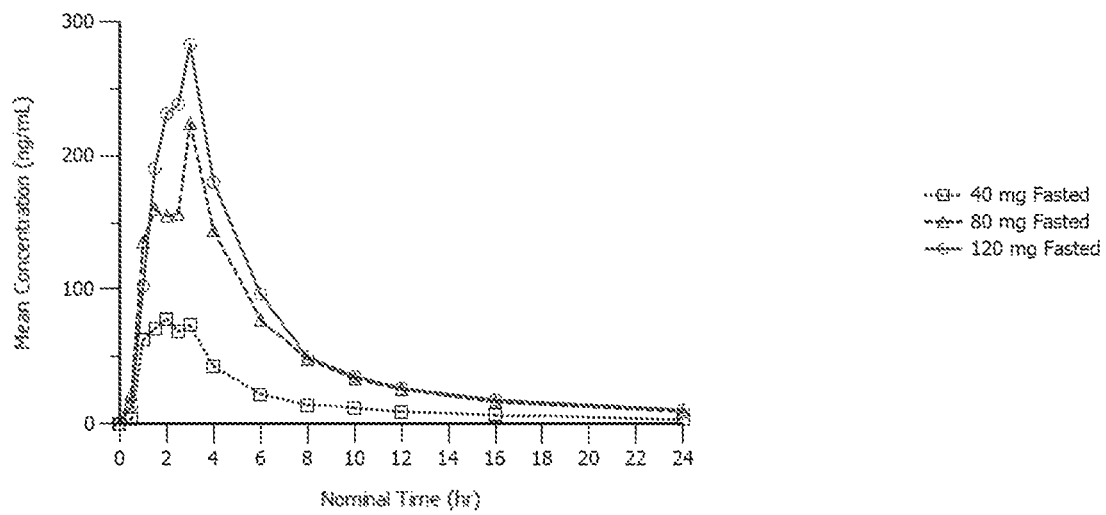
FIG. 7A and FIG. 7B are graphs representing mean plasma Compound I concentration-time profiles from 0 to 24 Hours (Linear Scale [FIG. 7A] and Semi-Log Scale [FIG. 7B]) for dose proportionality analysis.
Figure 7B:
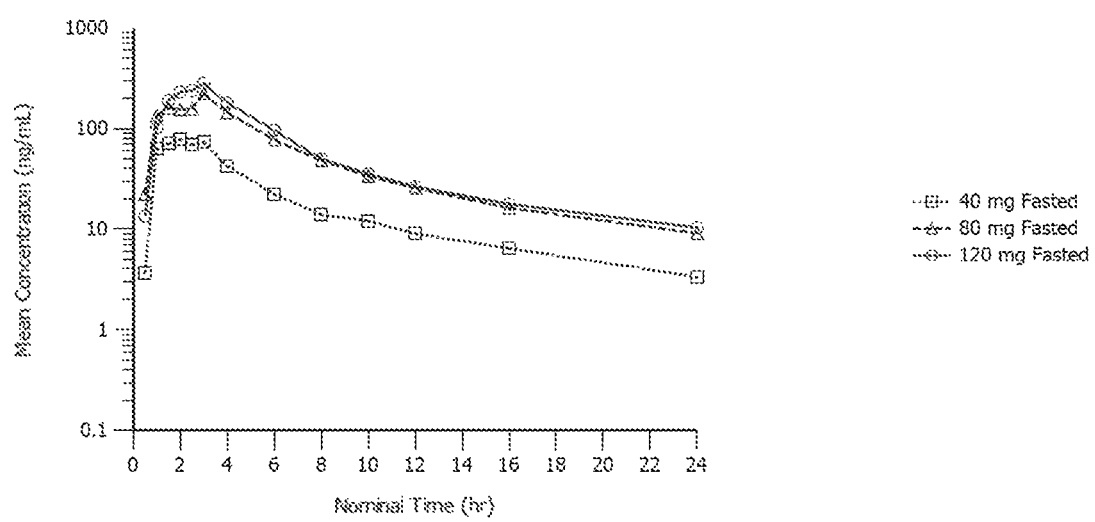

All subjects included in the PK population (n=18; 6 subjects each randomized to receive 40 mg, 80 mg, and 120 mg Compound 1) were included in the dose proportionality analysis. The geometric mean of $C_{max}$ and $AUC_{0-inf}$ values of plasma Compound 1 are presented in Table 2. Mean plasma Compound 1-versus-time profiles (from 0 to 24 hours) to assess dose proportionality are presented in FIG. 7A (linear scale) and FIG. 7B (semi-log scale).

Renal excretion of Compound 1 was low, with geometric mean dose recovered as unchanged Compound 1 ranging from 0.17% to 0.26% of the administered dose. Renal clearance values were also similar across dose groups, with geometric mean values ranging from 0.16 L/h to 0.19 L/h.

TABLE 2

Summary of Compound 1 Pharmacokinetic Parameter Estimates in Plasma and Urine

| Parameter (Unit) | Statistic | 40 mg ACH-5228 (Cohort 1) (N = 6) | 80 mg ACH-5228 (Cohort 2) (N = 6) | 120 mg ACH-5228 (Cohort 3) (N = 6) |
|---|---|---|---|---|
| | | Plasma | | |
| $t_{max}$ (h) | Mean (SD) | 1.75 (0.69) | 2.00 (0.84) | 2.58 (0.49) |
| | Median (Min, Max) | 1.50 (1.00, 3.00) | 1.75 (1.00, 3.00) | 2.75 (2.00, 3.00) |
| | GM (GCV %) | 1.65 (38) | 1.85 (45) | 2.54 (20) |
| $C_{max}$ (ng/mL) | Mean (SD) | 88.63 (28.78) | 253.17 (108.77) | 315.83 (102.01) |
| | Median (Min, Max) | 79.10 (62.00, 142.00) | 247.00 (113.00, 379.00) | 259.50 (240.00, 457.00) |
| | GM (GCV %) | 85.32 (30) | 231.81 (51) | 303.46 (31) |
| $t_{1/2\ term}$ (h) | Mean (SD) | 13.08 (4.61) | 9.92 (1.72) | 13.90 (7.06) |
| | GM (GCV %) | 12.51 (32) | 9.80 (16) | 12.67 (48) |
| $AUC_{0-inf}$ (h * ng/mL) | Mean (SD) | 513.93 (178.47) | 1,392.81 (681.02) | 1,709.13 (445.33) |
| | GM (GCV %) | 492.26 (32) | 1,259.35 (53) | 1,669.74 (23) |
| Vz/F (L) | Mean (SD) | 1,498.03 (344.21) | 991.97 (452.77) | 1,461.30 (802.51) |
| | GM (GCV %) | 1,466.83 (22) | 898.59 (54) | 1,313.43 (51) |
| CL/F (L/h) | Mean (SD) | 84.27 (22.79) | 70.25 (34.10) | 73.25 (14.13) |
| | GM (GCV %) | 81.26 (32) | 63.52 (53) | 71.87 (23) |

TABLE 2-continued

Summary of Compound 1 Pharmacokinetic Parameter Estimates in Plasma and Urine

| Parameter (Unit) | Statistic | Randomized Treatment Group | | |
|---|---|---|---|---|
| | | 40 mg ACH-5228 (Cohort 1) (N = 6) | 80 mg ACH-5228 (Cohort 2) (N = 6) | 120 mg ACH-5228 (Cohort 3) (N = 6) |
| Urine | | | | |
| $A_{eu}$ (mg) | Mean (SD) | 0.0749 (0.04) | 0.3058 (0.33) | 0.2913 (0.12) |
| | GM (GCV %) | 0.0671 (52) | 0.2045 (119) | 0.2683 (48) |
| $A_{eu(\%)}$ (%) | Mean (SD) | 0.19 (0.11) | 0.38 (0.41) | 0.24 (0.10) |
| | GM (GCV %) | 0.17 (52) | 0.26 (119) | 0.22 (48) |
| CLr (L/h) | Mean (SD) | 0.16 (0.05) | 0.21 (0.13) | 0.21 (0.11) |
| | GM (GCV %) | 0.16 (30) | 0.18 (66) | 0.19 (57) |

Abbreviations:
$A_{eu}$ = total amount of Compound I excreted in urine;
$A_{eu(\%)}$ = total amount of Compound I excreted in urine expressed as a percentage of dose;
$AUC_{0-12}$ = area under the plasma concentration-time curve from time of administration to 12 hours post-dose with a quantifiable concentration;
$AUC_{0-24}$ = area under the plasma concentration-time curve from time of administration to 24 hours post-dose with a quantifiable concentration;
$AUC_{0-inf}$ = area under the plasma concentration-time curve extrapolated to infinity;
$AUC_{last}$ = area under the plasma concentration-time curve from time of administration to the last time post-dose with a quantifiable concentration;
CL/F = apparent oral drug clearance;
$CL_r$ = renal clearance of total Compound I;
$C_{max}$ = maximum plasma concentration;
GCV % = geometric percent coefficient of variation;
GM = geometric mean;
h = hour;
L = liter;
mL = milliliter;
ng = nanogram;
SD = standard deviation;
$t^{1/2}_{term}$ = apparent terminal elimination half-life;
$t_{max}$ = time to reach the maximum plasma concentration;
$V_z/F$ = apparent volume of distribution;
$\lambda z$ = terminal elimination rate constant.

Alternative Pathway Functional Activity by AP Wieslab Assay

Figure 8A:
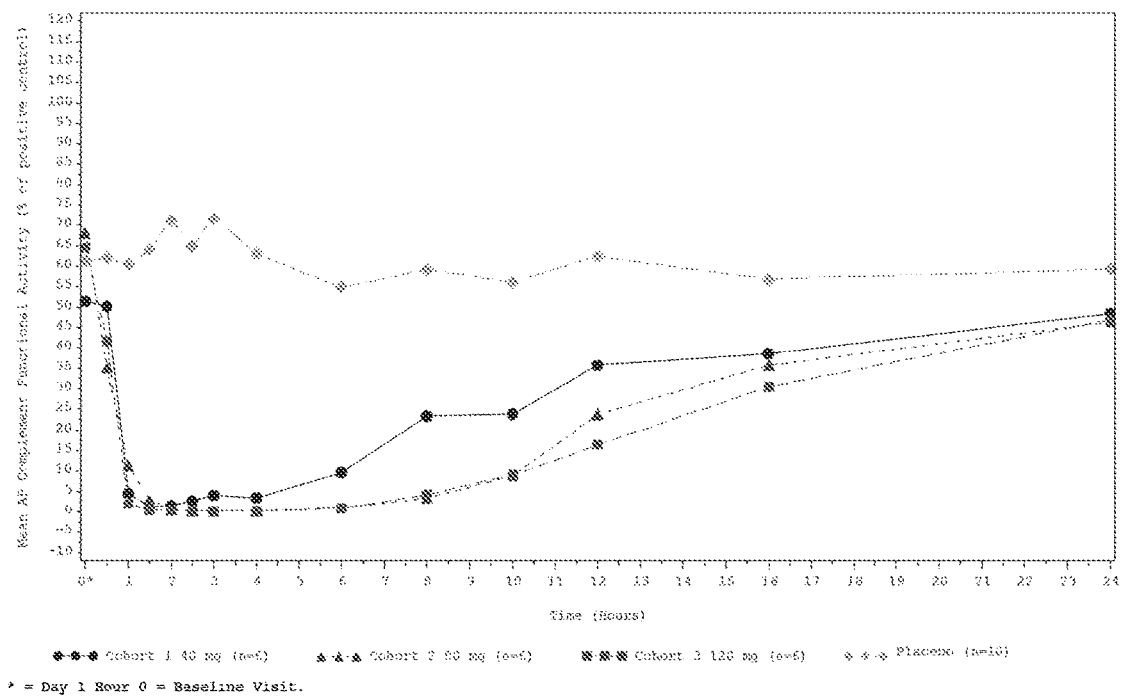
FIG. 8A and FIG. 8B are graphs representing mean alternative pathway functional activity (% relative to positive control) within 24 Hours of dosing (FIG. 8A) and over time (FIG. 8B) by randomized treatment group assessed by the AP Wieslab Assay.
Figure 8B:
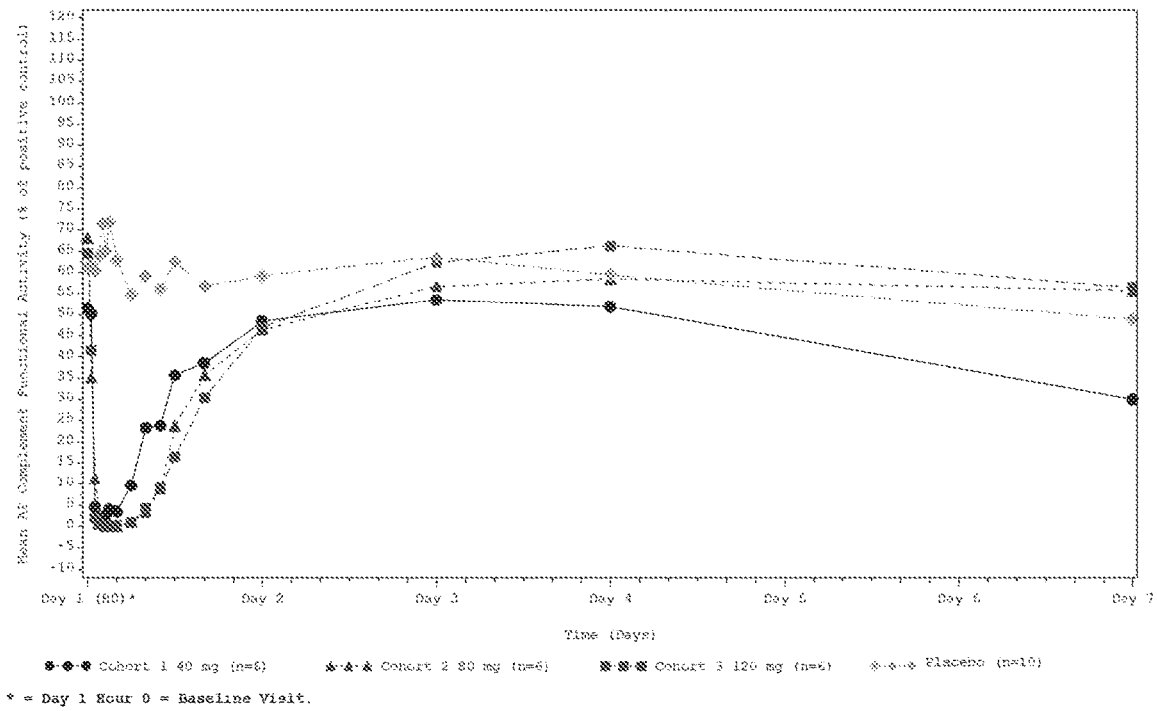

A graphical display of mean complement AP functional activity (% relative to positive control) through Day 7 (reported in days) and within 24 hours of dosing (by randomized treatment group and overall) can be found in FIG. 8B and FIG. 8A, respectively. Potent inhibition of AP functional activity was observed for all subjects administered a single dose of 40 mg, 80 mg, or 120 mg of Compound 1 as assessed by the Wieslab assay.

Inhibition of AP functional activity of >80% (or AP functional activity results of ≤20% relative to positive control) was noted for all Compound 1-treated subjects as early as 0.5 hours post-dose, with all subjects achieving inhibition of AP functional activity of >90% by 2 hours post-dose. Nadirs in AP functional activity were reached between 1.5 hours (in the 40 mg dose group) and 3 hours (in the 80 mg and 120 mg dose groups) post-dose; for the 40 mg, 80 mg, and 120 mg dose groups, mean (±SD) AP functional activity decreased to lowest levels of 1.25 (±1.153)%, 0.13 (±0.097)%, and 0.09 (±0.102)%, respectively. For the 40 mg dose group, mean inhibition of 90% or greater was maintained for at least 6 hours post-dosing. For the higher dose groups studied (i.e., 120 mg and 240 mg), mean inhibition of 90% or greater was maintained for a longer period of time (i.e., for at least 10 hours post-dosing).

Bb Plasma Concentrations

Figure 9A:
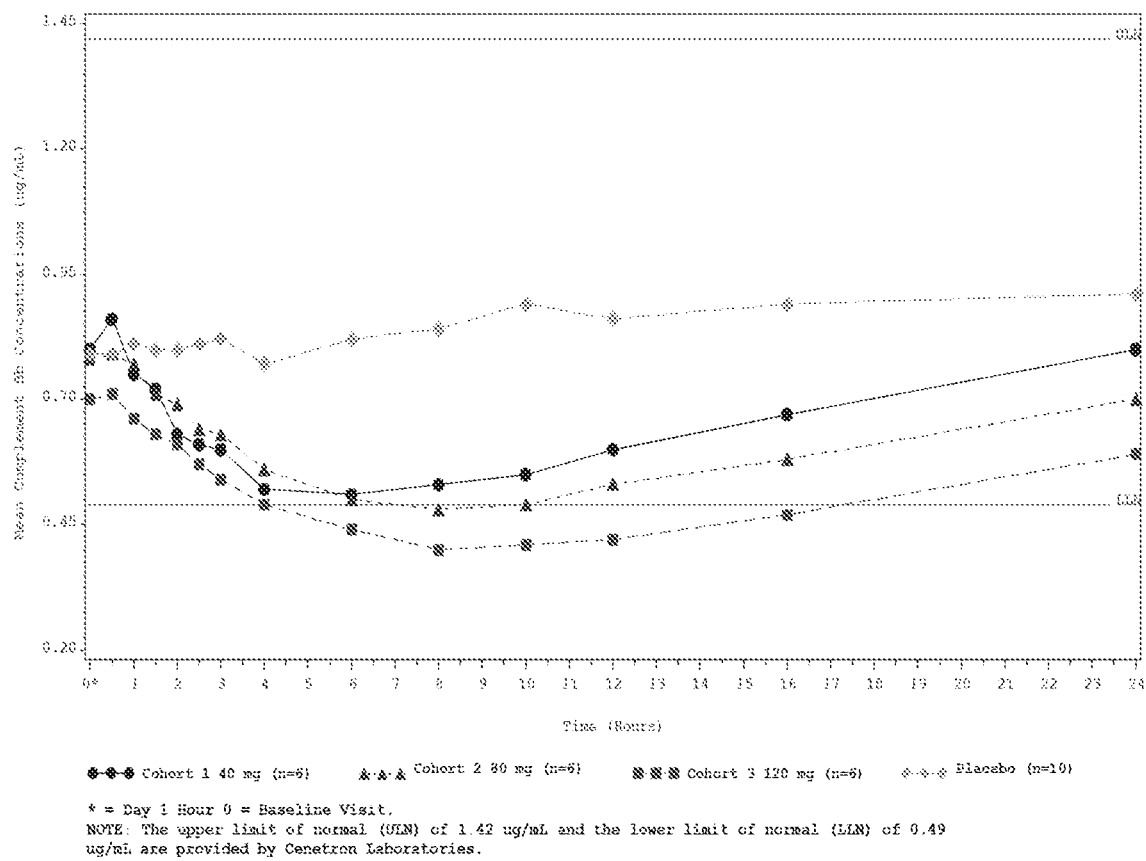
FIG. 9A and FIG. 9B are graphs representing mean changes from baseline in Bb plasma concentration within 24 hours of dosing (FIG. 9A) and over time (FIG. 9B) by randomized treatment group.
Figure 9B:
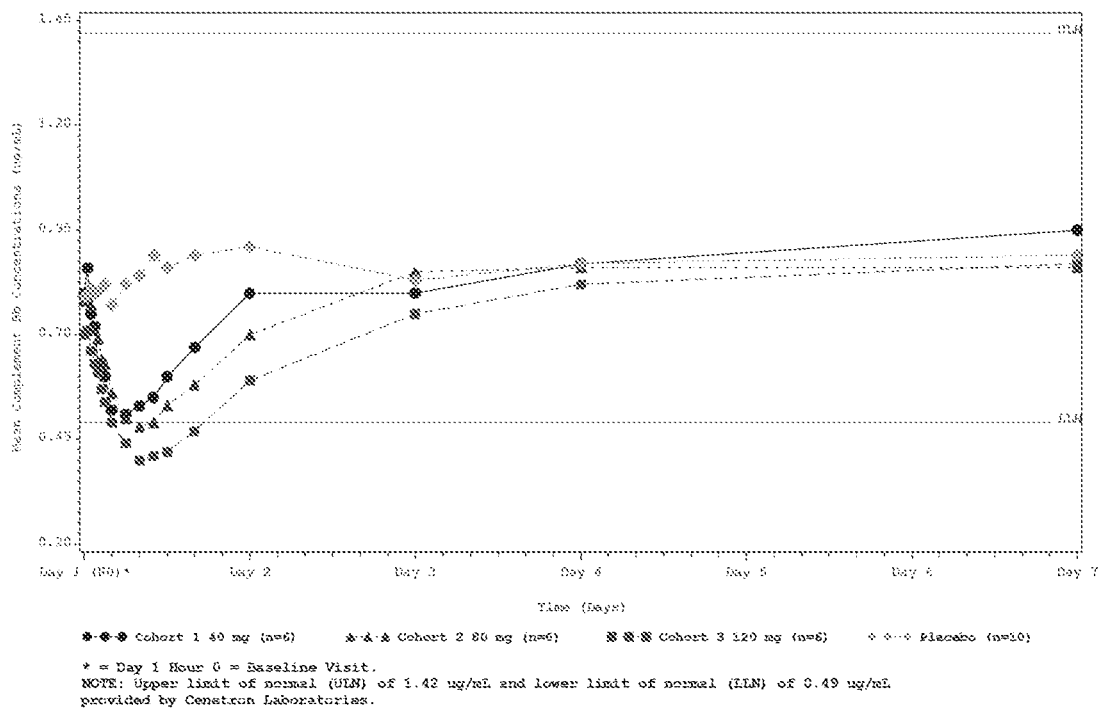

A graphical display of mean plasma Bb concentrations through Day 7 (reported in days) and within 24 hours of dosing (by randomized treatment group and overall) can be found in FIG. 9B and FIG. 9A, respectively. All Compound 1 dose groups evaluated had significant reductions in Bb plasma concentrations after single dose administration relative to baseline and the placebo-treated group as illustrated in FIG. 9A and FIG. 9B. Although the number of subjects evaluated in individual dose groups was relatively small (n=6), the magnitude of changes observed appeared to be dose-dependent. At baseline, the 40 mg, 80 mg, and 120 mg dose groups had Bb plasma concentrations within the normal reference range for the assay (i.e., 0.49 to 1.42 μg/mL); 40 mg, 80 mg, and 120 mg dose groups had mean (±SD) baseline values of 0.80 (±0.195) μg/mL, 0.78 (±0.128) μg/mL, and 0.70 (±0.095) μg/mL, respectively. Bb plasma concentrations reached a nadir 6 hours (in the 40 mg dose group) to 8 hours (in the 80 mg and 120 mg dose groups) post-dosing. Six hours post-dosing, mean (±SD) Bb plasma concentration in the 40 mg dose group had decreased to 0.51 (±0.091) μg/mL. Eight hours post-dosing, mean Bb plasma concentration had decreased to 0.48 (±0.056) μg/mL for the 80 mg dose group and 0.40 (±0.029) μg/mL for the 120 mg dose group. For the 80 mg and 120 mg dose groups, mean Bb plasma concentrations increased to above the LLN for the assay by 10 hours post-dosing (for the 80 mg dose group) and 24 hours (Day 2) (for the 120 mg dose group) post-dosing, respectively, with return to baseline values by 48 hours (Day 3) post-dosing. No subjects had treatment-emergent abnormalities in Bb plasma concentrations during the study.

Figure 10:
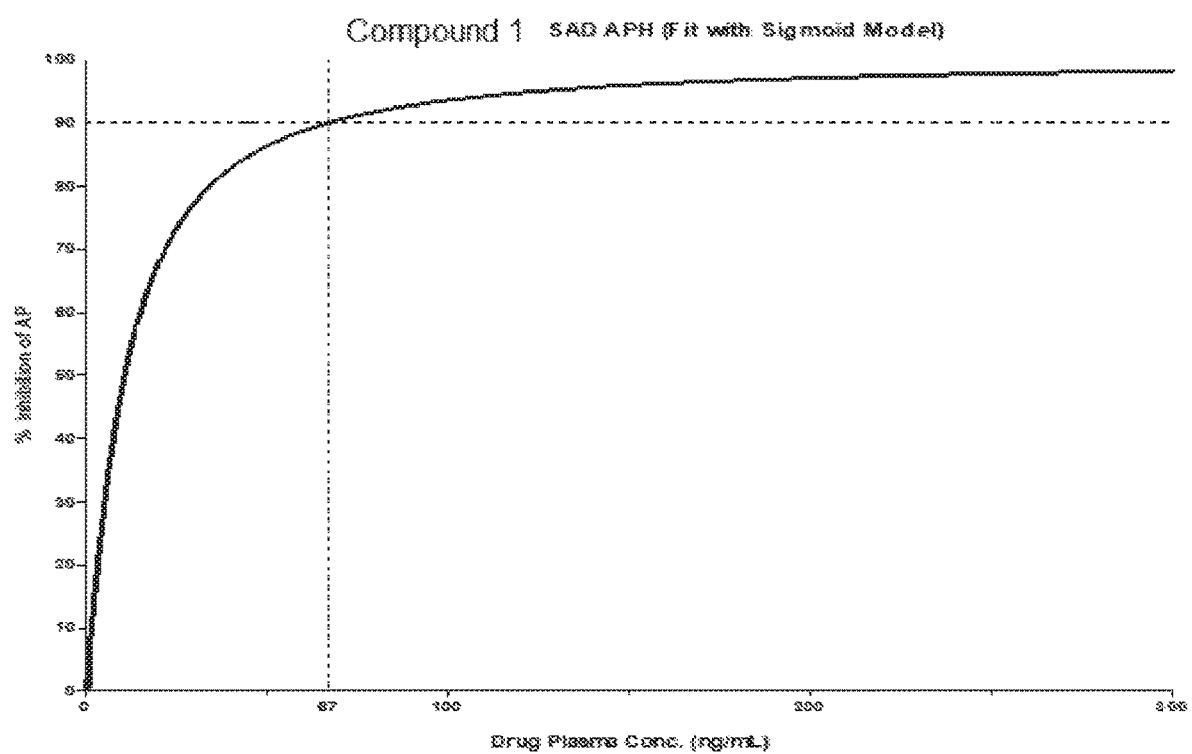
FIG. 10 represents a graphical display of steady-state modeling indicated that a 90% inhibition (IC90) of AP activity is achieved with a $C_{trough}$ of about 67 ng/mL.
Figure 11:
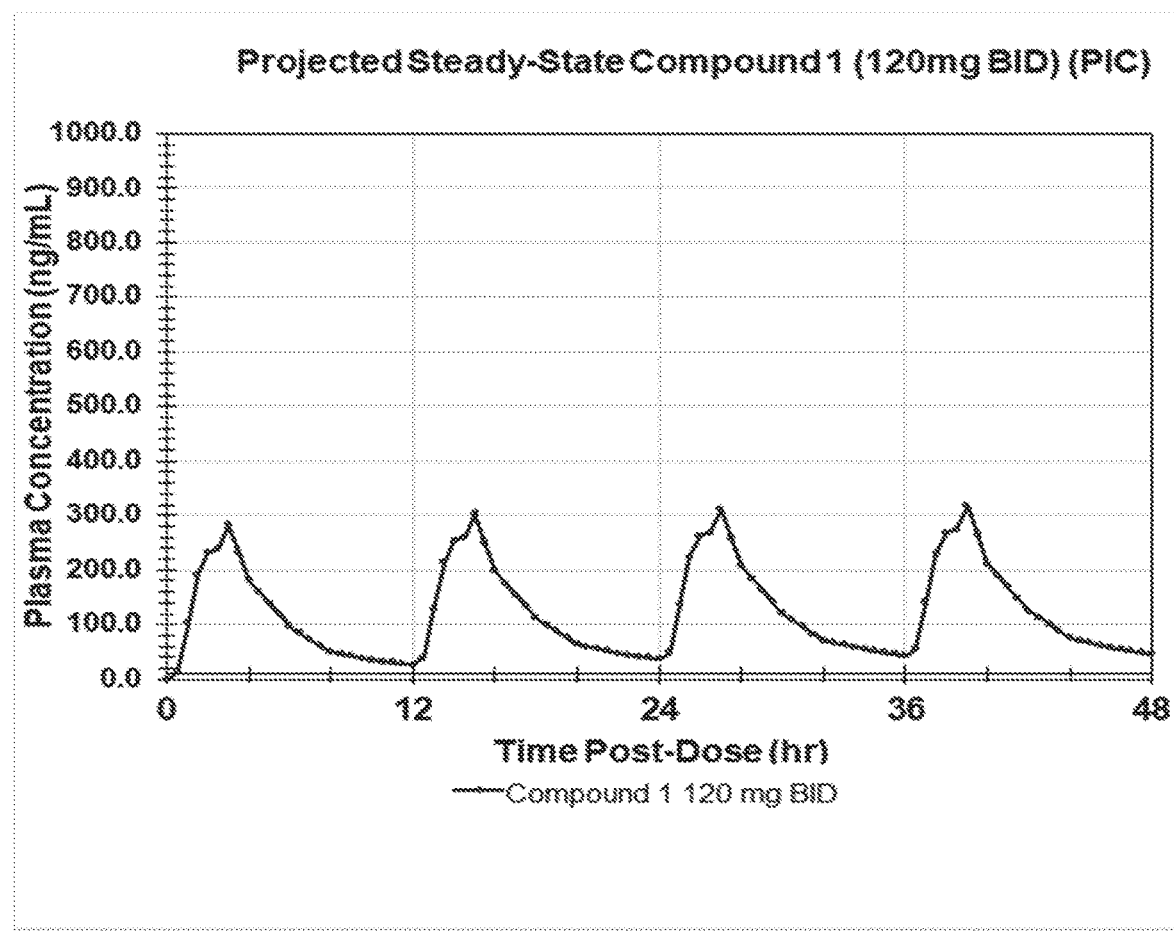
FIG. 11 represents a graphical display of projected steady state of Compound 1 administered at 120 mg twice a day.

Based on the ex vivo AP inhibition assay, a steady state model was prepared comparing the % inhibition of Ap based on drug plasma concentration. A graphical display of steady-state modeling is shown in FIG. 10 and FIG. 11. FIG. 10 shows that a 90% inhibition ($IC_{90}$) is achieved with a $C_{trough}$ of about 67 ng/mL. Therefore, Compound 1 is projected to achieve 85% inhibition at the targeted trough concentrations in vivo. FIG. 11 shows that a projected steady state of administration of 120 mg of Compound 1 twice a day provides a $C_{trough}$ of about 50 ng/mL, achieving greater than 85% inhibition of AP activity, while the $C_{max}$ is below about 350 ng/mL. Therefore, Compound 1 is shown to be potent while still having improved safety margins that may allow for better dosing flexibility.

Summary

Ex vivo AP functional assays, reported herein using AP hemolysis assay, demonstrate that a complete or near complete inhibition of AP pathway was achieved quickly after administration of Compound I in all Cohorts of SAD. The PK/PD analysis using the simple $E_{max}$ model revealed a clear dose-response relationship with $EC_{50}$ of ~10 ng/mL. Pharmacodynamic results demonstrate that Compound 1, an fD inhibitor, achieves potent inhibition of the AP of complement with single dose administration ranging from 40 mg to 120 mg. The ex vivo Wieslab assay that evaluated serum AP activity indicated nearly complete inhibition of AP activity almost immediately after single dose administration of Compound 1. Inhibition of AP activity of >80% was noted for all Compound 1-treated subjects as early as 0.5 hours post-dose, with all subjects achieving inhibition of AP activity of >90% by 2 hours post-dose. Nadirs in AP activity were reached between 1.5 hours (in the 40 mg dose group) and 3 hours (in the 80 mg and 120 mg dose groups) post-dose. For the higher dose groups studied (i.e., 80 mg and 120 mg), mean inhibition of 90% or greater was maintained for a longer period of time (at least 10 hours) compared with the lower 40 mg dose group studied (at least 6 hours) after dosing. Quantitative analysis using an $E_{max}$ model with all time-matched plasma PK data and serum AP activity inhibition data from all dose cohorts yielded an $EC_{50}$ of 11 ng/mL. Additionally, after single dose administration, there were significant reductions in Bb plasma concentration, an in vivo biomarker for AP activity, indicating that AP activity was inhibited in vivo. Although the number of subjects evaluated in individual dose groups was relatively small (n=6), the magnitude of changes observed appeared to be dose-dependent. Bb plasma concentrations reached a nadir 6 hours (in the 40 mg dose group) to 8 hours (in the 80 mg and 120 mg dose groups) post-dosing. Bb plasma concentrations gradually recovered from nadir, with the 40 mg dose group recovering sooner, with all dose groups recovering to baseline values by 48 hours (Day 3) post-dosing. For other complement assays performed evaluating fD serum concentration, C3 serum concentration, C4 serum concentration, and serum total CP function, there were no significant changes over time after single dose administration of up to 120 mg Compound 1 compared with baseline and placebo.

Multiple Ascending Dose (MAD) Study of Compound 1 with Two Additional Single-Dose Cohorts A multiple ascending dose (MAD) study of Compound 1 with two additional single-dose cohorts was also completed. The primary objective was to demonstrate the safety and tolerability of multiple ascending oral doses of Compound 1, an orally administered complement factor D inhibitor, in healthy volunteers. Secondary objectives included evaluation of the pharmacokinetic (PK) profile and the relationship between Compound 1 PK and pharmacodynamic (PD) characteristics, that is, the inhibition of complement alternative pathway (AP) activity (PK/PD). In the MAD study, multiple-dose pharmacokinetics and pharmacodynamics of Compound 1 were evaluated in four dose groups administered Compound 1 (40, 80, 120 and 200 mg BID) in the fasted state for 14-days (Table 3). Eight subjects received active drug in each group; eight subjects received placebo in the first dose group (40 mg) and two subjects received placebo in each of the other three dose groups. Two additional cohorts were administered Compound 1 at single doses of 240 mg (fasted subjects) and 120 mg (fed subjects) (Table 3). The two single-dose cohorts each comprised six subjects receiving active drug and two subjects receiving placebo. Plasma and serum samples for PK and PD assessment were collected on selected days prior to dosing (at local troughs), and on days 1, 7, and 14 at 0.5-hour to 2-hour intervals for more detailed assessment.

TABLE 3

Dose Groups in Compound 1 MAD Study with Additional Single-Dose Cohorts

| Group | Dose (mg) | Regimen | Active (N) | Placebo (N) | Fasted vs Fed |
|---|---|---|---|---|---|
| S1 | 240 mg or PBO | Single Dose | 6 | 2 | Fasted |
| S2 | 120 mg or PBO | Single Dose | 6 | 2 | Fed |
| 1 | 40 mg or PBO | 14 Days BID | 8 | 8 | Fasted |
| 2 | 80 mg or PBO | 14 Days BID | 8 | 2 | Fasted |
| 3 | 120 mg or PBO | 14 Days BID | 8 | 2 | Fasted |
| 4 | 200 mg or PBO | 14 Days BID | 8 | 2 | Fasted | a - Two Group 1 subjects discontinued prior to Day 6 for reasons not due to treatment-emergent adverse events; PK and PD results are available from Day 1 through Day 3.

Compound 1 Single-Dose Pharmacokinetics for 2 Additional Dose Cohorts

The pharmacokinetic results for the 240 mg single dose were consistent with data from the SAD study and demonstrated a dose-proportional increase in exposure ($C_{max}$, AUC) in the single dose range of 40 to 240 mg (Table 4). Comparing the single 120 mg dose given with a moderate-fat meal to the same dose given in the fasted state (SAD study), mean $C_{max}$ and AUC values were 2.2% and 00.8% lower, respectively, in the fed state. This result suggests that Compound 1 may be dosed in either the fed or fasted state with no clinically significant difference in systemic exposure.

TABLE 4

Summary of Pharmacokinetic Parameters of Compound 1 after 240 mg (Fasted) and 120 mg (Fed) Single-Dose Administration

| | ng/mL | hr | ng · hr/mL | | | hr |
|---|---|---|---|---|---|---|
| | $C_{max}$ | $t_{max}$ | $AUC_{(0-12)}$ | $AUC_{(0-72)}$ | $AUC_{0-inf}$ | $t^{1/2}_{term}$ |
| 240 mg Single Dose (Fasted) | | | | | | |
| Mean | 594.33 | 2.67 | 2766.43 | 3510.09 | 3522.69 | 9.33 |
| SD | 266.40 | 0.41 | 1204.44 | 1583.50 | 1598.12 | 1.60 |
| % CV | 45 | 15 | 44 | 45 | 45 | 17 |
| N | 6 | 6 | 6 | 6 | 6 | 6 |
| Min | 236.00 | 2.00 | 1611.26 | 1759.84 | 1761.31 | 8.01 |
| Max | 884.00 | 3.00 | 4491.38 | 5437.66 | 5488.42 | 12.41 |
| 120 mg Single Dose (Fed moderate fat meal) | | | | | | |
| Mean | 309.33 | 2.83 | 1247.50 | 1489.39 | 1493.21 | 9.39 |
| SD | 82.59 | 0.98 | 339.97 | 444.31 | 443.21 | 1.54 |
| % CV | 27 | 35 | 27 | 30 | 30 | 16 |
| N | 6 | 6 | 6 | 6 | 6 | 6 |
| Min | 225.00 | 1.00 | 868.06 | 932.63 | 939.61 | 6.72 |
| Max | 410.00 | 4.00 | 1826.80 | 2173.69 | 2175.85 | 10.97 |

Compound 1 Single-Dose Pharmacodynamics for 2 Additional Dose Cohorts

Figure 14:
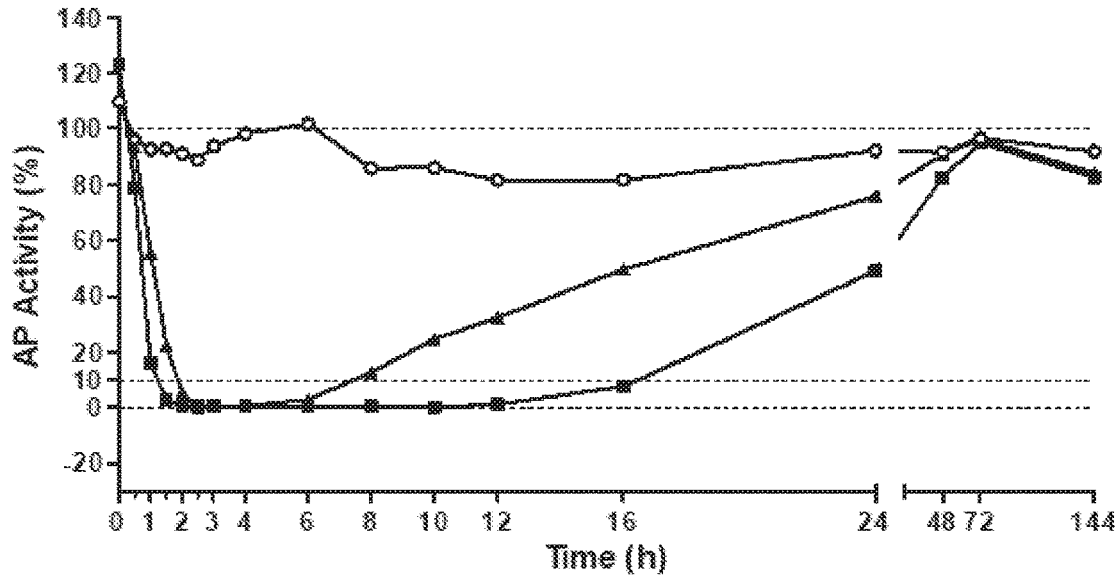
FIG. 14 is a graphical display of mean serum alternative pathway hemolysis of Compound 1 administered at single doses of 240 mg in fasted subjects (n=6), 120 mg in fed subjects (n=6) and placebo (n=4). Serum AP hemolysis was assessed in samples collected at predefined timepoints from Day 1 (pre-dose) to Day 7. The x-axis is Time in hours and the y-axis is % AP activity.
Figure 15:
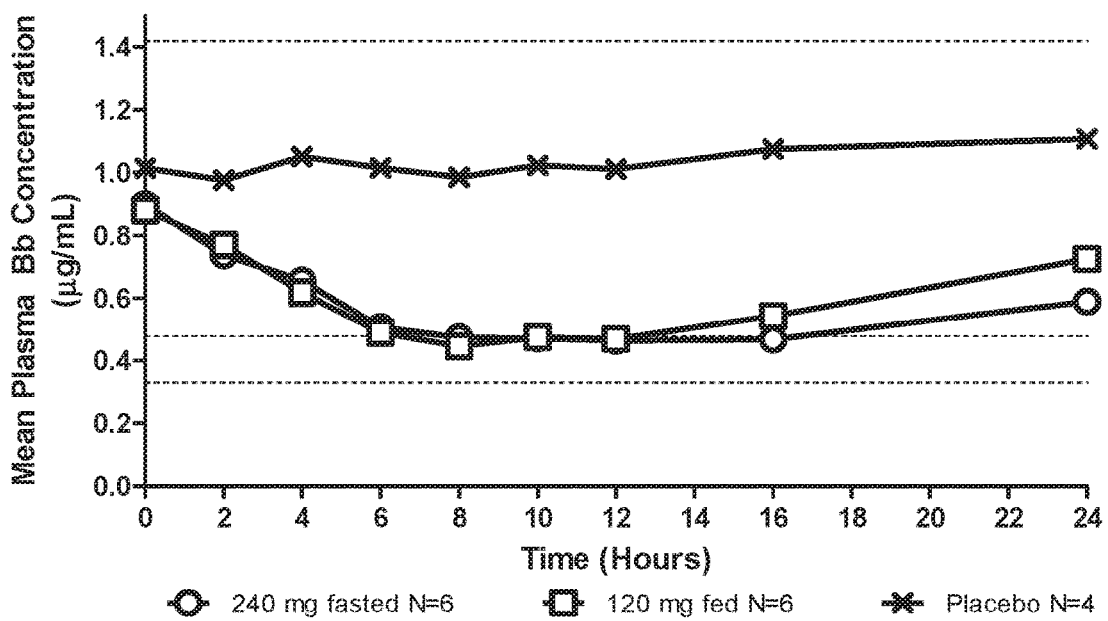
FIG. 15 is a graphical display of mean plasma Bb concentration as determined by ELISA assay for all subjects in the first 24 hours after administration of Compound 1 at single doses of 240 mg in fasted subjects (n=6), 120 mg in fed subjects (n=6) and placebo (n=4). Horizontal dashed gridlines represent: upper limit of normal (1.42 μg/ml); lower limit of normal (0.48 μg/ml); and lower limit of quantitation (LLOQ) (0.33 μg/ml). The x-axis is Time in hours and the y-axis is Mean Plasma Bb Concentration measured in μg/mL.

Pharmacodynamics results from the additional single-dose cohorts in the MAD clinical study of Compound 1 demonstrated continued dose-dependent inhibition of complement AP activity. Serum AP hemolysis activity was assessed in samples collected at predefined time points from Day 1 (pre-dose) through Day 7. Ex vivo serum AP inhibition was more prolonged in the 240 mg dose group than previously observed in the SAD study at doses up to 120 mg (FIG. 14). Serum AP hemolysis activity showed rapid suppression following single-dose Compound 1 administration. Mean pre-dose (Day 1, 0 h) activity among active subjects was 123.02% (240 mg) and 110.43% (120 mg). Activity was reduced to 10% or lower from 1.5 h through 16 h in the 240 mg group, and from 2 h through 6 h in the 120 mg group. Activity was recovered to nearly pre-dose levels by 48 hours. AP activity in placebo subjects in contrast varied little from the pre-dose value of 109.52%, with a minimum value among all time points of 81.46%. All subjects at the 240 mg dose achieved 90% or greater inhibition within two hours of dosing, and mean inhibition persisted at 90% or greater through at least 12 hours post-dose. Additionally, as an indication of AP inhibition in vivo, plasma Bb showed a dose-dependent reduction; the inhibitory effect of Compound 1 was more prolonged in the 240 mg dose group than at lower doses, remaining near its nadir for at least 16 hours post-dose (FIG. 15). Placebo subjects did not show notable changes following dosing in AP activity or in plasma Bb concentration, and active subjects showed no significant changes in serum CP activity or in serum factor D, C3, or C4 concentrations following Compound 1 administration.

Compound 1 Multiple-Dose Pharmacokinetics

Mean exposures ($C_{max}$ and $AUC_{0-inf}$) increased in a linear, dose-proportional manner on Day 1, after the initial doses in the 40, 80, 120 and 200 mg multi-dose cohorts. When each dose was given on a repeated twice daily (BID) regimen, greater-than-dose-proportional increases in steady-state exposures were observed. Mean accumulation from Day 1 (first dose) to Days 7/14 (steady-state) for both $C_{max}$ and AUC increased from 1.7 to 4.7 as the dose was increased, highlighting the non-linear PK behavior of Compound 1. The mean $t\frac{1}{2}_{term}$ upon washout after the last dose on Day 14 for all 4 dose groups was in the range of 9.0 to 11.9 hours, similar in magnitude to that observed after administration of a single dose. There was no observable trend for this half-life to increase as the dose was increased.

Figure 16:
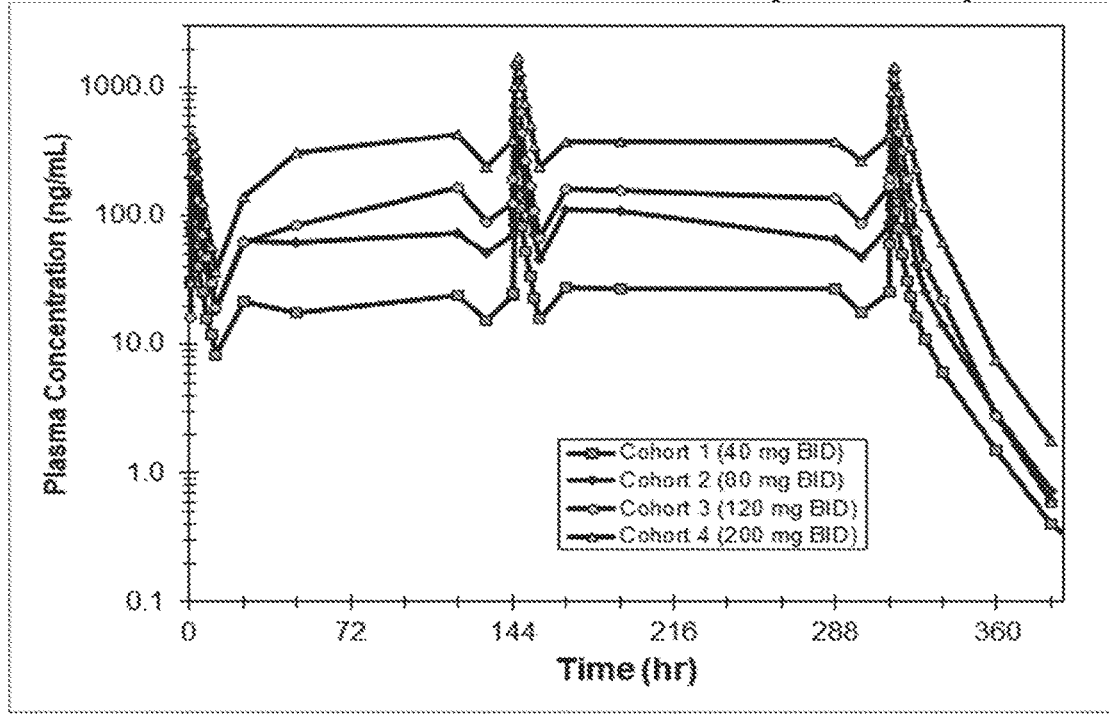
FIG. 16 is a graphical display of mean plasma concentration of Compound 1 administered at 40 mg BID (n=8), 80 mg BID (n=7), 120 mg BID (n=8), 200 mg BID (n=8), and placebo BID (n=14). Plasma concentration for each cohort was assessed in samples collected at predefined timepoints from Day 1 (pre-dose) to Day 16. The x-axis is Time in hours and the y-axis is Mean Plasma Concentration measured in ng/mL.

FIG. 16 is a plot of mean concentrations for the four dose groups and Table 5 summarizes mean multiple dose pharmacokinetic parameters for all groups.

There was a consistent trend for pre-dose plasma concentrations at steady-state to be higher in the morning than in the evening, with some morning troughs being about twice the value of evening troughs. Mean pre-dose concentrations for the 40, 80, 120 and 200 mg BTD groups were in the respective ranges of 15.6-23.5 ng/mL, 45.9-83.7 ng/mL, 80.6-153 ng/mL and 247-392 ng/mL (Table 6).

TABLE 5

Summary of Pharmacokinetic Parameters of Compound 1 After Repeat-Dose Administration for 14 Days

| | | Day 1 | | | Day 7 | | | | Day 14 | | |
|---|---|---|---|---|---|---|---|---|---|---|---|
| | ng/mL | hr | ng · hr/mL | ng/mL | hr | ng · hr/mL | | ng/mL | Hr | ng · hr/mL | |
| | $C_{max}$ | $t_{max}$ | $AUC_{(0-12)}$ | $C_{max}$ | $t_{max}$ | $AUC_{(0-12)}$ | $AUC_{(0-24)}$ | $C_{max}$ | $t_{max}$ | $AUC_{(0-12)}$ | $AUC_{(0-24)}$ |
| 200 mg BID × 14 Days | | | | | | | | | | | |
| Mean | 440.38 | 1.63 | 1817.04 | 1866.88 | 2.06 | 9349.79 | 18699.59 | 1634.38 | 1.81 | 8241.79 | 16483.59 |
| SD | 177.32 | 0.44 | 584.15 | 886.54 | 0.68 | 6977.07 | 13954.13 | 767.27 | 0.59 | 6156.52 | 12313.04 |
| % CV | 40 | 27 | 32 | 47 | 33 | 75 | 75 | 47 | 33 | 75 | 75 |
| N | 8 | 8 | 8 | 8 | 8 | 8 | 8 | 8 | 8 | 8 | 8 |
| Min | 178.00 | 1.00 | 742.05 | 615.00 | 1.00 | 2829.95 | 5659.90 | 805.00 | 1.00 | 3277.30 | 6554.60 |
| Max | 685.00 | 2.50 | 2282.35 | 3500.00 | 3.00 | 24712.50 | 49425.00 | 3300.00 | 2.50 | 22477.50 | 44955.00 |
| 120 mg BID × 14 Days | | | | | | | | | | | |
| Mean | 352.63 | 2.00 | 1196.02 | 885.38 | 1.75 | 3877.10 | 7754.19 | 887.25 | 2.50 | 3994.82 | 7989.64 |
| SD | 110.32 | 0.60 | 398.53 | 217.57 | 0.65 | 1287.96 | 2575.91 | 199.78 | 1.49 | 717.89 | 1435.78 |
| % CV | 31 | 30 | 33 | 25 | 37 | 33 | 33 | 23 | 60 | 18 | 18 |
| N | 8 | 8 | 8 | 8 | 8 | 8 | 8 | 8 | 8 | 8 | 8 |
| Min | 218.00 | 1.50 | 799.90 | 607.00 | 1.00 | 2216.25 | 4432.50 | 653.00 | 1.50 | 3091.85 | 6183.70 |
| Max | 544.00 | 3.00 | 1888.14 | 1200.00 | 2.50 | 5909.25 | 11818.50 | 1120.00 | 6.00 | 4945.50 | 9891.00 |
| 80 mg BID × 14 Days | | | | | | | | | | | |
| Mean | 206.71 | 1.79 | 855.69 | 472.14 | 2.00 | 1993.86 | 3987.71 | 453.14 | 2.14 | 1984.13 | 3968.26 |
| SD | 67.15 | 0.70 | 190.98 | 171.00 | 0.58 | 846.36 | 1692.71 | 163.36 | 0.80 | 648.58 | 1297.15 |
| % CV | 32 | 39 | 22 | 36 | 29 | 42 | 42 | 36 | 37 | 33 | 33 |
| N | 7 | 7 | 7 | 7 | 7 | 7 | 7 | 7 | 7 | 7 | 7 |
| Min | 128.00 | 1.00 | 555.47 | 251.00 | 1.50 | 1020.85 | 2041.70 | 277.00 | 1.00 | 1281.98 | 2563.95 |
| Max | 333.00 | 2.50 | 1054.60 | 717.00 | 3.00 | 3483.15 | 6966.30 | 725.00 | 3.00 | 3040.15 | 6080.30 |
| 40 mg BID × 14 Days | | | | | | | | | | | |
| Mean | 107.03 | 1.56 | 392.35 | 169.40 | 1.80 | 740.71 | 1481.41 | 155.78 | 1.58 | 731.57 | 1463.13 |
| SD | 43.48 | 0.62 | 129.72 | 61.79 | 0.45 | 287.19 | 574.39 | 59.04 | 0.38 | 292.60 | 585.19 |
| % CV | 41 | 40 | 33 | 36 | 25 | 39 | 39 | 38 | 24 | 40 | 40 |
| N | 8 | 8 | 8 | 5 | 5 | 5 | 5 | 6 | 6 | 6 | 6 |
| Min | 65.40 | 1.00 | 288.75 | 91.00 | 1.50 | 421.68 | 843.35 | 91.50 | 1.00 | 423.60 | 847.20 |
| Max | 202.00 | 2.50 | 660.78 | 250.00 | 2.50 | 1025.15 | 2050.30 | 220.00 | 2.00 | 1196.23 | 2392.45 |

TABLE 6

Mean Steady-State Pre-Dose (Trough) Plasma Concentrations (ng/mL) of Compound 1 After Repeat-Dose Administration

| Hr Post-Dose Hours | Day 6 0 120 | Day 6 12 132 | Day 7 0 144 | Day 7 12 156 | Day 8 0 168 | Day 9 0 192 | Day 13 0 288 | Day 13 12 300 | Day 14 0 312 | Day 14 12 324 | Mean (ng/mL) $C_{(0)}$ | Mean (ng/mL) $C_{(12)}$ |
|---|---|---|---|---|---|---|---|---|---|---|---|---|
| 200 mg BID × 14 Days | | | | | | | | | | | | |
| Mean | 430.74 | 240.90 | 385.25 | 241.30 | 381.30 | 376.51 | 376.36 | 272.04 | 414.98 | 235.41 | 392.40 | 247.41 |
| SD | 504.42 | 280.22 | 509.41 | 355.89 | 461.61 | 381.37 | 428.31 | 325.81 | 521.38 | 304.84 | 457.36 | 314.30 |
| % CV | 117 | 116 | 132 | 147 | 121 | 101 | 114 | 120 | 126 | 129 | 117 | 127 |
| N | 7 | 8 | 8 | 8 | 8 | 8 | 8 | 8 | 8 | 8 | 8 | 8 |
| Min | 92.90 | 49.00 | 69.40 | 53.30 | 86.40 | 81.10 | 70.50 | 43.90 | 72.00 | 37.90 | 90.33 | 46.03 |
| Max | 1490.00 | 903.00 | 1600.00 | 1110.00 | 1500.00 | 1240.00 | 1370.00 | 1020.00 | 1650.00 | 965.00 | 1475.00 | 999.50 |
| 120 mg BID × 14 Days | | | | | | | | | | | | |
| Mean | 164.88 | 90.58 | 125.36 | 67.21 | 163.88 | 156.00 | 135.89 | 88.04 | 172.63 | 76.60 | 153.10 | 80.61 |
| SD | 104.84 | 52.74 | 86.85 | 36.48 | 63.53 | 51.89 | 77.27 | 41.52 | 64.89 | 38.06 | 69.52 | 41.04 |
| % CV | 64 | 58 | 69 | 54 | 39 | 33 | 57 | 47 | 38 | 50 | 45 | 51 |
| N | 8 | 8 | 8 | 8 | 8 | 8 | 8 | 8 | 8 | 8 | 8 | 8 |
| Min | 64.60 | 44.90 | 56.20 | 30.40 | 99.00 | 104.00 | 83.90 | 57.20 | 110.00 | 50.70 | 90.25 | 47.80 |
| Max | 376.00 | 198.00 | 318.00 | 149.00 | 270.00 | 256.00 | 320.00 | 187.00 | 314.00 | 168.00 | 309.00 | 175.50 |
| 80 mg BID × 14 Days | | | | | | | | | | | | |
| Mean | 73.81 | 52.09 | 69.09 | 43.70 | 109.10 | 102.10 | 63.30 | 45.21 | 85.00 | 42.47 | 83.73 | 45.87 |
| SD | 25.94 | 22.49 | 32.65 | 22.93 | 62.51 | 73.70 | 38.48 | 23.82 | 46.20 | 25.62 | 42.29 | 21.60 |
| % CV | 35 | 43 | 47 | 52 | 57 | 72 | 61 | 53 | 54 | 60 | 51 | 47 |
| N | 7 | 7 | 7 | 7 | 7 | 7 | 7 | 7 | 7 | 7 | 7 | 7 |
| Min | 38.90 | 19.80 | 30.60 | 13.40 | 23.60 | 33.20 | 28.70 | 30.00 | 38.50 | 18.20 | 32.25 | 20.35 |
| Max | 122.00 | 80.80 | 121.00 | 77.40 | 220.00 | 253.00 | 142.00 | 96.70 | 156.00 | 95.90 | 148.75 | 84.80 |
| 40 mg BID × 14 Days | | | | | | | | | | | | |
| Mean | 27.80 | 17.87 | 24.26 | 15.72 | 27.76 | 26.86 | 23.50 | 15.35 | 25.23 | 16.18 | 23.45 | 15.60 |
| SD | 13.37 | 9.64 | 12.57 | 8.04 | 9.76 | 13.89 | 15.14 | 11.46 | 15.83 | 7.32 | 14.24 | 8.65 |
| % CV | 48 | 54 | 52 | 51 | 35 | 52 | 64 | 75 | 63 | 45 | 61 | 55 |
| N | 5 | 5 | 5 | 5 | 5 | 5 | 6 | 6 | 6 | 6 | 6 | 6 |
| Min | 14.90 | 9.66 | 13.80 | 10.10 | 17.20 | 15.30 | 7.10 | 3.29 | 2.10 | 7.95 | 4.60 | 8.70 |
| Max | 47.70 | 33.10 | 45.40 | 29.60 | 42.80 | 49.40 | 46.50 | 36.60 | 44.70 | 28.20 | 45.55 | 31.88 |

Figure 13:
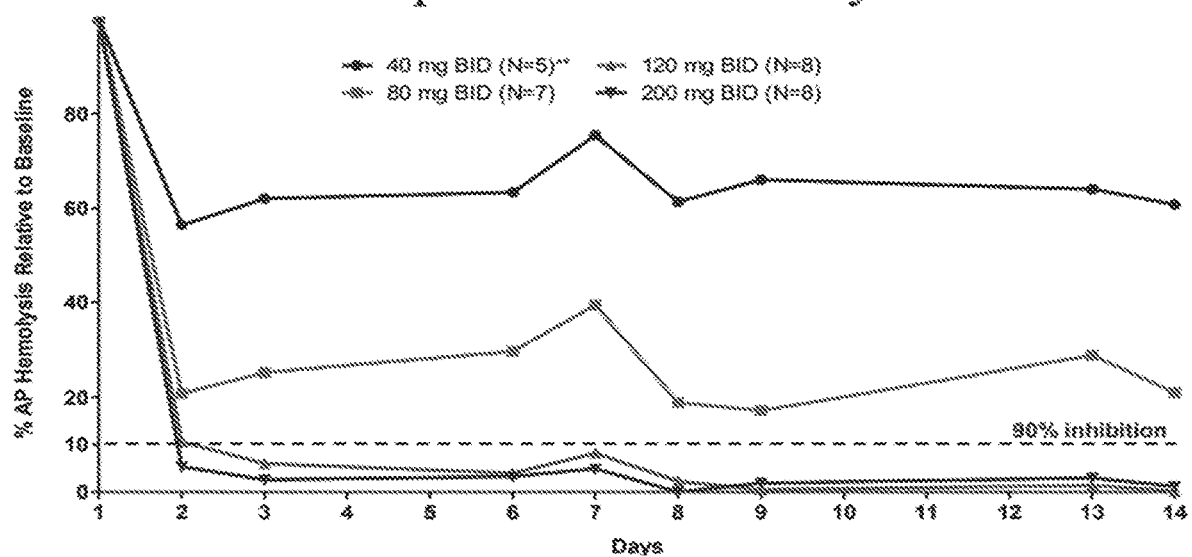
FIG. 13 is a graphical display of average reduction in alternative pathway hemolysis in patients dosed with 40 mg, 80 mg, 120 mg, or 200 mg of Compound 1 for 14 days. The y-axis is % AP hemolysis relative to baseline. The x-axis is number of days on therapy wherein day 1 is the first day dosed. The data points are collected at hour 0 each day. Two subjects on the 40 mg BID study were discontinued for non-safety related reasons and a 3rd subject was removed from the analysis due to a missed dose on day 7.

Compound 1 Multiple-Dose Pharmacodynamics
Mean Reduction in AP Hemolysis in Patients Dosed BID with Compound 1 for 14 Days The mean reduction in alternative pathway hemolysis is shown in FIG. 13. Both the 120 mg and 200 mg BID patient group had over 90% reduction in AP hemolysis for the duration of the study. On average this reduction was over 95% (see FIG. 13).

Serum AP Hemolysis Activity in Multiple-Dose Cohorts

Figure 17:
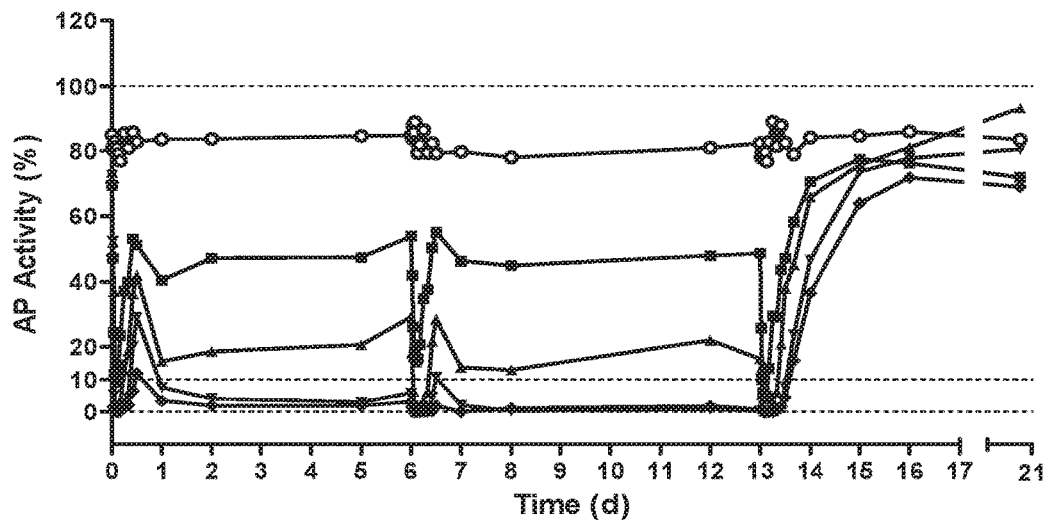
FIG. 17 is a graphical display of mean serum alternative pathway hemolysis activity of Compound 1 administered at 40 mg BID (n=8), 80 mg BID (n=7), 120 mg BID (n=8), 200 mg BID (n=8), and placebo BID (n=14). Activity for each cohort is shown for the full 21-day time course. Intense sampling was obtained on Day 1 (0 h to 12 h), Day 7 (0 h to 12 h), and Day 14 (0 h to 16 h); all other serum samples were collected at 0 h (morning PK troughs) on the indicated days. The x-axis is Time in days and the y-axis is % AP activity.
Figure 18:
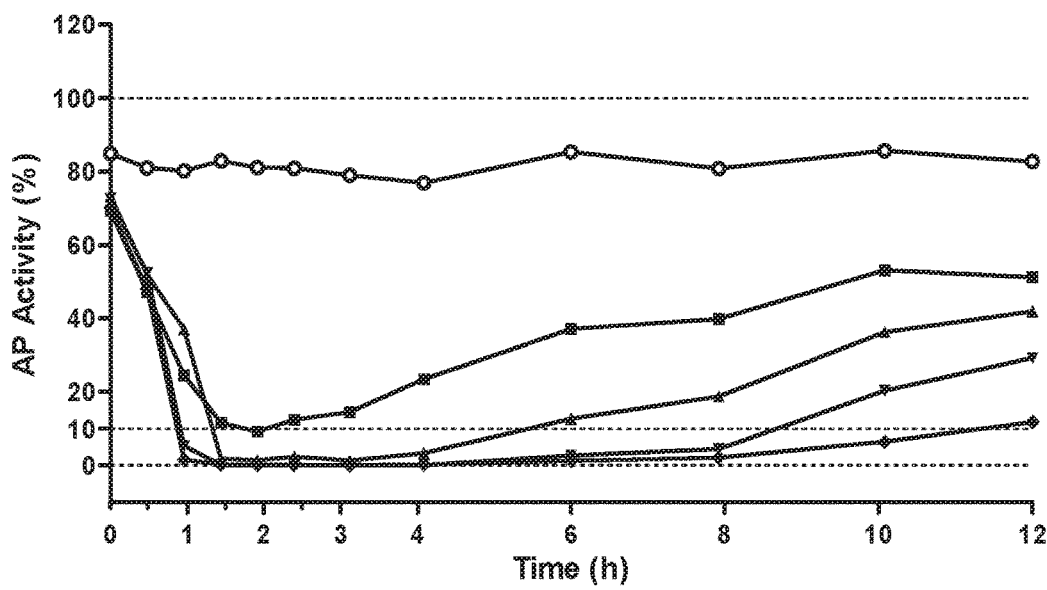
FIG. 18 is a graphical display of mean serum alternative pathway hemolysis activity of Compound 1 administered at 40 mg BID (n=8), 80 mg BID (n=7), 120 mg BID (n=8), 200 mg BID (n=8), and placebo BID (n=14). Intense sampling was obtained on Day 1 (0 h to 12 h). The x-axis is Time in hours and the y-axis is % AP activity.
Figure 19:
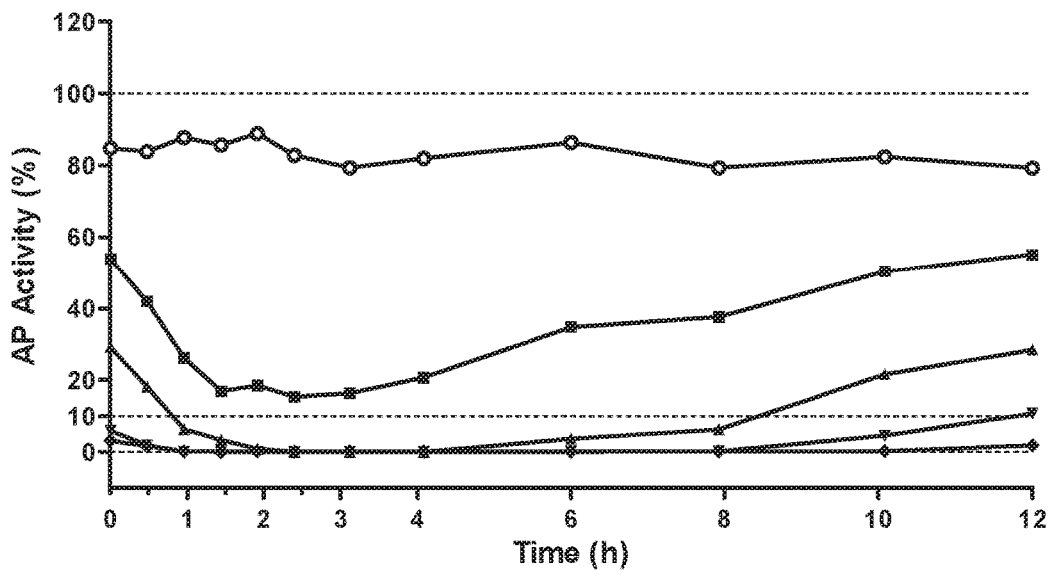
FIG. 19 is a graphical display of mean serum alternative pathway hemolysis activity of Compound 1 administered at 40 mg BID (n=8), 80 mg BID (n=7), 120 mg BID (n=8), 200 mg BID (n=8), and placebo BID (n=14). Intense sampling was obtained on Day 7 (0 h to 12 h). The x-axis is Time in hours and the y-axis is % AP activity.
Figure 20:
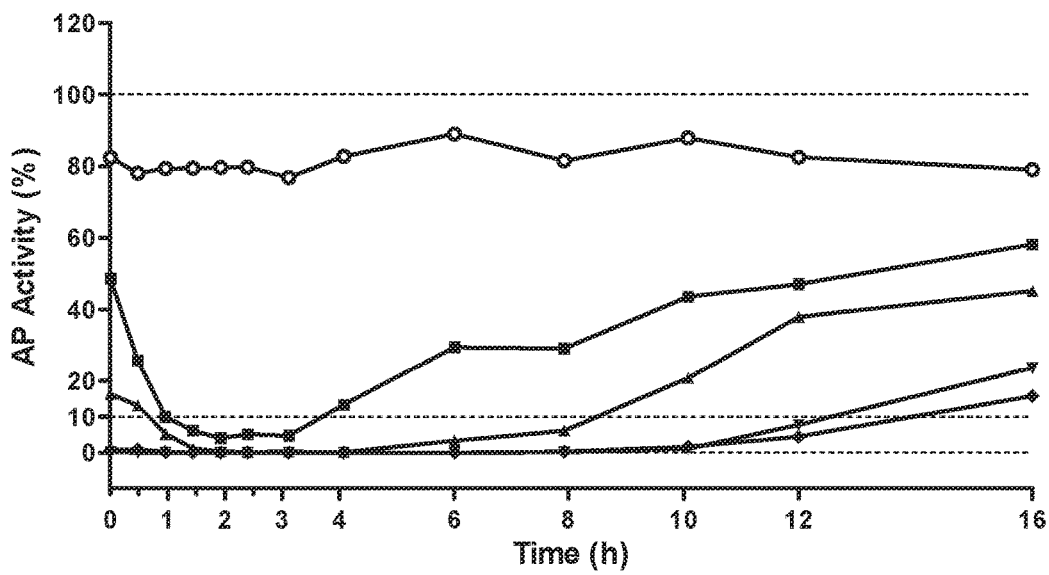
FIG. 20 is a graphical display of mean serum alternative pathway hemolysis activity of Compound 1 administered at 40 mg BID (n=8), 80 mg BID (n=7), 120 mg BID (n=8), 200 mg BID (n=8), and placebo BID (n=14). Intense sampling was obtained on Day 14 (0 h to 12 h). The x-axis is Time in hours and the y-axis is % AP activity.

Serum AP hemolysis activity was assessed in samples collected from all cohorts at predefined time points from Day 1 (pre-dose) through Day 21. Intense sampling was obtained on Day 1 (0 h to 12 h), Day 7 (0 h to 12 h), and Day 14 (0 h to 16 h); all other serum samples were collected at 0 h (morning PK troughs) on the indicated days. Activity for each cohort is shown for the complete time course Day 1-21 (FIG. 17), Day 1 (FIG. 18), Day 7 (FIG. 19) and Day 14 (FIG. 20). Serum complement AP activity measured ex vivo by the AP Wieslab assay, serum total complement classical pathway (CP) activity, plasma complement Bb concentrations, and serum FD, C3, and C4 concentrations were also measured at predefined time points.

Serum AP activity showed rapid and dose-dependent suppression following multiple-dose ACH-5228 administration. Mean pre-dose (Day 1, 0 h) AP activity among active subjects in each cohort ranged from 69.43% (40 mg) to 73.29% (80 mg). On Days 7 and 14 (steady-state PK conditions), activity following dosing was reduced to minimum values of 4.00% (40 mg) and 0.00% (Groups 2 through 4). At 40 mg BID and 80 mg BID, however, this AP suppression was accompanied by substantial recovery at PK troughs (0 h and 12 h time points). At 120 mg BID, in contrast, mean AP activity remained below 10% at all time points from 0 h to 10 h on Day 7 and from 0 h to 12 h on Day 14. At 200 mg BID, mean AP activity remained below 10% at all time points from 0 h to 12 h on Days 7 and 14. AP activity at all doses was recovered to approximately pre-dose levels by Day 17, three days after the last dose. AP activity in placebo subjects in contrast varied little from the pre-dose value of 84.97%, with a minimum value among all time points of 76.84%.

Sigmoidal Model for Percent Inhibition of the Alternative Pathway

Figure 12:
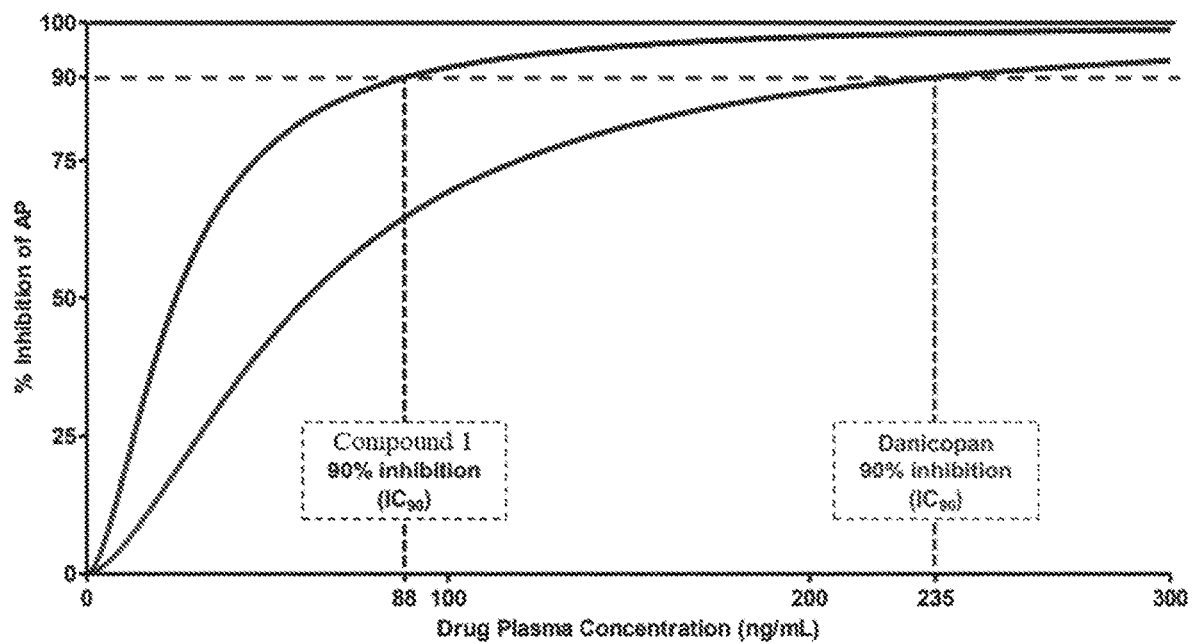
FIG. 12 is a graphical display fitting multiple ascending dose inhibition of Compound 1 and Danicopan to a sigmoidal model. The y-axis is % inhibition of the alternative pathway. The x-axis is drug plasma concentration in ng/mL. The modeled 90% inhibition level for Compound 1 is at 88 ng/mL. The modeled 90% inhibition level for Danicopan is 235 ng/mL.

The aggregate percent inhibition of the alternative pathway, as measured by an ex-vivo AP hemolysis assay with patient samples, was fit to a sigmoidal dose response model to determine the $IC_{90}$ of Compound 1. The modeled $IC_{90}$ drug plasma concentration was 88 ng/mL for Compound 1 (see FIG. 12). This is more than 2.5 times more potent than first generation factor D inhibitor Danicopan which achieves a 90% inhibition at 235 ng/mL (see FIG. 12). Further, greater than 95% mean alternative pathway inhibition was achieved at a steady state $C_{trough}$ with oral 120 mg BID dosing.

AP Inhibition at PK Troughs (0 h and 12 h)

Table 7 presents the calculated percent inhibition of AP hemolysis activity at 0 h and 12 h time points on Days 7 and 14, and collectively for all 0 h and 12 h time points from Days 6 through 14 (representing PK troughs under conditions of steady-state PK). At 40 mg BID and 80 mg BID, partial inhibition was observed at the 0 h and 12 h time points. At 120 mg BID, inhibition exceeded 90% across all 0 h time points (97.2% inhibition) and nearly so across all 12 h time points (87.8% inhibition). At 200 mg BID, inhibition exceeded 90% across all 0 h and 12 h time points (97.6% and 95.1% inhibition, respectively). These results agree with findings derived from the AP Wieslab assay, with calculated percent inhibition exceeding 90% across 0 h and 12 h time points at both 120 mg BID and 200 mg BID.

from 0 h to 12 h At 40 mg BID and 80 mg BID, calculated % $AUEC_{0-12}$ values below 90% reflect the substantial recovery of AP hemolysis activity observed between doses. At 120 mg BID and 200 mg BID, mean % $AUEC_{0-12}$ values (Days 7 and 14, combined analysis) were 98.2% and 99.1%, respectively, indicating nearly complete AP inhibition through the entire 12-hour periods (Table 8). These values agree with findings derived from the AP Wieslab assay, with

TABLE 7

Inhibition of Serum AP Hemolysis Activity in Multiple-Dose Cohorts at 0 hr. and 12 hr. Time Points (PK Troughs): Day 7, Day 14, and Days 6 through 14

|  | Day 7 [a] | | Day 14 [b] | | Days 6 Through 14 [c] | |
| --- | --- | --- | --- | --- | --- | --- |
|  | AP Inhibition at 0 hr (%) | AP Inhibition at 12 hr (%) | AP Inhibition at 0 hr (%) | AP Inhibition at 12 hr (%) | AP Inhibition at 0 hr (%) | AP Inhibition at 12 hr (%) |
| Cohort 1: 40 mg BID | | | | | | |
| Mean | 20.0 | 17.5 | 29.2 | 29.0 | 28.7 | 23.3 |
| SD | 22.5 | 19.3 | 32.0 | 22.8 | 23.7 | 21.0 |
| % CV | 113 | 111 | 110 | 79 | 83 | 90 |
| Min | −9.8 | −15.6 | −20.9 | −14.7 | −20.98 | −15.6 |
| Max | 47.8 | 41.4 | 58.5 | 49.5 | 58.7 | 49.5 |
| Cohort 2: 80 mg BID | | | | | | |
| Mean | 60.5 | 61.5 | 79.0 | 52.0 | 74.1 | 56.8 |
| SD | 21.1 | 16.6 | 21.4 | 30.3 | 20.1 | 24.0 |
| % CV | 35 | 27 | 27 | 58 | 27 | 42 |
| Min | 19.9 | 35.9 | 46.1 | 4.0 | 19.9 | 4.0 |
| Max | 84.2 | 88.4 | 98.2 | 90.4 | 99.9 | 90.4 |
| Cohort 3: 120 mg BID | | | | | | |
| Mean | 91.8 | 86.0 | 99.7 | 89.7 | 97.2 | 87.8 |
| SD | 7.6 | 13.7 | 0.4 | 8.1 | 4.8 | 11.1 |
| % CV | 8 | 16 | 0 | 9 | 5 | 13 |
| Min | 80.5 | 63.5 | 98.8 | 75.3 | 80.5 | 63.5 |
| Max | 99.6 | 99.8 | 100.0 | 97.1 | 100.0 | 99.8 |
| Cohort 4: 200 mg BID | | | | | | |
| Mean | 95.0 | 97.3 | 98.8 | 92.8 | 97.6 | 95.1 |
| SD | 6.8 | 3.7 | 3.4 | 11.0 | 5.4 | 8.3 |
| % CV | 7 | 4 | 3 | 12 | 6 | 9 |
| Min | 83.1 | 89.6 | 90.3 | 69.1 | 78.3 | 69.1 |
| Max | 100.0 | 100.0 | 100.0 | 100.0 | 100.0 | 100.0 |

[a] AP inhibition (%) at 0 h and 12 h (morning and evening PK troughs) on Day 7.
[b] AP inhibition (%) at 0 h and 12 h (morning and evening PK troughs) on Day 14.
[c] AP inhibition (%) at 0 h (morning PK troughs) on Days 6, 7, 8, 9, 13, and 14, and at 12 h (evening PK troughs) on Days 7 and 14.

Integrated Magnitude and Duration of AP Hemolysis Inhibition in Multiple-Dose Cohorts Serum AP activity in multiple dose individuals at each time point was normalized to pre-dose activity (Day 1, 0 h, defined as 1000%) of the same individual. Inhibition of such pre-dose normalized AP activity at each time point was calculated as the reduction from pre-dose activity (i.e., 100%-pre-dose normalized activity). These AP inhibition values were used to calculate the following two PD parameters to quantitate the integrated magnitude and duration of AP inhibition on Days 7 and 14.

First, the integrated magnitude of AP inhibition from 0 h to 12 h was calculated as the Area Under the Effect Curve (AUEC) from 0 h to 12 h ($AUEC_{0-12}$). $AUEC_{0-12}$ was calculated by the linear trapezoidal method, in which the areas under the linear functions between adjacent time points from 0 h to 12 h are summed. Further, % $AUEC_{0-12}$ was calculated as $AUEC_{0-12}$ normalized to its maximal possible value for the interval; a maximum % $AUEC_{0-12}$ of 100% indicates complete (100%) inhibition continuously % $AUEC_{0-12}$ values (Days 7 and 14, combined analysis) of 98.6% and 99.3% at 120 mg BID and 200 mg BID, respectively.

TABLE 8

Integrated Magnitude of AP Hemolysis Inhibition from 0 h to 12 h ($AUEC_{0-12}$) in Multiple-Dose Cohorts: Days 7 and 14

| | % $AUEC_{0-12}$ (%) [a] | | |
| --- | --- | --- | --- |
| | Day 7 | Day 14 | Days 7 and 14 Combined Analysis [b] |
| Cohort 1: 40 mg BID (n = 8) | | | |
| Mean | 49.9 | 61.4 | 55.6 |
| SD | 25.9 | 14.6 | 21.0 |
| % CV | 52 | 24 | 38 |
| Min | 1.5 | 43.2 | 1.5 |
| Max | 73.4 | 75.3 | 75.3 |

TABLE 8-continued

Integrated Magnitude of AP Hemolysis Inhibition from
0 h to 12 h ($AUEC_{0-12}$) in Multiple-Dose Cohorts:
Days 7 and 14

| | % $AUEC_{0-12}$ (%) [a] | | |
|---|---|---|---|
| | Day 7 | Day 14 | Days 7 and 14 Combined Analysis [b] |
| Cohort 2: 80 mg BID (n = 7) | | | |
| Mean | 87.4 | 87.7 | 87.6 |
| SD | 7.6 | 9.3 | 8.2 |
| % CV | 9 | 11 | 9 |
| Min | 74.2 | 75.4 | 74.2 |
| Max | 97.4 | 98.5 | 98.5 |
| Cohort 3: 120 mg BID (n = 8) | | | |
| Mean | 97.5 | 98.8 | 98.2 |
| SD | 2.7 | 0.9 | 2.0 |
| % CV | 3 | 1 | 2 |
| Min | 92.9 | 97.4 | 92.9 |
| Max | 99.9 | 99.7 | 99.9 |
| Cohort 4: 200 mg BID (n = 8) | | | |
| Mean | 99.5 | 98.8 | 99.1 |
| SD | 0.6 | 2.5 | 1.8 |
| % CV | 1 | 3 | 2 |
| Min | 98.2 | 92.8 | 92.8 |
| Max | 100.0 | 100.0 | 100.0 |

[a] % $AUEC_{0-12}$ is defined as the Area Under the Effect Curve (AUEC) over a 12-hour dosing interval from 0 h to 12 h, expressed as the percent of maximal inhibition over the entire interval. % $AUEC_{0-12}$ was calculated using the inhibition of AP activity determined at time points through the interval.
[b] Combined analysis comprises two observation (Days 7 and 14) × N individuals in each cohort.

Second, the duration of AP inhibition was calculated as the elapsed time between 0 h and 12 h during which AP inhibition was 90% or greater ($DUTRATION_{0-12}$). Starting and ending time points with 90% or greater inhibition were estimated where needed by linear interpolation. A maximum $DUTRATION_{0-12}$ value of 12 h indicates 90% or greater inhibition continuously from 0 h to 12 h. At 40 mg BID and 80 mg BID, calculated $DURATION_{0-12}$ values (Days 7 and 14, combined analysis) were 2.3 hr. and 7.6 hr., respectively, reflecting the substantial recovery of AP hemolysis activity observed between doses. At 120 mg BTD and 200 mg BID, mean $DUTRATION_{0-12}$ values (Days 7 and 14, combined analysis) were 11.3 h and 11.7 h respectively, approaching the maximum possible value of 12 h (Table 9). These values agree with findings derived from the AP Wieslab assay, with $DURATION_{0-12}$ values (Days 7 and 14, combined analysis) of 11.6 h and 11.9 h at 120 mg BID and 200 mg BID, respectively.

TABLE 9

Duration of AP Hemolysis Inhibition from 0 h to 12 h
($DURATION_{0-12}$) in Multiple-Dose Cohorts: Days 7 and 14

| | $DURATION_{0-12}$ (hr) [a] | | |
|---|---|---|---|
| | Day 7 | Day 14 | Days 7 and 14 Combined Analysis [b] |
| Cohort 1: 40 mg BID | | | |
| Mean | 2.0 | 2.6 | 2.3 |
| SD | 1.6 | 1.4 | 1.5 |
| % CV | 82 | 55 | 65 |
| Min | 0.0 | 0.0 | 0.0 |
| Max | 3.5 | 4.0 | 4.0 |
| Cohort 2: 80 mg BID | | | |
| Mean | 7.3 | 8.0 | 7.6 |
| SD | 2.1 | 2.8 | 2.4 |
| % CV | 29 | 35 | 32 |
| Min | 4.6 | 4.1 | 4.1 |
| Max | 11.0 | 12.0 | 12.0 |
| Cohort 3: 120 mg BID | | | |
| Mean | 10.9 | 11.6 | 11.3 |
| SD | 1.4 | 0.6 | 1.1 |
| % CV | 13 | 5 | 10 |
| Min | 8.8 | 10.6 | 8.8 |
| Max | 12.0 | 12.0 | 12.0 |
| Cohort 4: 200 mg BID | | | |
| Mean | 11.9 | 11.5 | 11.7 |
| SD | 0.2 | 1.1 | 0.8 |
| % CV | 2 | 10 | 7 |
| Min | 11.5 | 8.8 | 8.8 |
| Max | 12.0 | 12.0 | 12.0 |

[a] $DURATION0-12$ is defined as the elapsed time from 0 h to 12 h during which serum AP inhibition was 90% or greater.
[b] Combined analysis comprises two observation (Days 7 and 14) × N individuals in each cohort.

Figure 21A:
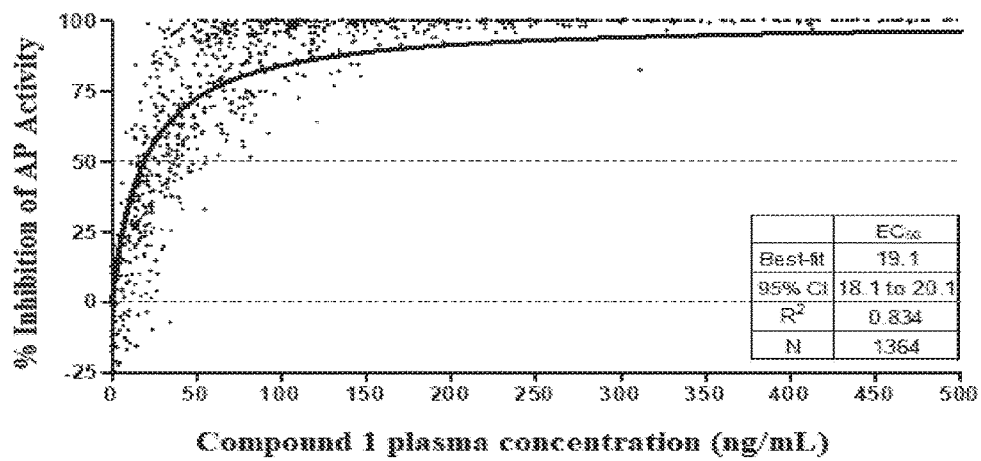
FIG. 21A is a graphical display of a PK-PD evaluation from plasma Compound 1 concentrations and percent inhibition of AP Wieslab activity in corresponding serum samples. Nonlinear regression analysis was performed using a simple $E_{max}$ model. Best-fit values and 95% confidence intervals are in ng/mL. The x-axis is Compound 1 Plasma Concentration measured in ng/mL and the y-axis is % Inhibition of AP Activity measured as a percentage.
Figure 21B:
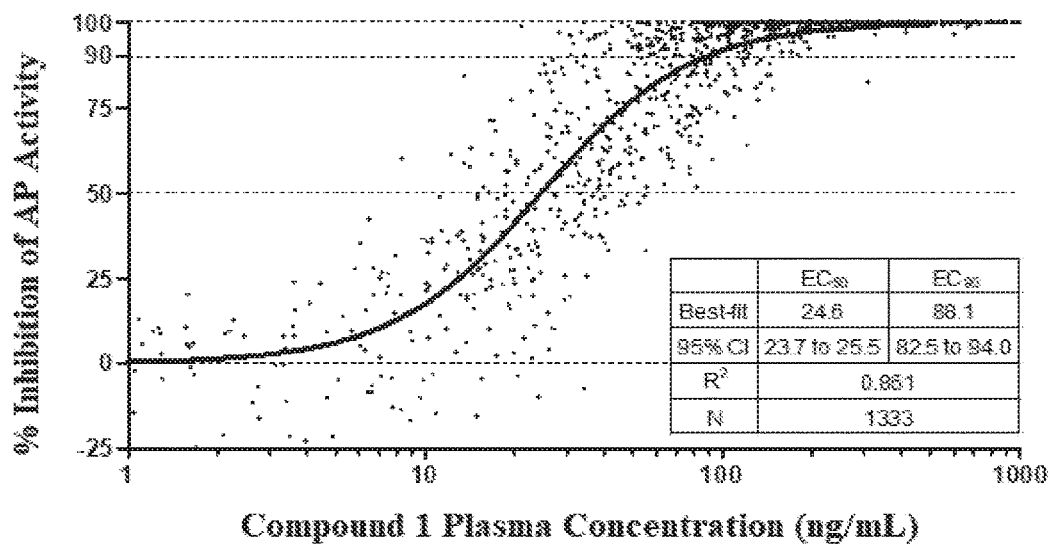
FIG. 21B is a graphical display of a PK-PD evaluation from plasma Compound 1 concentrations and percent inhibition of AP Wieslab activity in corresponding serum samples. Nonlinear regression analysis was performed using a four-parameter sigmoidal model. Best-fit values and 95% confidence intervals are in ng/mL. The x-axis is Compound 1 Plasma Concentration measured in ng/mL and the y-axis is % Inhibition of AP Activity measured as a percentage.

PK-PD Relationship Between Plasma ACH-5228 Concentration and Serum AP Inhibition in Multiple-Dose Cohorts The PK-PD relationship between time-matched plasma Compound 1 concentrations (PK) and inhibition of serum AP hemolysis activity (PD) was evaluated across all time points and individuals in the multiple-dose cohorts using two models (FIGS. 21A & 21B). The data were analyzed by nonlinear regression using a simple $E_{max}$ model to determine $EC_{50}$ and, for a closer estimate of the concentration required for efficacious activity, using a sigmoidal model to determine $EC_{50}$ and $EC_{90}$.

Analysis with both models demonstrated a concentration-dependent inhibition of AP activity following dosing. Analysis using the $E_{max}$ model yielded an $EC_{50}$ value of 19.1 ng/mL, with a 95% confidence interval (CI) of 18.1 ng/mL to 20.1 ng/mL. Analysis with the sigmoidal model yielded $EC_{50}$ and $EC_{90}$ values of 24.6 ng/mL and 88.1 ng/mL, with a 95% CI around the $EC_{90}$ of 82.5 ng/mL to 94.0 ng/mL. These values agree with findings derived from the AP Wieslab assay, which yielded an $EC_{50}$ value of 14.3 ng/mL using the $E_{max}$ model, and $EC_{50}$ and $EC_{90}$ values of 19.2 ng/mL and 66.9 ng/mL, respectively, using the sigmoidal model.

Summary

Following single-dose Compound 1 administration in the Phase 1 SAD study, rapid and nearly complete suppression of serum AP activity was established using the AP hemolysis assay. Mean pre-dose activity was reduced to 10% or lower from 1.5 h through 16 h following dosing in 240 mg, fasted subjects, and from 2 h through 6 h following dosing in 120 mg, fed subjects.

Results from the four multiple-dose cohorts in Phase 1 MAD study, Compound 1 demonstrated rapid and dose-dependent inhibition of AP hemolysis activity following Compound 1 administration. Compound 1 at 40 mg BID (Group 1) and 80 mg BID (Group 2) achieved partial to nearly complete AP inhibition, but with substantial recovery before the end of each 12-hour dosing period. Compound 1 at 120 mg BID (Group 3) and 200 mg BID (Group 4) achieved essentially complete AP inhibition that was maintained through much of the 12 hour dosing periods, with AP activity maintained below 10% for 10 to 12 hours of the 12 hour dosing periods on Days 7 and 14 (representing steady-state PK conditions). Two calculated PD parameters developed for this study, $DURATION_{0-12}$ and $\% AUEC_{0-12}$, further describe the substantial and sustained AP inhibition by Compound 1 at 120 mg and 200 mg BID.

The PK-PD relationship between plasma Compound 1 concentrations (PK) and serum AP hemolysis inhibition (PD) was evaluated across the multiple-dose cohorts. Analysis using a simple $E_{max}$ model yielded an $EC_{50}$ value of 19.1 ng/mL. Further analysis using a sigmoidal model yielded $EC_{50}$ and $EC_{90}$ values of 24.6 ng/mL and 88.1 ng/mL, respectively. Comparable results were obtained in a parallel analysis of ex vivo AP Wieslab results, which yielded an $EC_{50}$ value of 14.3 ng/mL using the $E_{max}$ model, and $EC_{50}$ and $EC_{90}$ values of 19.2 ng/mL and 66.9 ng/mL, respectively, using the sigmoidal model.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A method of modulating immune function in a patient in need thereof, the method comprising administering to the patient (1R,3S,5R)-2-(2-(3-acetyl-5-(2-methylpyrimidin-5-yl)-1H-indazol-1-yl) acetyl)-N-(6-bromo-3-methylpyridin-2-yl)-5-methyl-2-azabicyclo[3.1.0] hexane-3-carboxamide (Compound 1), or a pharmaceutically acceptable salt thereof, at a dosage of between about 100 mg and about 200 mg twice a day (BID).

2. The method of claim 1, wherein Compound 1, or a pharmaceutically acceptable salt thereof, is administered at a dosage of about 120 mg BID.

3. The method of claim 1, wherein Compound 1, or a pharmaceutically acceptable salt thereof, is administered at a dosage of about 180 mg BID.

4. The method of claim 1, wherein Compound 1, or a pharmaceutically acceptable salt thereof, is administered at a dosage of about 200 mg BID.

5. The method of claim 1, wherein the method provides a lower of two different diurnal $C_{trough}$ levels in the patient's plasma of at least 65 ng/ml.

6. The method of claim 5, wherein the method provides a lower of two different diurnal $C_{trough}$ levels in the patient's plasma of between about 65 ng/ml and 95 ng/ml.

7. The method of claim 5, wherein the method provides a lower of two different diurnal $C_{trough}$ levels in the patient's plasma of about 90 ng/mL+10%.

8. The method of claim 5, wherein the method provides a $C_{trough}$ in the patient's plasma of at least 100 ng/mL±10%.

9. The method of claim 5, wherein the $C_{trough}$ level in the patient's plasma is measured in a patient with a disorder selected from paroxysmal nocturnal hemoglobinuria (PNH), fatty liver, liver inflammation, cirrhosis, liver failure, amyotrophic lateral sclerosis; rheumatoid arthritis, a complement alternative pathway (AP)-associated nephropathy, a component 3 glomerulopathy (C3G) disorder, C3 glomerulonephritis (C3GN), dense deposit disease (DDD), a membranoproliferative glomerulonephritis (MPGN), immune-complex membranoproliferative glomerulonephritis (IC-MPGN), amyotrophic lateral sclerosis; rheumatoid arthritis, a complement alternative pathway (AP)-associated nephropathy, glomerulopathy, age-related macular degeneration (AMD), retinal degeneration, ophthalmic disease, geographic atrophy, early or neovascular age-related macular degeneration, autoimmune dry eye diseases, and environmental dry eye disease.

10. The method of claim 1, wherein the method provides a $C_{max}$ of less than about 2000 ng/ml.

11. The method of claim 10, wherein the method provides a $C_{max}$ of less than about 1000 ng/ml.

12. The method of claim 1, wherein Compound 1, or the pharmaceutically acceptable salt thereof, is administered for one month or longer.

13. The method of claim 12, wherein Compound 1, or the pharmaceutically acceptable salt thereof, is administered for at least six months.

* * * * *

UNITED STATES PATENT AND TRADEMARK OFFICE
CERTIFICATE OF CORRECTION

| | | |
|---|---|---|
| PATENT NO. | : 12,239,645 B2 | Page 1 of 1 |
| APPLICATION NO. | : 17/414057 | |
| DATED | : March 4, 2025 | |
| INVENTOR(S) | : Huang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 809 days.

Signed and Sealed this
Twenty-sixth Day of August, 2025

Coke Morgan Stewart
*Acting Director of the United States Patent and Trademark Office*